(12) United States Patent
Brett et al.

(10) Patent No.: US 12,181,847 B1
(45) Date of Patent: Dec. 31, 2024

(54) ACTIVITY-BASED DEVICE RECOMMENDATIONS

(71) Applicant: Amazon Technologies, Inc., Seattle, WA (US)

(72) Inventors: Charles Edwin Ashton Brett, Seattle, WA (US); William Evan Welbourne, Seattle, WA (US); Hongyang Wang, Seattle, WA (US); Akshay Kumar, Seattle, WA (US); George Strajan, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 414 days.

(21) Appl. No.: 16/832,385

(22) Filed: Mar. 27, 2020

(51) Int. Cl.
*G05B 19/42* (2006.01)
*G05B 19/042* (2006.01)
(Continued)

(52) U.S. Cl.
CPC ......... *G05B 19/042* (2013.01); *G06F 1/3296* (2013.01); *G06F 3/167* (2013.01);
(Continued)

(58) Field of Classification Search
CPC .............. G05B 15/02; G05B 19/042; G05B 2219/2642; H04W 12/08; H04W 48/10; H04W 4/90; G06F 21/55; G06F 21/31; G06F 3/0485; G06F 1/3296; G06F 3/167; F24F 11/33; H04L 12/2816; H04L 5/0048; G06Q 30/0205; A61N 1/36564; G08B 13/1672; G08B 21/0469; G08B 19/00;
(Continued)

(56) References Cited

U.S. PATENT DOCUMENTS 7,907,945 B2 * 3/2011 Deprun ................. H04W 48/10
455/435.2
8,332,500 B1 * 12/2012 Singleton ............... G06Q 10/10
709/224
(Continued)

FOREIGN PATENT DOCUMENTS

AU 2012261958 A1 * 1/2014 ........... G06F 16/243
AU 2014233259 A1 * 9/2015 ......... G06F 16/2455
(Continued)

OTHER PUBLICATIONS

Office Action for U.S. Appl. No. 16/832,520, mailed on Aug. 4, 2022, Brett, "Activity-Based Device Recommendations", 7 pages.
(Continued)

*Primary Examiner* — Steven P Sax
(74) *Attorney, Agent, or Firm* — Lee & Hayes, P.C.

(57) ABSTRACT

Systems and methods for activity-based device recommendations are disclosed. For example, historical usage data associated with a device may indicate that the device is likely to be associated with a given state at a given time. When the device is not in the anticipated state, a recommendation to transition the device state, for example, may be sent. Additionally, a determination of the activity state associated with the device, such as an active state, an asleep state, and/or an away state may be utilized to determine the recommendation to surface, to determine whether to send a recommendation, and when and/or how to send the recommendation.

20 Claims, 16 Drawing Sheets

(51) Int. Cl.
  *G06F 1/3296* (2019.01)
  *G06F 3/16* (2006.01)
  *G06N 20/00* (2019.01)
  *G06V 10/60* (2022.01)
  *G08B 13/00* (2006.01)
  *G10L 15/22* (2006.01)
  *G16H 40/67* (2018.01)

(52) U.S. Cl.
  CPC ............. *G06N 20/00* (2019.01); *G06V 10/60* (2022.01); *G08B 13/00* (2013.01); *G10L 15/22* (2013.01); *G05B 2219/2642* (2013.01); *G10L 2015/223* (2013.01); *G16H 40/67* (2018.01)

(58) Field of Classification Search
  CPC ....... G08B 13/00; A61B 5/681; A61B 5/6833; A61B 5/6898; A61B 5/02444; A61B 5/747; A61B 7/04; A61B 5/1116; G01K 1/20; G06N 20/00; G06V 10/60; G10L 15/22
  See application file for complete search history.

(56) References Cited

U.S. PATENT DOCUMENTS

| | | | |
|---|---|---|---|
| 9,094,539 B1* | 7/2015 | Noble | H04N 21/00 |
| 9,396,599 B1* | 7/2016 | Malhotra | G07C 9/38 |
| 9,642,529 B1* | 5/2017 | Siddiqui | A61B 5/02444 |
| 9,665,169 B1* | 5/2017 | Dai | A61B 5/6898 |
| 9,874,933 B1* | 1/2018 | Carryer | G06F 3/013 |
| 10,088,818 B1* | 10/2018 | Mathews | G05B 15/02 |
| 10,397,046 B1* | 8/2019 | Gupta | G06F 16/9535 |
| 10,453,098 B2* | 10/2019 | Zomet | H04L 12/2812 |
| 10,510,220 B1* | 12/2019 | Moore, Jr. | G10K 11/00 |
| 10,534,925 B2* | 1/2020 | Israel | G06F 21/55 |
| 11,430,008 B2* | 8/2022 | Demsey | G06Q 30/0277 |
| 2010/0207781 A1* | 8/2010 | Shuster | G08B 19/00 340/8.1 |
| 2012/0226912 A1* | 9/2012 | King | G06F 21/31 713/183 |
| 2014/0098727 A1* | 4/2014 | Murabito | H04W 52/0277 370/311 |
| 2014/0276227 A1* | 9/2014 | Perez | A61B 7/04 600/586 |
| 2014/0304536 A1 | 10/2014 | Moy | |
| 2015/0100167 A1* | 4/2015 | Sloo | F24F 11/33 700/278 |
| 2015/0164409 A1* | 6/2015 | Benson | A61B 5/1116 600/595 |
| 2015/0363701 A1 | 12/2015 | Lin et al. | |
| 2015/0366518 A1* | 12/2015 | Sampson | A61B 5/7275 600/509 |
| 2015/0370323 A1* | 12/2015 | Cieplinski | G06F 3/0485 345/156 |
| 2015/0374267 A1* | 12/2015 | Laughlin | A61B 5/681 702/19 |
| 2016/0029458 A1* | 1/2016 | Liu | H05B 47/175 700/32 |
| 2016/0072326 A1* | 3/2016 | Nilles | H02J 7/0069 320/137 |
| 2016/0234034 A1* | 8/2016 | Mahar | G05B 15/02 |
| 2016/0261425 A1* | 9/2016 | Horton | H04L 12/2803 |
| 2016/0330311 A1 | 11/2016 | Du et al. | |
| 2017/0108236 A1* | 4/2017 | Guan | G05B 19/042 |
| 2017/0292893 A1* | 10/2017 | Bunker | G01M 3/26 |
| 2017/0309142 A1* | 10/2017 | Phillips | G08B 13/1672 |
| 2017/0323345 A1* | 11/2017 | Flowers | G06Q 30/0205 |
| 2018/0004176 A1* | 1/2018 | Tsubota | H04L 12/2818 |
| 2018/0031264 A1 | 2/2018 | Atchison et al. | |
| 2018/0146062 A1* | 5/2018 | Sundar | H04L 5/0048 |
| 2018/0150129 A1* | 5/2018 | Thomas | H04L 67/75 |
| 2018/0270534 A1* | 9/2018 | Badawiyeh | H04N 21/23424 |
| 2018/0284881 A1* | 10/2018 | Briggs | A63G 33/00 |
| 2018/0287808 A1* | 10/2018 | Liston | H04L 12/2816 |
| 2018/0348844 A1* | 12/2018 | Lingutla | G06F 1/3209 |
| 2019/0069154 A1* | 2/2019 | Booth | H04W 4/90 |
| 2019/0122522 A1* | 4/2019 | Stefanski | G08B 21/0423 |
| 2019/0305597 A1* | 10/2019 | Venkatraman | H02J 7/00034 |
| 2019/0350526 A1* | 11/2019 | Biederman | A61B 5/6833 |
| 2019/0381323 A1* | 12/2019 | Sharma | A61N 1/36564 |
| 2020/0086133 A1* | 3/2020 | Wang | A61B 5/747 |
| 2020/0167834 A1* | 5/2020 | Matsuoka | G06Q 30/0278 |
| 2020/0193335 A1* | 6/2020 | Sekhar | G06Q 10/025 |
| 2020/0217727 A1* | 7/2020 | Heitz | G01K 1/20 |
| 2020/0349609 A1* | 11/2020 | Shin | G06Q 30/0262 |
| 2021/0150873 A1* | 5/2021 | Shouldice | G08B 21/0469 |
| 2021/0194888 A1* | 6/2021 | Bhaskar S | H04L 63/102 |
| 2022/0036466 A1* | 2/2022 | Harvey | H04L 67/306 |
| 2022/0103395 A1* | 3/2022 | Shi | G05B 15/02 |

FOREIGN PATENT DOCUMENTS

| | | | | |
|---|---|---|---|---|
| AU | 2014241282 A1 | * | 9/2015 | G05B 15/02 |
| AU | 2014233248 A1 | * | 10/2015 | A61J 1/03 |
| AU | 2015224489 A1 | * | 10/2015 | G01S 19/34 |
| AU | 2016205850 A1 | * | 7/2017 | A61B 3/16 |
| CA | 2905834 C | * | 8/2018 | A47C 19/025 |
| CA | 3060274 A1 | * | 6/2020 | |
| CA | 3017255 C | * | 10/2023 | A61B 5/0022 |
| CA | 3101984 C | * | 10/2023 | A45D 42/00 |
| CA | 3156908 C | * | 6/2024 | |
| CN | 102740919 A | * | 10/2012 | A61B 5/4809 |
| CN | 104052423 A | * | 9/2014 | H04R 1/1041 |
| CN | 104142659 A | * | 11/2014 | G05B 15/02 |
| CN | 104994343 A | * | 10/2015 | |
| CN | 106264447 A | * | 1/2017 | |
| CN | 107430716 A | * | 12/2017 | G06N 20/00 |
| CN | 107548500 A | * | 1/2018 | A61M 21/00 |
| CN | 107683486 A | * | 2/2018 | G06N 5/025 |
| CN | 107883520 A | * | 4/2018 | |
| CN | 108014010 A | * | 5/2018 | |
| CN | 108604363 A | * | 9/2018 | A61B 5/002 |
| CN | 112861139 A | * | 5/2021 | G06F 21/31 |
| CN | 112862141 A | * | 5/2021 | G06K 9/00536 |
| CN | 113632061 A | * | 11/2021 | G06F 3/167 |
| DE | 112018000717 T5 | * | 1/2020 | G06F 1/3206 |
| ES | 2942279 T3 | * | 5/2023 | A63G 25/00 |
| FR | 2956762 A1 | * | 8/2011 | H04L 12/2809 |
| JP | 2008000222 A | * | 1/2008 | |
| WO | WO-0175653 A2 | * | 10/2001 | G06F 1/163 |
| WO | WO-2020235141 A1 | * | 11/2020 | A61B 5/4809 |

OTHER PUBLICATIONS

Office Action for U.S. Appl. No. 18/243,020, dated Jun. 21, 2024 9 pages.

* cited by examiner

600

602 Receive, from voice-enabled devices, first data indicating events associated with voice-enabled devices, events associated with detection of user devices or user-related audio

604 Generate, utilizing machine-learning model, second data including activity-labeling data associated with first data, activity-labeling data indicating that given event of events is associated with activity state, activity state corresponding to away state indicating absence of user presence, active state indicating user movement, or an asleep state indicating user presence without user movement

606 Cause activity models to be trained utilizing neural network model and second data, activity models including: historical-activity model configured to determine activity state associated with given voice-enabled device of voice-enabled devices at past time; current-activity model configured to determine activity state associated with given voice-enabled device at present time; and future-activity model configured to determine activity state associated with given voice-enabled device at time that has not yet occurred

608 Receive, from application, request data for activity state of given voice-enabled device

610 Generate, utilizing at least one of activity models, third data representing activity state

612 Send third data to application for generating recommendation associated with activity state

FIG. 6

ACTIVITY-BASED DEVICE RECOMMENDATIONS

BACKGROUND

Electronic devices can now be used for many purposes such as controlling lights, locks, doorbells, plugs, appliances, thermostats, etc. These electronic devices may be utilized in different ways depending on characteristics of the environment in which the electronic devices are disposed. Described herein are improvements in technology and solutions to technical problems that can be used to, among other things, improve the use of electronic devices.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

FIG. 6 illustrates a flow diagram of an example process for smart home activity modeling.

DETAILED DESCRIPTION

Figure 1:
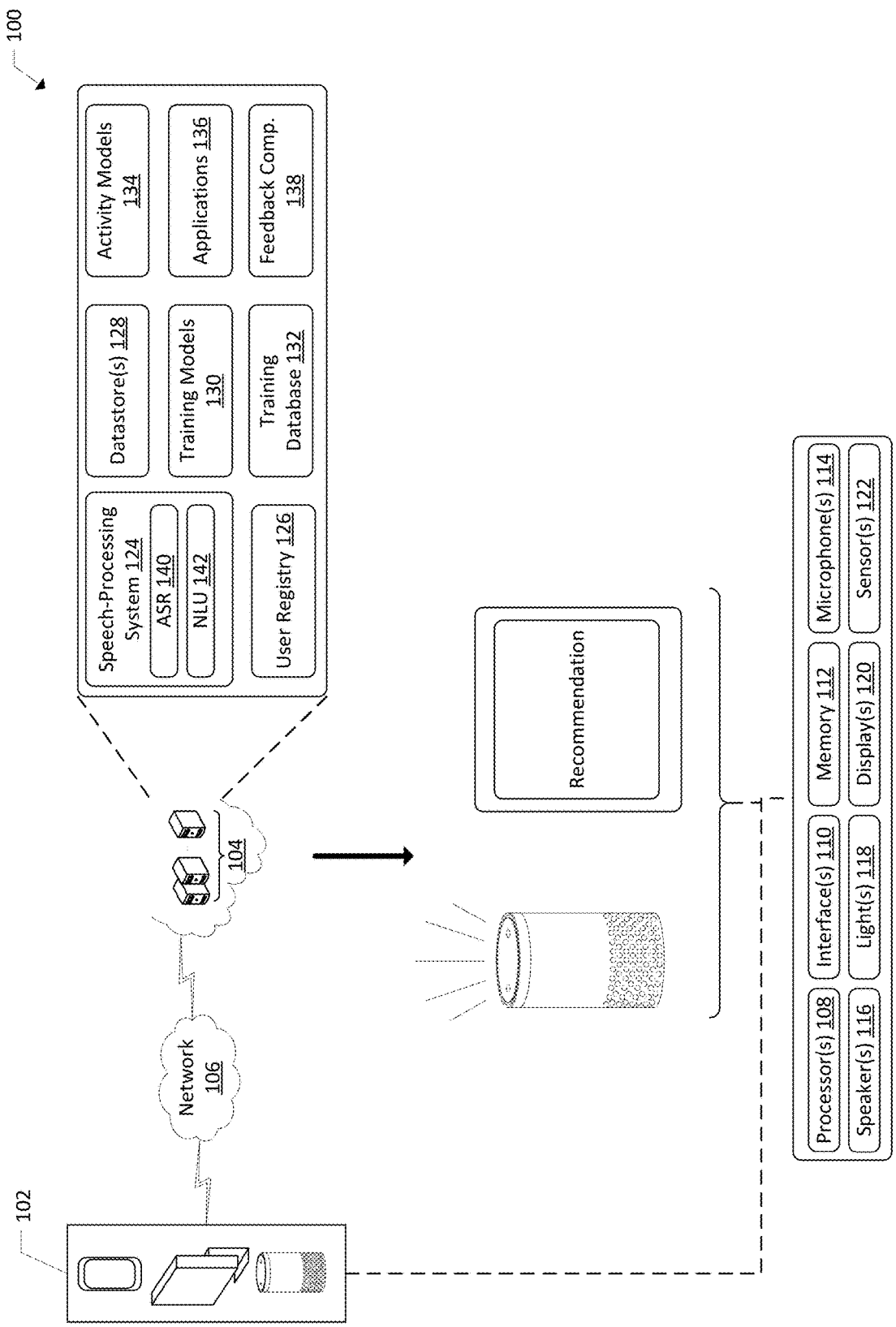
FIG. 1 illustrates a schematic diagram of an example environment for activity-based device recommendations.

Systems and methods for activity-based device recommendations are disclosed. Take, for example, an environment (such as a home, vehicle, office, store, restaurant, or other space) where one or more users may be present. In some examples, the users and/or user devices associated with the users may be physically present in the environment and may be active or otherwise moving within the environment. In other examples, the users and/or user devices may be physically present but the users may not be moving or otherwise causing devices to perform operations, which may indicate that the users are sleeping or otherwise inactive within the environment, for example. In still other examples, the users and/or user device may be absent or otherwise away from the environment. Determining the activity state associated with the environment, such as whether the activity state corresponds to an away state, an active state, or an asleep state, may be useful for one or more applications, such as for determining whether a given application sends a recommendation and/or notification, whether to control operation of devices associated with the environment, etc.

The environments may include one or more electronic devices that may be utilized by the users. For example, the electronic devices may include voice interface devices (e.g., Echo devices, mobile phones, tablets, personal computers, etc.), graphical interface devices (e.g., televisions, set top boxes, virtual/augmented reality headsets, etc.), touch interface devices (tablets, phones, steering wheels, laptops, kiosks, billboard, other devices with buttons, etc.), and accessory devices (e.g., lights, plugs, locks, thermostats, appliances, televisions, clocks, smoke detectors, doorbells, cameras, motion/magnetic/other security-system sensors, etc.). These electronic devices may be situated in a home, in a place a business, healthcare facility (e.g., hospital, doctor's office, pharmacy, etc.), in vehicle (e.g., airplane, truck, car, bus, etc.) in a public forum (e.g., shopping center, store, etc.), for example.

The electronic devices, and/or other system components (such as cameras, motion sensors, door sensors, security-system contacts, and/or other presence-based sensors) associated with the electronic devices, may be configured to generate and/or receive data from one or more other devices associated with the environment. For example, data may be received and/or generated that indicates: the state of the one or more devices (e.g., ON, OFF, standby, actively outputting content, etc.), that a mobile device is in proximity to a given electronic device (e.g., based on the devices are in communicable range of each other), the detection of movement in the environment, an acoustic-event detection component of the electronic device has identified a presence-based audio event, and/or other indicators of activity and/or inactivity. This data may be generated and stored for electronic devices within a given environment and/or for multiple electronic devices associated with multiple disparate environments. The data may be utilized to generate and/or train models for determining the activity state associated with a given user and/or other account profile. It should be understood that while examples of such event data are provided herein, those examples are not by way of limitation. Instead, the event data received from the electronic devices may include any data that may indicate a state of the electronic devices, other devices, and/or the environment.

The event data may be sent to the system, which may store the event data in one or more databases, such as a user registry and/or one or more other types of datastores. The user registry may store event data from devices that are also associated with one or more user accounts. The event data may be made available (e.g., with the user's informed consent) to one or more components of the remote system for smart home activity modeling as described herein.

For example, if a user activates a feature of a smart home system, one or more machine learned models may be generated and be configured to accept the event data associated with a particular user account. The training algorithms may perform an analysis of the event data, including labelling the event data with one or more indicators of an activity state. For example, the training models may include a supervised machine-learning model that has been configured to apply one or more rules to given events to label those events with an activity state. For example, event data indicating that a light has been turned on may be labeled by the supervised machine-learning model as being associated with an active state, as opposed to an inactive state (e.g., asleep or away).

It should be understood that, in examples, an inactive state may include an away state and/or an asleep state. In an away state, presence of a user may not be detected in an environment associated with one or more sensors configured to detect presence. In an asleep state, presence of the user may be detected, but the user may not be moving or may otherwise not be interacting with the environment, such as by providing commands for devices to perform operations. This is in contrast to an active state, where presence of the user is detected and the user is moving or otherwise is interacting with the environment, such as by walking, talking, changing positions, and/or giving commands, for example. The system 100 may determine that user profile data is associated with an active state when one or more signals, such as from smart-home devices or otherwise accessory devices, are received that indicate that a user associated with the user profile data is present and is engaged in an activity in the environment. The one or more signals may include, for example, device-beacon data received from a user device associated with the user that indicates the device is in the environment and that the device is moving. The one or more signals may also include, for example, data indicating interaction of the user with a voice user interface, such as a voice user interface associated with a voice-enabled device. The one or more signals may also include, for example, data indicating that a wake word has been detected, such as by a voice-enabled device. The one or more signals may also include, for example, receipt of user input data requesting operation of a device in the environment. The one or more signals may also include, for example, data indicating that a smart-home device is being operated and/or that another device is being operated and a smart-home device or other device having sensors described herein has detected operation of the smart-home device. Such operations may include, for example, turning lights on and/or off, turning appliances on and/or off from the appliances themselves as opposed to from an application running on a mobile user device, a wireless router device or other network access point receiving data indicating a SSID of a personal device of a user and an indication that such a device is sending data, motion sensor data, ambient noise detection, acoustic event detections, ambient light determinations, signals from a security system, such as signals indicating a security system is in a state where the system is armed but users are still present in the environment, force value detections from devices such as smart beds, etc.

Additionally, for the inactive states, such as the away state or the asleep state, the one or more signals may include the same or similar signals as described above, but where those signals indicate that users are absent from the environment, or that users are present but are asleep. For example, when no device-beaconing data is received, such an occurrence indicates that no mobile personal devices are within the environment, which may be utilized to determine that user profile data is associated with an away mode. Other examples where the signals indicate that user profile data is associated with an away mode include ambient noise satisfying a threshold noise value indicating an environment is emitting only typical ambient background noise. Other indications may include the lack of interaction with smart-home devices, such as for at least a threshold period of time. The one or more signals may also indicate an asleep state in instances where the signals indicate that a user is present, such as from device-beaconing data, but the signals otherwise indicate an inactive state, such as from data indicating a lack of interaction with smart-home devices, a lack of acoustic event detection for events such as footsteps, the lack of detection of user speech from audio data captured by a microphone in the environment, etc. Additionally, the one or more sensors may be configured to detect noises and/or posture indicating an asleep state. For example, breathing and/or snoring may be audible and may be detected from audio data captured from the environment. In further examples, radar-based sensors, such as ultrasonic sensors, may be configured to determine, when user consent has been provided to collect such data, a location of a user, which may indicate that a user is in a sleeping position. Additionally, in examples where the sensors are included in a smart bed, or other object associated with sleeping, signals from those sensors, such as an indication that someone is on the bed, may be utilized. Additionally, contextual data such as the time of day, day of the week, and/or historical data indicating when user profile data is associated with an asleep state may be utilized. For example, it may be more likely that user profile data is associated with an asleep state during the nighttime, such as on a weeknight. Some or all of this information may be utilized to determine that user profile data is associated with an asleep state.

The supervised machine-learning model may generate a training dataset that includes the event data and the labeling data associated with the event data. Additionally, in examples, one or more of the electronic devices and/or user profiles associated with the electronic devices may be predetermined to be included in an evaluation dataset. For example, certain devices may have sensors that are better suited for determining certain activity states and/or use of devices by particular users may be considered more beneficial for accurately determining activity states (e.g., a smart watch that detects standing, sleeping, GPS location, and heartrate may be best at determining the wearer's current activity state). In these examples, a portion of the event data corresponding to the predetermined electronic devices and/or user profiles may be input into a separate supervised machine-learning model to generate the evaluation dataset. The evaluation dataset may represent a smaller subset of the event data utilized to generate the training dataset. The evaluation dataset may be utilized by other models, as described more fully below, to test or otherwise determine the accuracy of the labeling associated with the training dataset.

The training models may also include a neural network model, which may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic device and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network may "learn" how certain events, such as for certain electronic devices and/or environments, impact determining activity states for particular user profile(s).

The activity models generated and/or trained utilizing the neural network model may include one or more activity models for each profile (whether personal, household, or other type of user profile), which are configured to accept event data and generate, as output, results indicating that given event data suggests a given user's activity state and, in examples, a confidence value associated with the activity state determination. The activity models may include a historical-activity model, which may be configured to determine an activity state associated with historical events associated with an electronic device and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week prior to making the determination that a given environment was associated with an asleep state, for example, based at least in part on the event data associated with that given time.

The activity models may also include a current-activity model, which may be configured to determine an activity state associated with recent events associated with a user profile and/or environment. For example, recent events may include events that are currently occurring, such as receipt of audio data indicating presence, and/or receipt of an indication that a device was just operated. In examples, use of the current-activity model may be in association with the electronic device and/or the remote system causing one or more sensors or other components of the electronic device to generate data indicating recent events to be utilized by the current-activity model. The current-activity model may generate, as output, data indicating that a given event corresponds to a given activity state. For example, the current-activity model may be utilized to determine that at a current time a given environment is associated with an active state based at least in part on event data associated with the current time. In examples, the current-activity model may be trained based at least in part on the output from the neural network model and/or from the output of the historical-activity model.

The activity models may also include a future-activity model, which may be configured to predict an activity state associated with events that may occur in the future with respect to an electronic device and/or environment. For example, the future-activity model may be configured to accept, as input features, event data corresponding to the historical events and/or live or near-live events. The future-activity model may generate, as output, data indicating that a given event that is likely to occur at a particular time in the future and/or is likely to correspond to a given activity state. For example, the future-activity model may be utilized to determine that at a given time a week from when the determination is made a given environment is likely to be associated with an away state, for example, based at least in part on historical event data and/or current event data associated with the given environment. In examples, the future-activity model may be trained based at least in part on the output from the historical-activity model and/or the current-activity model. For example, the output of the historical-activity model may include determinations of activity state at past times, while output of the current-activity model may include determinations of activity state at a current time. These activity state determinations may be utilized to train the future-activity model, such as by providing indications of activity state at given times of day and/or days of the week.

The activity models may be made available to one or more applications associated with the remote system and/or one or more other systems. For example, one or more applications may be able to utilize activity state determinations to generate more accurate results and/or to determine when to perform certain operations, such as when to generate and/or send a recommendation and/or other type of notification, when to operate a device (e.g., when to transition a state of a device), etc. In these examples, one or more of the applications may send request data to the activity models for an indication of an activity state of a device and/or environment in the past, at the time of the request, or in the future. In some examples, the request data may indicate which of the activity models are to be utilized for determining the activity state. In other examples, the request data may provide an indication of which events the application would like to determine the activity state for, and the remote system may determine which of the activity models to utilize to provide results relevant to those events. The selected activity model may then query the user registry and/or datastores for the event data relevant to the request from the application and utilize, as input to the selected activity model, features corresponding to the event data. The selected activity model may output data indicating the determined activity state for the device and/or environment at issue and, in examples, a confidence value associated with the determined activity state. The application that sent the request data may then utilize the activity state as determined by the selected activity model to perform one or more actions, such as the sending of a recommendation and/or the operation of a device, for example.

Additionally, in examples, the one or more applications may be configured to cause one or more indications of the determined activity state to be presented by one or more electronic devices. For example, a command may be sent to a voice-enabled device to cause a lighting element of the voice-enabled device to emit light indicating the state of the device associated with the activity state. For example, the lighting element may be caused to emit orange light when a user profile is associated with an away activity state. In other examples, text data may be sent to a user device and the command may cause corresponding text to be displayed indicating the device state. Additional or different indications of determined activity state may also be displayed. In examples, users of such devices may provide user input indicating that the device is accurately or inaccurately in the indicated state. User input data corresponding to this user input may be sent from the device to a feedback component of the remote system. The feedback component may be configured to receive the user input data and utilize the user input data to train one or more of the models, such as the supervised machine-learning models and/or the neural network model. By so doing, the feedback component may generate a positive dataset, in situations where the user input indicates accurate activity state determinations, indicating an approximated ground truth that the events associated with a given activity state determination were in fact associated with the determined activity state. The feedback component may also generate a negative dataset, in situations where the user input indicates inaccurate activity state determinations, indicating that the events associated with that activity state determination were not associated with the determined activity state.

By utilizing the activity models described above, the applications may utilize activity state data to determine: when and/or how to send recommendations, when to cause certain devices to transition to certain modes, and/or when to perform other actions associated with the devices. For example, a given application may be configured to detect anomalies in user behavior when a device is requested by a user to track user movement, such as by an aging-in-place user and/or exercising user. The application may utilize one or more signals to detect such anomalies, such as user movement patterns, acoustic-event detection determinations, etc. The application, utilizing the techniques described herein, may also utilize the activity models to more accurately identify historic events associated with the device that may be utilized to compare with current events for anomaly detection. For example, the application may be able to utilize events that occurred during an awake state for detecting anomalies when the environment is currently associated with an awake state. By so doing, the applications may utilize the determined activity states as described herein to more accurately determine which data to utilize for making application-specific determinations, and/or to increase relevant features to be utilized for making such application-specific determinations.

In additional examples, the activity-based determinations described herein may be utilized to determine what recommendation to provide to a user device and/or when to send such a recommendation. For example, device-usage data may be utilized by a remote system to determine when a recommendation is to be surfaced to a user device. By way of example, a given device may be associated with a given device-usage pattern. That device-usage pattern may indicate when a device is operated, how the device is operated, and/or details associated with the device, such as a naming indicator associated with the device and/or the device type of the device, etc. This information may be utilized to determine when a recommendation or otherwise a "hunch" is to be surfaced to a user device. The recommendations may include requests to operate the device in a certain way, to change information associated with the device, to add the device to a device group, to add the device to a device routine, etc. In addition to utilizing the device-usage data to determine when and how to surface such recommendations, the activity-based determinations described herein may also be used to determine when and how to surface recommendations.

For example, when the activity model(s) described herein determine that a given device and/or environment is associated with an active state, the recommendations may be provided to a device within the environment for output by the device because a user is currently in that environment and is moving in a manner associated with an active state. In other examples, such as when the environment is associated with an asleep state, the recommendation may not be to output a notification by the device because a user is present but asleep. The recommendation when the user is asleep may be provided to a user device by way of a message that may be viewed by the user at a later time and will not interrupt the user's sleep. In addition to utilizing activity-based determinations to determine when and how to provide a recommendation, the activity-based determinations may also be utilized to determine what recommendation to provide. For example, when a user is associated with an away state and the device-usage data indicates that a smart door lock is typically locked when the user is away but in this instance the smart door lock is in an unlocked state, the system may cause a recommendation to be presented, which suggests the smart door lock should be transitioned to a locked state. In still other examples, the activity-based determinations may be utilized to determine to automatically perform an action without sending a recommendation and instead, in examples, send a notification that the action has been taken. For example, if an environment is associated with an asleep state, indicating that a user is present and asleep, instead of surfacing a recommendation to lock a smart door lock that is typically in a locked state but is currently in an unlocked state, the system may cause the device to transition to the locked state and provide a notification of the action to a user device in a manner that is designed to let the user continue to sleep.

The present disclosure provides an overall understanding of the principles of the structure, function, manufacture, and use of the systems and methods disclosed herein. One or more examples of the present disclosure are illustrated in the accompanying drawings. Those of ordinary skill in the art will understand that the systems and methods specifically described herein and illustrated in the accompanying drawings are non-limiting embodiments. The features illustrated or described in connection with one embodiment may be combined with the features of other embodiments, including as between systems and methods. Such modifications and variations are intended to be included within the scope of the appended claims.

Additional details are described below with reference to several example embodiments.

FIG. 1 illustrates a schematic diagram of an example system 100 for smart home activity modeling. The system 100 may include, for example, electronic devices 102, which may include communal devices, personal devices, and/or devices configured with sensors to detect environmental changes. In certain examples, at least some of the devices 102 may be voice-enabled devices (e.g., Echo devices, mobile phones, tablets, personal computers, etc.), video interface devices (e.g., televisions, set top boxes, virtual/augmented reality headsets, etc.), touch interface devices (tablets, phones, laptops, kiosks, billboard, etc.), and accessory devices (e.g., lights, plugs, locks, thermostats, appliances, televisions, clocks, smoke detectors, doorbells, cameras, motion/magnetic/other security-system sensors, etc.). These electronic devices 102 may be situated in a home, a place a business, healthcare facility (e.g., hospital, doctor's office, pharmacy, etc.), in vehicle (e.g., airplane, truck, car, bus, etc.), and/or in a public forum (e.g., shopping center, store, etc.), for example. The system 100 may also include one or more personal devices, which may be electronic devices, such as a mobile phone, tablet, laptop, wearable device, and/or other computing device that is specifically associated with a given user profile. The electronic devices 102 and the personal devices may be configured to send data to and/or receive data from a remote system 104, such as via a network 106. Additionally, it should be understood that a given space and/or environment may include numerous electronic devices 102 and/or personal devices. It should also be understood that when a "space" or "environment" is used herein, those terms mean an area and not necessarily a given room, building, or other structure, unless otherwise specifically described as such.

The electronic devices 102 may include one or more components, such as, for example, one or more processors 108, one or more network interfaces 110, memory 112, one or more microphones 114, one or more speakers 116, one or more lights 118, one or more displays 120, and/or one or more sensors 122. The microphones 114 may be configured to capture audio, such as user utterances, and generate corresponding audio data. The speakers 116 may be configured to output audio, such as audio corresponding to audio data received from another device and/or the system 104. The lights 118 may be configured to emit light, such as into the environment in which the electronic device 102 is disposed. The displays 120 may be configured to display images corresponding to image data, such as image data received from the remote system 104 and/or one or more other electronic devices 102. The sensors 122 may be configured to sense one or more environmental changes in the environment in which the electronic device 102 is disposed. The sensors 122 may include, by way of example, radar, audio sensors such as the microphones 114, ultrasonic sensors, cameras, temperature sensors, motion sensors, light sensors, etc. It should be understood that while several examples used herein include a voice-enabled device that allows users to interact therewith via user utterances, one or more other devices, which may not include a voice interface, may be utilized instead of or in addition to voice-enabled devices. In these examples, the device may be configured to send and receive data over the network 106 and to communicate with other devices in the system 100. As such, in each instance where a voice-enabled device is utilized, a computing device that does not include a voice interface may also or alternatively be used. It should be understood that when voice-enabled devices are described herein, those voice-enabled devices may include phones, computers, and/or other computing devices.

The remote system 104 may include components such as, for example, a speech-processing system 124, a user registry 126, one or more datastores 128, a speaker identification component 126, a device-arbitration component 128, training models 130, training databases 132, activity models 134, one or more applications 136, and/or a feedback component 138. It should be understood that while the speech-processing system 124 and the other components are depicted as separate from each other in FIG. 1, some or all of the components may be a part of the same system. The speech-processing system 124 may include an automatic speech recognition component (ASR) 140 and/or a natural language understanding component (NLU) 142. Each of the components described herein with respect to the remote system 104 may be associated with their own systems, which collectively may be referred to herein as the remote system 104, and/or some or all of the components may be associated with a single system. Additionally, the remote system 104 may include one or more applications, which may be described as skills. "Skills," as described herein may be applications and/or may be a subset of an application. For example, a skill may receive data representing an intent. For example, an intent may be determined by the NLU component 142 and/or as determined from user input via a computing device. Skills may be configured to utilize the intent to output data for input to a text-to-speech component, a link or other resource locator for audio data, and/or a command to a device, such as the device 102.

In instances where a voice-enabled device is utilized, skills may extend the functionality of devices 102 that can be controlled by users utilizing a voice-user interface. In some examples, skills may be a type of application that may be useable in association with accessory devices and may have been developed specifically to work in connection with given accessory devices. Additionally, skills may be a type of application that may be useable in association with the voice-enabled device and may have been developed specifically to provide given functionality to the voice-enabled device. In examples, a non-skill application may be an application that does not include the functionality of a skill. Speechlets, as described herein, may be a type of application that may be usable in association with voice-enabled devices and may have been developed specifically to work in connection with voice interfaces of voice-enabled devices. The application(s) may be configured to cause processor(s) to receive information associated with interactions with the voice-enabled device. The application(s) may also be utilized, in examples, to receive input, such as from a user of a personal device and/or the voice-enabled device and send data and/or instructions associated with the input to one or more other devices.

The components of the remote system 104 are described in detail below. In examples, some or each of the components of the remote system 104 may include their own processor(s), network interface(s), and/or memory. As such, by way of example, the speech-processing system 124 may include and/or be associated with processor(s), network interface(s), and/or memory. The other components of the remote system 106, such as the activity models 134, may include and/or be associated with different processor(s), network interface(s), and/or memory, or one or more of these components may utilize some or all of the same processor(s), network interface(s), and/or memory utilized by the speech-processing system 124. These components are described in detail below. Additionally, the operations and/or functionalities associated with and/or described with respect to the components of the remote system 104 may be performed utilizing cloud-based computing resources. For example, web-based systems such as Elastic Compute Cloud systems or similar systems may be utilized to generate and/or present a virtual computing environment for performance of some or all of the functionality described herein. Additionally, or alternatively, one or more systems that may be configured to perform operations without provisioning and/or managing servers, such as a Lambda system or similar system, may be utilized.

The user registry component 126 may be configured to determine and/or generate associations between users, user accounts, and/or devices. For example, one or more associations between user accounts may be identified, determined, and/or generated by the user registry 126. The user registry 126 may additionally store information indicating one or more applications and/or resources accessible to and/or enabled for a given user account. Additionally, the user registry 126 may include information indicating device identifiers, such as naming identifiers, associated with a given user account, as well as device types associated with the device identifiers. The user registry 126 may also include information indicating user account identifiers, naming indicators of devices associated with user accounts, and/or associations between devices, such as the devices 102. The user registry 126 may also include information associated with usage of the devices 102. It should also be understood that a user account may be associated with one or more than one user profiles. It should also be understood that the term "user account" may be used to describe a set of data and/or functionalities associated with a given account identifier. For example, data identified, determined, and/or generated while using some or all of the system 100 may be stored or otherwise associated with an account identifier. Data associated with the user accounts may include, for example, account access information, historical usage data, device-association data, and/or preference data.

The datastores 128 may be configured to receive and/or generate data associated with use of the electronic devices 102 and/or one or more accessory devices. For example, the electronic devices 102 may be utilized to provide responses to user requests and/or other interactions may occur between the electronic devices 102 and accessory devices and/or one or more users. Usage data may be identified, determined, and/or generated that indicates some or each of these interactions. Timing data may also be identified that indicates a time at which some or each of these interactions took place. The datastores 128 may also store data associated with detected events by sensors 122 of the electronic devices 102. It should be understood that while the user registry 126 and the datastores 128 are illustrated as separate components, the user registry 126 and the datastores 128 may be the same component. In examples, the datastores 128 may store data utilized by the training models 130, as discussed more fully herein.

The speech-processing system 124 may be configured to receive audio data from the devices 102 and/or other devices and perform speech-processing operations. For example, the ASR component 140 may be configured to generate text data corresponding to the audio data, and the NLU component 142 may be configured to generate intent data corresponding to the audio data. In examples, intent data may be generated that represents the audio data, such as without the generation and/or use of text data. The intent data may indicate a determined intent associated with the user utterance as well as a payload and/or value associated with the intent. For example, for a user utterance of "turn on Light A," the NLU component 142 may identify a "turn on" intent and the payload may be "Light A." In this example where the intent data indicates an intent to operate a device with a naming indicator of "Light A," the speech-processing system 124 may call one or more speechlets to effectuate the intent. Speechlets, as described herein may otherwise be described as applications and may include functionality for utilizing intent data to generate directives and/or instructions. For example, a communications speechlet may be called when the intent indicates that an action is to be performed associated with establishing a communication channel with another device. The speechlet may be designated as being configured to handle the intent of establishing a communication channel, for example. The speechlet may receive the intent data and/or other data associated with the user utterance from the NLU component 142, such as by an orchestrator of the remote system 104, and may perform operations to instruct the device 102 to perform an operation. For example, a shopping speechlet may retrieve a user profile associated with the request may cause the item to be purchased utilizing purchasing information associated with the user profile. The remote system 104 may generate audio data confirming that a communication channel has been established, such as by a text-to-speech component. The audio data may be sent from the remote system 104 to the device 102 for output of corresponding audio by the speakers 116 of the device 102.

The additional components of the electronic device 102 and the remote system 104 will now be described below by way of example. The electronic devices 102 may receive data from one or more other devices associated with the environment. For example, data indicating the state of the one or more devices, data indicating that a mobile device is in proximity to a given electronic device 102 such that the devices are in wireless communication with each other over a short-range communication network, data indicating the detection of movement in the environment, data indicating that an acoustic-event detection component of the electronic device 102 has identified an acoustic event, and/or other data such as naming indicators of the devices may be received and/or determined. This data may be generated and stored for electronic devices 102 associated with a given environment and/or for multiple electronic devices associated with multiple disparate environments. The electronic devices 102 and/or the remote system 104 may generate and store this data, which may be utilized to generate and/or train models for determining the activity state associated with a given user profile. It should be understood that while examples of such event data are provided herein, those examples are not by way of limitation. Instead, the event data received from the electronic devices 102 may include any data that may indicate a state of the electronic devices 102, other devices, and/or the environment.

The event data may be sent to the remote system 104, which may store the event data in one or more databases, such as the user registry 126 and/or the datastores 128. The user registry 126 may store event data associated with one or more user accounts associated with the electronic devices 102 associated with the event data. The datastores 128 may store event data in a manner that does not necessarily associate that event data with the electronic device 102 from which the event data was received. The event data may be made available to one or more components of the remote system 104 for smart home activity modeling as described herein.

For example, the one or more training models 130 may be generated and be configured to accept the event data, and/or a formatted version of the event data from the user registry 126 and/or datastores 128 and perform an analysis of the event data that includes labelling the event data with one or more indicators of an activity state. For example, the training models 130 may include a supervised machine-learning model that has been configured to apply one or more rules to given events to label those events with an activity state. For example, event data indicating that a light has been turned on may be labeled by the supervised machine-learning model as being associated with an active state, as opposed to an asleep state or an away state. The supervised machine-learning model may generate a training dataset that includes the event data and the labeling data associated with the event data. The training dataset may be stored in association with the training database 132. Additionally, in examples, one or more of the electronic devices 102 and/or user profiles associated with the electronic devices 102 may be predetermined to be included in an evaluation dataset, which may also be stored in association with the training database 132. For example, certain devices may have sensors 122 that are better suited for determining activity states and/or use of devices by given user profiles may be considered more beneficial for accurately determining activity states. In these examples, a portion of the event data corresponding to the predetermined electronic devices 102 and/or user profiles may be input into a separate supervised machine-learning model to generate the evaluation dataset. The evaluation dataset may represent a smaller subset of the event data utilized to generate the training dataset. The evaluation dataset may be utilized by other models, as described more fully below, to test or otherwise determine the accuracy of the labeling associated with the training dataset.

The training models 130 may also include a neural network model, which may be configured to accept the evaluation dataset and/or the training dataset from the supervised machine-learning models to generate and/or train one or more activity models 134. For example, the neural network model may represent a more robust machine-learning model than the supervised machine-learning models described herein. The neural network model may utilize the event data and the labeling data to identify events indicative of electronic devices 102 and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network may "learn" how certain events, such as for certain electronic devices 102 and/or environments, impact determining activity states.

The activity models 134 generated and/or trained utilizing the neural network model may include one or more activity models 134 that are configured to accept event data and generate, as output, results indicating that given event data corresponds to a given activity state and, in examples, a confidence associated with the activity state determination. The activity models 134 may include a historical-activity model, which may be configured to determine an activity state associated with historical events associated with an electronic device 102 and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week ago a given environment was associated with an asleep state based at least in part on the event data associated with that given time.

The activity models 134 may also include a current-activity model, which may be configured to determine an activity state associated with a live or near-live event associated with an electronic device and/or environment. For example, the current-activity model may be configured to accept, as features to the current-activity model, event data corresponding to live events and/or near-live events. In examples, use of the current-activity model may be in association with the electronic device 102 and/or the remote system 104 causing one or more sensors 122 or other components of the electronic device 102 to generate live or near-live event data to be utilized by the current-activity model. The current-activity model may generate, as output, data indicating that a given live or near-live event corresponds to a given activity state. For example, the current-activity model may be utilized to determine that at a current time a given environment is associated with an active state based at least in part on event data associated with the current time. In examples, the current-activity model may be trained based at least in part on the output from the neural network model and/or from the output of the historical-activity model.

The activity models 134 may also include a future-activity model, which may be configured to predict an activity state associated with events that may occur in the future associated with an electronic device 102 and/or environment. For example, the future-activity model may be configured to accept, as features to the future-activity model, event data corresponding to the historical events and/or live or near-live events. The future-activity model may generate, as output, data indicating that a given event that is likely to occur at a given time in the future is likely to correspond to a given activity state. For example, the future-activity model may be utilized to determine that at a given time a week from now a given environment is likely to be associated with an away state based at least in part on historical event data and/or current event data associated with the given environment. In examples, the future-activity model may be trained based at least in part on the output from the neural network model and/or from the output of the historical-activity model and/or the current-activity model.

The activity models 134 may be made available to the one or more applications 136 associated with the remote system 104 and/or one or more other systems. For example, one or more applications 136 may be able to utilize activity state determinations to generate more accurate results and/or to determine when to perform certain operations, such as when to generate and/or send a notification and/or recommendation, when to operate a device, when to transition a state of a device, etc. In these examples, one or more of the applications 136 may send request data to the activity models 134 for an indication of an activity of a device and/or environment in the past, now, or in the future. In some examples, the request data may indicate which of the activity models 134 are to be utilized for determining the activity state. In other examples, the request data may provide an indication of which events the application 136 would like to determine the activity state for, and the remote system 104 may determine which of the activity models 134 to utilize to provide results relevant to those events. The selected activity model 134 may then query the user registry 126 and/or datastores 128 for the event data relevant to the request from the application 136 and utilize, as input to the selected activity model 134, features corresponding to the event data. The selected activity model 134 may output data indicating the determined activity state for the device and/or environment at issue and, in examples, a confidence value associated with the determined activity state. The application 136 that sent the request data may then utilize the activity state as determined by the selected activity model 134 to perform one or more actions, such as the sending of a recommendation and/or the operation of a device, for example.

Additionally, in examples, the one or more applications 136 may be configured to cause one or more indications of the determined activity state to be presented. For example, a command may be sent to a voice-enabled device 102 to cause a lighting element 118 of the voice-enabled device 102 to emit light indicating the state of the device associated with the activity state. For example, the lighting element 118 may be caused to emit orange light when the device 102 is in a state associated with an away activity state. In other examples, text data may be sent to a user device and the command may cause corresponding text to be displayed indicating the device state. In examples, users of such devices may provide user input indicating that the device is accurately or inaccurately in the indicated state. User input data corresponding to this user input may be sent from the device to the feedback component 138. The feedback component 138 may be configured to receive the user input data and utilize the user input data to train one or more of the models 130, such as the supervised machine-learning models and/or the neural network model. By so doing, the feedback component 138 may generate a positive dataset, in situations where the user input indicates accurate activity state determinations, indicating an approximated ground truth that the events associated with a given activity state determination were in fact associated with the determined activity state. The feedback component 138 may also generate a negative dataset, in situations where the user input indicates inaccurate activity state determinations, indicating that the events associated with that activity state determination were not associated with the determined activity state.

By utilizing the activity models 134 described above, the applications 136 may utilize activity state determinations to determine when and/or how to send recommendations, when to cause certain devices to transition to certain modes, and/or when to perform other actions associated with the devices. For example, a given application 136 may be configured to detect anomalies in user behavior when a device is configured to generate sensor data associated with user movement, such as when a user has requested that such data be generated in an aging-in-place situation. The application 136 may utilize one or more signals to detect such anomalies, such as user movement patterns, acoustic-event detection determinations, etc. The application 136, utilizing the techniques described herein, may also utilize the activity models 134 to more accurately identify historic events associated with the device that may be utilized to compare with current events for anomaly detection. For example, the application 136 may be able to utilize events the correspond only to events that occurred during an awake state for detecting anomalies when the environment is currently associated with an awake state. By so doing, the applications 136 may utilize the determined activity states as described herein to more accurately determine which data to utilize for making application-specific determinations, and/or to increase relevant features to be utilized for making such application-specific determinations.

In additional examples, the activity-based determinations described herein may be utilized to determine what recommendation to provide to a user device 102 and/or when to send such a recommendation. For example, device-usage data may be utilized by a remote system 104 to determine when a recommendation is to be surfaced to a user device 102. By way of example, a given device 102 may be associated with a given device-usage pattern. That device-usage pattern may indicate when a device 102 is operated, how the device 102 is operated, and/or details associated with the device 102, such as a naming indicator associated with the device 102 and/or the device type of the device 102, etc. This information may be utilized to determine when a recommendation or otherwise a "hunch" is to be surfaced to a user device 102. The recommendations may include requests to operate the device in a certain way, to change information associated with the device 102, to add the device 102 to a device group, to add the device 102 to a device routine, etc. In addition to utilizing the device-usage data to determine when and how to surface such recommendations, the activity-based determinations described herein may also be used to determine when and how to surface recommendations.

For example, when the activity model(s) 134 described herein determine that a given device 102 and/or environment is associated with an active state, the recommendations may be provided to a device 102 within the environment for output by the device 102 because a user is currently in that environment and is moving in a manner associated with an active state. In other examples, such as when the environment is associated with an asleep state, the recommendation may not be output by the device 102 because a user is not currently active in the environment, but instead the recommendation may be provided to a user device 102 by way of a message that may be viewed by the user at a later time. In addition to utilizing activity-based determinations to determine when and how to provide a recommendation, the activity-based determinations may also be utilized to determine what recommendation to provide. For example, when a device 102 is associated with an away state and the device-usage data indicates that a smart door lock is typically locked but in this instance the smart door lock is in an unlocked state, the system may utilize both the device-usage data and the indication that the environment is associated with an away state to surface a recommendation to cause the smart door lock to transition to a locked state. In still other examples, the activity-based determinations may be utilized to determine whether to send a recommendation or whether to perform an action without sending a recommendation and instead, in examples, send a notification that the action has been taken. For example, if an environment is associated with an asleep state, indicating that a user is present but is not active, instead of surfacing a recommendation to lock a smart door lock that is typically in a lock state but is currently in an unlocked state, the system 104 may cause the device to transition to the locked state and provide a notification of the action to a user device 102.

It should be understood that, in examples, an inactive state may include an away state and/or an asleep state. In an away state, presence of a user may not be detected in an environment associated with one or more sensors configured to detect presence. In an asleep state, presence of the user may be detected, but the user may not be moving or may otherwise not be interacting with the environment, such as by providing commands for devices to perform operations. This is in contrast to an active state, where presence of the user is detected and the user is moving or otherwise is interacting with the environment, such as by walking, talking, changing positions, and/or giving commands, for example. The system 100 may determine that user profile data is associated with an active state when one or more signals, such as from smart-home devices or otherwise accessory devices, are received that indicate that a user associated with the user profile data is present and is engaged in an activity in the environment. The one or more signals may include, for example, device-beacon data received from a user device associated with the user that indicates the device is in the environment and that the device is moving. The one or more signals may also include, for example, data indicating interaction of the user with a voice user interface, such as a voice user interface associated with a voice-enabled device. The one or more signals may also include, for example, data indicating that a wake word has been detected, such as by a voice-enabled device. The one or more signals may also include, for example, receipt of user input data requesting operation of a device in the environment. The one or more signals may also include, for example, data indicating that a smart-home device is being operated and/or that another device is being operated and a smart-home device or other device having sensors described herein has detected operation of the smart-home device. Such operations may include, for example, turning lights on and/or off, turning appliances on and/or off from the appliances themselves as opposed to from an application running on a mobile user device, a wireless router device or other network access point receiving data indicating a SSID of a personal device of a user and an indication that such a device is sending data, motion sensor data, ambient noise detection, acoustic event detections, etc.

Additionally, for the inactive states, such as the away state or the asleep state, the one or more signals may include the same or similar signals as described above, but where those signals indicate that users are absent from the environment, or that users are present but are asleep. For example, when no device-beaconing data is received, such an occurrence indicates that no mobile personal devices are within the environment, which may be utilized to determine that user profile data is associated with an away mode. Other examples where the signals indicate that user profile data is associated with an away mode include ambient noise satisfying a threshold noise value indicating an environment is emitting only typical ambient background noise. Other indications may include the lack of interaction with smart-home devices, such as for at least a threshold period of time. The one or more signals may also indicate an asleep state in instances where the signals indicate that a user is present, such as from device-beaconing data, but the signals otherwise indicate an inactive state, such as from data indicating a lack of interaction with smart-home devices, a lack of acoustic event detection for events such as footsteps, the lack of detection of user speech from audio data captured by a microphone in the environment, etc. Additionally, the one or more sensors may be configured to detect noises and/or posture indicating an asleep state. For example, breathing and/or snoring may be audible and may be detected from audio data captured from the environment. In further examples, radar-based sensors, such as ultrasonic sensors, may be configured to determine, when user consent has been provided to collect such data, a location of a user, which may indicate that a user is in a sleeping position. Additionally, in examples where the sensors are included in a smart bed, or other object associated with sleeping, signals from those sensors, such as an indication that someone is on the bed, may be utilized. Additionally, contextual data such as the time of day, day of the week, and/or historical data indicating when user profile data is associated with an asleep state may be utilized. For example, it may be more likely that user profile data is associated with an asleep state during the nighttime, such as on a weeknight. Some or all of this information may be utilized to determine that user profile data is associated with an asleep state.

It should be understood that while examples provided herein are associated with devices having sensors that are situated in a home type environment, devices with sensors situated in other types of environments, such as offices, vehicles, outdoors, etc. are also included. Some or all of the sensors described herein may be utilized in these examples to determine an activity state associated with those environments.

The models 130, 134 described herein may utilize predictive analytics to predict one or more outcomes. Predictive analytic techniques may include, for example, predictive modelling, machine learning, and/or data mining. Generally, predictive modelling may utilize statistics to predict outcomes. Machine learning, while also utilizing statistical techniques, may provide the ability to improve outcome prediction performance without being explicitly programmed to do so. A number of machine learning techniques may be employed to generate and/or modify the models describes herein. Those techniques may include, for example, decision tree learning, association rule learning, artificial neural networks (including, in examples, deep learning), inductive logic programming, support vector machines, clustering, Bayesian networks, reinforcement learning, representation learning, similarity and metric learning, sparse dictionary learning, and/or rules-based machine learning.

Information from stored and/or accessible data may be extracted from one or more databases and may be utilized to predict trends and behavior patterns. In examples, the event, otherwise described herein as an outcome, may be an event that will occur in the future, such as whether presence will be detected. The predictive analytic techniques may be utilized to determine associations and/or relationships between explanatory variables and predicted variables from past occurrences and utilizing these variables to predict the unknown outcome. The predictive analytic techniques may include defining the outcome and data sets used to predict the outcome. Then, data may be collected and/or accessed to be used for analysis.

Data analysis may include using one or more models 130, 134, including for example one or more algorithms, to inspect the data with the goal of identifying useful information and arriving at one or more determinations that assist in predicting the outcome of interest. One or more validation operations may be performed, such as using statistical analysis techniques, to validate accuracy of the models 130, 134. Thereafter, predictive modelling may be performed to generate accurate predictive models for future events. Outcome prediction may be deterministic such that the outcome is determined to occur or not occur. Additionally, or alternatively, the outcome prediction may be probabilistic such that the outcome is determined to occur to a certain probability and/or confidence.

It should be noted that while text data is described as a type of data utilized to communicate between various components of the remote system 104 and/or other systems and/or devices, the components of the remote system 104 may use any suitable format of data to communicate. For example, the data may be in a human-readable format, such as text data formatted as XML, SSML, and/or other markup language, or in a computer-readable format, such as binary, hexadecimal, etc., which may be converted to text data for display by one or more devices such as the devices 102.

As shown in FIG. 1, several of the components of the remote system 104 and the associated functionality of those components as described herein may be performed by one or more of the electronic devices 102 and/or personal devices. Additionally, or alternatively, some or all of the components and/or functionalities associated with the electronic devices 102 and/or personal devices may be performed by the remote system 104.

It should be noted that the exchange of data and/or information as described herein may be performed only in situations where a user has provided consent for the exchange of such information. For example, upon setup of devices and/or initiation of applications, a user may be provided with the opportunity to opt in and/or opt out of data exchanges between devices and/or for performance of the functionalities described herein. Additionally, when one of the devices is associated with a first user account and another of the devices is associated with a second user account, user consent may be obtained before performing some, any, or all of the operations and/or processes described herein. Additionally, the operations performed by the components of the systems described herein may be performed only in situations where a user has provided consent for performance of the operations.

As used herein, a processor, such as processor(s) 108 and/or the processor(s) described with respect to the components of the remote system 104, may include multiple processors and/or a processor having multiple cores. Further, the processors may comprise one or more cores of different types. For example, the processors may include application processor units, graphic processing units, and so forth. In one implementation, the processor may comprise a microcontroller and/or a microprocessor. The processor(s) 108 and/or the processor(s) described with respect to the components of the remote system 104 may include a graphics processing unit (GPU), a microprocessor, a digital signal processor or other processing units or components known in the art. Alternatively, or in addition, the functionally described herein can be performed, at least in part, by one or more hardware logic components. For example, and without limitation, illustrative types of hardware logic components that can be used include field-programmable gate arrays (FPGAs), application-specific integrated circuits (ASICs), application-specific standard products (ASSPs), system-on-a-chip systems (SOCs), complex programmable logic devices (CPLDs), etc. Additionally, each of the processor(s) 110 and/or the processor(s) described with respect to the components of the remote system 106 may possess its own local memory, which also may store program components, program data, and/or one or more operating systems.

The memory 112 and/or the memory described with respect to the components of the remote system 104 may include volatile and nonvolatile memory, removable and non-removable media implemented in any method or technology for storage of information, such as computer-readable instructions, data structures, program component, or other data. Such memory 112 and/or the memory described with respect to the components of the remote system 104 includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information and which can be accessed by a computing device. The memory 112 and/or the memory described with respect to the components of the remote system 104 may be implemented as computer-readable storage media ("CRSM"), which may be any available physical media accessible by the processor(s) 108 and/or the processor(s) described with respect to the remote system 104 to execute instructions stored on the memory 112 and/or the memory described with respect to the components of the remote system 104. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other tangible medium which can be used to store the desired information and which can be accessed by the processor(s).

Further, functional components may be stored in the respective memories, or the same functionality may alternatively be implemented in hardware, firmware, application specific integrated circuits, field programmable gate arrays, or as a system on a chip (SoC). In addition, while not illustrated, each respective memory, such as memory 112 and/or the memory described with respect to the components of the remote system 104, discussed herein may include at least one operating system (OS) component that is configured to manage hardware resource devices such as the network interface(s), the I/O devices of the respective apparatuses, and so forth, and provide various services to applications or components executing on the processors. Such OS component may implement a variant of the FreeBSD operating system as promulgated by the FreeBSD Project; other UNIX or UNIX-like variants; a variation of the Linux operating system as promulgated by Linus Torvalds; the FireOS operating system from Amazon.com Inc. of Seattle, Washington, USA; the Windows operating system from Microsoft Corporation of Redmond, Washington, USA; LynxOS as promulgated by Lynx Software Technologies, Inc. of San Jose, California; Operating System Embedded (Enea OSE) as promulgated by ENEA AB of Sweden; and so forth.

The network interface(s) 110 and/or the network interface(s) described with respect to the components of the remote system 104 may enable messages between the components and/or devices shown in system 100 and/or with one or more other polling systems, as well as other networked devices. Such network interface(s) 110 and/or the network interface(s) described with respect to the components of the remote system 104 may include one or more network interface controllers (NICs) or other types of transceiver devices to send and receive messages over the network 106.

For instance, each of the network interface(s) 110 and/or the network interface(s) described with respect to the components of the remote system 104 may include a personal area network (PAN) component to enable messages over one or more short-range wireless message channels. For instance, the PAN component may enable messages compliant with at least one of the following standards IEEE 802.15.4 (ZigBee), IEEE 802.15.1 (Bluetooth), IEEE 802.11 (WiFi), or any other PAN message protocol. Furthermore, each of the network interface(s) 110 and/or the network interface(s) described with respect to the components of the remote system 104 may include a wide area network (WAN) component to enable message over a wide area network.

In some instances, the remote system 104 may be local to an environment associated the electronic devices 102 and/or personal devices. For instance, the remote system 104 may be located within one or more of the electronic devices 102 and/or personal devices. In some instances, some or all of the functionality of the remote system 104 may be performed by one or more of the electronic devices 102 and/or personal devices. Also, while various components of the remote system 104 have been labeled and named in this disclosure and each component has been described as being configured to cause the processor(s) to perform certain operations, it should be understood that the described operations may be performed by some or all of the components and/or other components not specifically illustrated. It should be understood that, in addition to the above, some or all of the operations described herein may be performed on a phone or other mobile device and/or on a device local to the environment, such as, for example, a hub device in a home and/or office environment, a self-driving automobile, a bus, an airplane, a camper, a trailer, and/or other similar object having a computer to perform its own sensor processing, etc.

Figure 2:
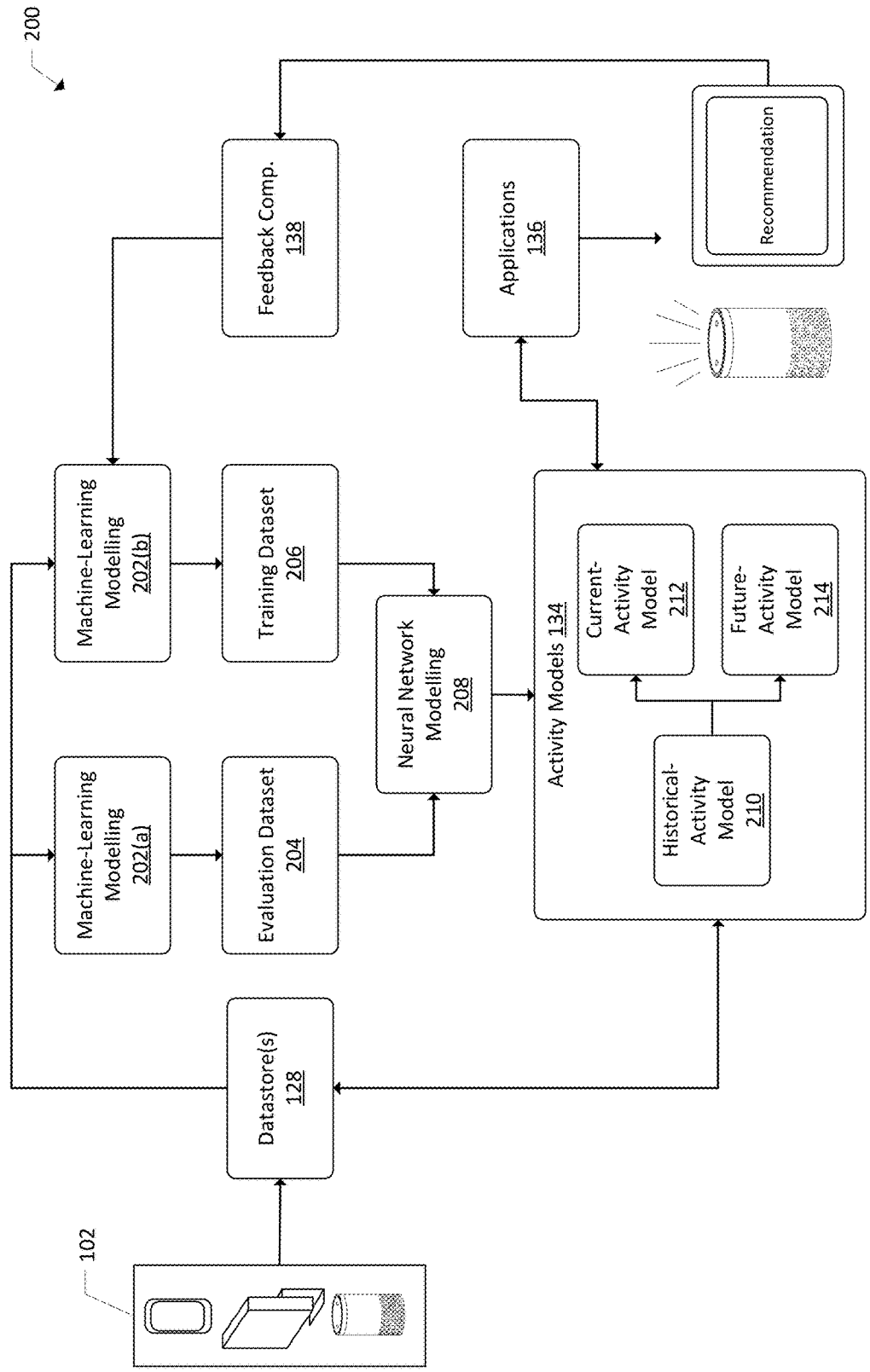
FIG. 2 illustrates a conceptual diagram of components of a system for training models for activity-based device recommendations.

FIG. 2 illustrates a conceptual diagram of components of a system 200 for training models for smart home activity modeling. The system 200 may include components that are similar to those described with respect to FIG. 1. For example, the system 200 may include one or more datastores 128, one or more activity models 134, one or more applications 136, and/or one or more feedback components 138. The electronic devices 102 described with respect to FIG. 1 may also be the same or similar to the electronic devices 102 described in FIG. 2. The system 200 may also include components and/or operations such as machine-learning modelling 202(*a*)-(*b*), an evaluation dataset 204, a training dataset 206, neural network modelling 208, a historical-activity model 210, a current-activity model 212, and/or a future-activity model 214, all of which will be described below.

For example, the electronic devices 102 may receive data from one or more other devices associated with the environment. For example, data indicating the state of the one or more devices, data indicating that a mobile device is in proximity to a given electronic device 102 such that the devices are in wireless communication with each other over a short-range communication network, data indicating the detection of movement in the environment, data indicating that an acoustic-event detection component of the electronic device 102 has identified an acoustic event, and/or other data such as naming indicators of the devices may be received and/or determined. This data may be generated and stored for electronic devices 102 associated with a given environment and/or for multiple electronic devices associated with multiple disparate environments. The electronic devices 102 and/or a remote system may generate and store this data, which may be utilized to generate and/or train models for determining the activity state associated with a given user profile. It should be understood that while examples of such event data are provided herein, those examples are not by way of limitation. Instead, the event data received from the electronic devices 102 may include any data that may indicate a state of the electronic devices 102, other devices, and/or the environment.

The event data may be sent to the remote system, which may store the event data in one or more databases, such as the datastores 128. The event data may be made available to one or more components of the remote system for smart home activity modeling as described herein. For example, the machine-learning modelling 202(*a*)-(*b*) may be utilized to accept the event data, and/or a formatted version of the event data from the datastores 128 and perform an analysis of the event data that includes labelling the event data with one or more indicators of an activity state. For example, machine-learning models may be configured to apply one or more rules to given events to label those events with an activity state. For example, event data indicating that a light has been turned on may be labeled by the machine-learning models as being associated with an active state, as opposed to an asleep state or an away state. A first machine-learning model may generate the training dataset 206 that includes the event data and the labeling data associated with the event data. The training dataset 206 may be stored in association with a training database. Additionally, in examples, one or more of the electronic devices 102 and/or user profiles associated with the electronic devices 102 may be predetermined to be included in the evaluation dataset 204, which may also be stored in association with the training database. For example, certain devices may have sensors that are better suited for determining activity states and/or use of devices by given user profiles may be considered more beneficial for accurately determining activity states. In these examples, a portion of the event data corresponding to the predetermined electronic devices 102 and/or user profiles may be input into the separate machine-learning model to generate the evaluation dataset 204. The evaluation dataset 204 may represent a smaller subset of the event data utilized to generate the training dataset 206. The evaluation dataset 204 may be utilized by other models, as described more fully below, to test or otherwise determine the accuracy of the labeling associated with the training dataset 206.

The neural network modelling 208 may include accepting the evaluation dataset 204 and/or the training dataset 206 from the machine-learning models to generate and/or train one or more activity models 134. For example, the neural network modelling may represent a more robust machine-learning model than the machine-learning models utilized for machine-learning modelling 202(*a*)-(*b*) described herein. The neural network model may utilize the event data and the labeling data to identify events indicative of electronic devices 102 and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the machine-learning models that impact identification of activity state. By so doing, the neural network model may "learn" how certain events, such as for certain electronic devices 102 and/or environments, impact determining activity states.

The activity models 134 generated and/or trained utilizing the neural network model may include one or more activity models 134 that are configured to accept event data and generate, as output, results indicating that given event data corresponds to a given activity state and, in examples, a confidence associated with the activity state determination. The activity models 134 may include the historical-activity model 210, which may be configured to determine an activity state associated with historical events associated with an electronic device 102 and/or environment. For example, the historical-activity model 210 may be configured to accept, as features to the historical-activity model 210, event data corresponding to historical events. The historical-activity model 210 may generate, as output, data indicating that a given historical event corresponded to a given activity state. For example, the historical-activity model 210 may be utilized to determine that a given time a week ago a given environment was associated with an asleep state based at least in part on the event data associated with that given time.

The activity models 134 may also include the current-activity model 212, which may be configured to determine an activity state associated with a live or near-live event associated with an electronic device 102 and/or environment. For example, the current-activity model 212 may be configured to accept, as features to the current-activity model 212, event data corresponding to live events and/or near-live events. In examples, use of the current-activity model 212 may be in association with the electronic device 102 and/or the remote system causing one or more sensors or other components of the electronic device 102 to generate live or near-live event data to be utilized by the current-activity model 212. The current-activity model 212 may generate, as output, data indicating that a given live or near-live event corresponds to a given activity state. For example, the current-activity model 212 may be utilized to determine that at a current time a given environment is associated with an active state based at least in part on event data associated with the current time. In examples, the current-activity model 212 may be trained based at least in part on the output from the neural network model and/or from the output of the historical-activity model 210.

The activity models 134 may also include the future-activity model 214, which may be configured to predict an activity state associated with events that may occur in the future associated with an electronic device 102 and/or environment. For example, the future-activity model 214 may be configured to accept, as features to the future-activity model 214, event data corresponding to the historical events and/or live or near-live events. The future-activity model 214 may generate, as output, data indicating that a given event that is likely to occur at a given time in the future is likely to correspond to a given activity state. For example, the future-activity model 214 may be utilized to determine that at a given time a week from now a given environment is likely to be associated with an away state based at least in part on historical event data and/or current event data associated with the given environment. In examples, the future-activity model 214 may be trained based at least in part on the output from the neural network model and/or from the output of the historical-activity model 210 and/or the current-activity model 212.

The activity models 134 may be made available to the one or more applications 136 associated with the remote system and/or one or more other systems. For example, the one or more applications 136 may be able to utilize activity state determinations to generate more accurate results and/or to determine when to perform certain operations, such as when to generate and/or send a notification and/or recommendation, when to operate a device, when to transition a state of a device, etc. In these examples, one or more of the applications 136 may send request data to the activity models 134 for an indication of an activity of a device and/or environment in the past, now, or in the future. In some examples, the request data may indicate which of the activity models 134 are to be utilized for determining the activity state. In other examples, the request data may provide an indication of which events the application 136 would like to determine the activity state for, and the remote system may determine which of the activity models 134 to utilize to provide results relevant to those events. The selected activity model 134 may then query the datastores 128 for the event data relevant to the request from the application 136 and utilize, as input to the selected activity model 134, features corresponding to the event data. The selected activity model 134 may output data indicating the determined activity state for the device and/or environment at issue and, in examples, a confidence value associated with the determined activity state. The application 136 that sent the request data may then utilize the activity state as determined by the selected activity model 134 to perform one or more actions, such as the sending of a recommendation and/or the operation of a device, for example.

Additionally, in examples, the one or more applications 136 may be configured to cause one or more indications of the determined activity state to be presented. For example, a command may be sent to a voice-enabled device 102 to cause a lighting element of the voice-enabled device 102 to emit light indicating the state of the device associated with the activity state. For example, the lighting element may be caused to emit orange light when a user profile is in a state associated with an away activity state. In other examples, text data may be sent to a user device and the command may cause corresponding text to be displayed indicating the device state. In examples, users of such devices may provide user input indicating that the device is accurately or inaccurately in the indicated state. User input data corresponding to this user input may be sent from the device to the feedback component 138. The feedback component 138 may be configured to receive the user input data and utilize the user input data to train one or more of the machine-learning models and/or the neural network model. By so doing, the feedback component 138 may generate a positive dataset, in situations where the user input indicates accurate activity state determinations, indicating an approximated ground truth that the events associated with a given activity state determination were in fact associated with the determined activity state. The feedback component 138 may also generate a negative dataset, in situations where the user input indicates inaccurate activity state determinations, indicating that the events associated with that activity state determination were not associated with the determined activity state.

By utilizing the activity models 134 described above, the applications 136 may utilize activity state determinations to determine when and/or how to send recommendations, when to cause certain devices to transition to certain modes, and/or when to perform other actions associated with the devices. For example, a given application 136 may be configured to detect anomalies in user behavior when a device is configured to generate sensor data associated with user movement, such as when a user has requested that such data be generated in an aging-in-place situation. The application 136 may utilize one or more signals to detect such anomalies, such as user movement patterns, acoustic-event detection determinations, etc. The application 136, utilizing the techniques described herein, may also utilize the activity models 134 to more accurately identify historic events associated with the device that may be utilized to compare with current events for anomaly detection. For example, the application 136 may be able to utilize events the correspond only to events that occurred during an awake state for detecting anomalies when the environment is currently associated with an awake state. By so doing, the applications 136 may utilize the determined activity states as described herein to more accurately determine which data to utilize for making application-specific determinations, and/or to increase relevant features to be utilized for making such application-specific determinations.

In additional examples, the activity-based determinations described herein may be utilized to determine what recommendation to provide to a user device 102 and/or when to send such a recommendation. For example, device-usage data may be utilized by a remote system 104 to determine when a recommendation is to be surfaced to a user device 102. By way of example, a given device 102 may be associated with a given device-usage pattern. That device-usage pattern may indicate when a device 102 is operated, how the device 102 is operated, and/or details associated with the device 102, such as a naming indicator associated with the device 102 and/or the device type of the device 102, etc. This information may be utilized to determine when a recommendation or otherwise a "hunch" is to be surfaced to a user device 102. The recommendations may include requests to operate the device in a certain way, to change information associated with the device 102, to add the device 102 to a device group, to add the device 102 to a device routine, etc. In addition to utilizing the device-usage data to determine when and how to surface such recommendations, the activity-based determinations described herein may also be used to determine when and how to surface recommendations.

For example, when the activity model(s) 134 described herein determine that a given device 102 and/or environment is associated with an active state, the recommendations may be provided to a device 102 within the environment for output by the device 102 because a user is currently in that environment and is moving in a manner associated with an active state. In other examples, such as when the environment is associated with an asleep state, the recommendation may not be output by the device 102 because a user is not currently active in the environment, but instead the recommendation may be provided to a user device 102 by way of a message that may be viewed by the user at a later time. In addition to utilizing activity-based determinations to determine when and how to provide a recommendation, the activity-based determinations may also be utilized to determine what recommendation to provide. For example, when a device 102 is associated with an away state and the device-usage data indicates that a smart door lock is typically locked but in this instance the smart door lock is in an unlocked state, the system may utilize both the device-usage data and the indication that the environment is associated with an away state to surface a recommendation to cause the smart door lock to transition to a locked state. In still other examples, the activity-based determinations may be utilized to determine whether to send a recommendation or whether to perform an action without sending a recommendation and instead, in examples, send a notification that the action has been taken. For example, if an environment is associated with an asleep state, indicating that a user is present but is not active, instead of surfacing a recommendation to lock a smart door lock that is typically in a lock state but is currently in an unlocked state, the system 104 may cause the device to transition to the locked state and provide a notification of the action to a user device 102.

Figure 3:
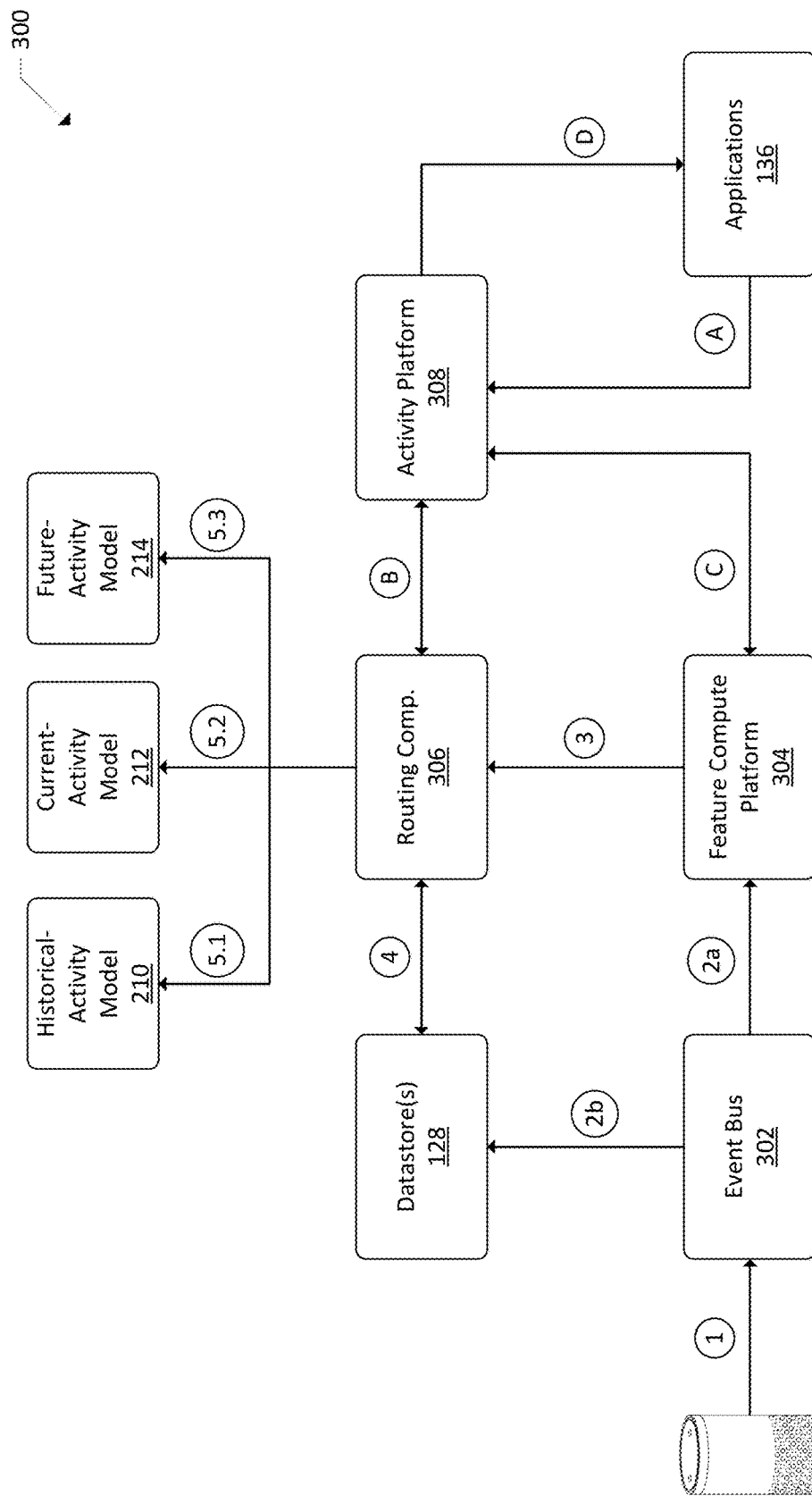
FIG. 3 illustrates a conceptual diagram of components of a system for utilizing activity models to determine an activity state associated with a given environment.

FIG. 3 illustrates a conceptual diagram of components of a system 300 for utilizing smart home activity models to determine an activity state associated with a given environment. The system 300 may include components described with respect to FIGS. 1 and 2, such as one or more datastores 128, one or more applications 136, a historical-activity model 210, a current-activity model 212, and/or a future-activity model 214. The system 300 may also include one or more components such as an event bus 302, a feature compute platform 304, a routing component 306, and/or an activity platform 308. Each of these components will be described in detail below with respect to steps 1-5.3 and steps A-D. It should be understood that while FIG. 3 is described utilizing these steps, the operations described below may be performed in that order or a different order.

At step 1, one or more electronic devices 102 may generate and/or send event data to a remote system. For example, data indicating the state of the one or more devices, data indicating that a mobile device is in proximity to a given electronic device 102 such that the devices are in wireless communication with each other over a short-range communication network, data indicating the detection of movement in the environment, data indicating that an acoustic-event detection component of the electronic device 102 has identified an acoustic event, and/or other data such as naming indicators of the devices may be received and/or determined. This data may be generated and stored for electronic devices 102 associated with a given environment and/or for multiple electronic devices associated with multiple disparate environments. The electronic devices 102 and/or a remote system may generate and store this data, which may be utilized to generate and/or train models for determining the activity state associated with a given user profile. It should be understood that while examples of such event data are provided herein, those examples are not by way of limitation. Instead, the event data received from the electronic devices 102 may include any data that may indicate a state of the electronic devices 102, other devices, and/or the environment.

At step 2a, an event bus 302 may receive the event data and may determine to send the event data to the feature compute platform 304. For example, data of different types and/or containing different content may be received by the event bus 302. The event bus 302 may be configured to identify certain data as event data that may be relevant to activity state determination and may be configured to send such identified data to the feature compute platform 304 for further processing. Additionally, at step 2b, the event bus 302 may send the event data to the datastore(s) 128, which may store the event data for later use by the system 200.

At step 3, the feature compute platform 304 may format the event data or otherwise generate feature data corresponding to the event data that represents the event data as one or more features configured for input into one or more activity models. For example, each of the activity models may be configured to receive certain features and/or data that is formatted in a given manner. The feature compute platform 304 may be configured to receive the raw event data and generate feature data that is useable by the activity models for determining activity states.

At step 4, the routing component 306 may determine to send the feature data to the datastores 128 for storage and use by the one or more activity models for training, testing, and/or activity state determination. For example, depending on the nature of the feature data, the feature data may not be designated for use in training the activity models but may be relevant for the activity models to utilize for determining activity states. In these examples, the feature data may be sent to the datastores 128. In other examples, the feature data may be designed for a training dataset and/or an evaluation dataset, and in these examples the feature data may be provided to the activity models for use in training and/or testing the accuracy of the activity models for determining activity states.

At step 5.1, the routing component 306 may query the datastores 128 for feature data designated for the historical-activity model 210 and may send the feature data to the historical-activity model 210. The historical-activity model 210 may accept the feature data from the routing component 306 and the historical-activity model 210 may be trained utilizing the feature data. Training of the historical-activity model 210 may include determining which features are to be utilized for determining activity states and weighting of those features.

Alternatively, at step 5.2, the routing component 306 may query the datastores 128 for feature data designated for the current-activity model 212 and may send the feature data to the current-activity model 212. The current-activity model 212 may accept the feature data from the routing component 306 and the current-activity model 212 may be trained utilizing the feature data. Training of the current-activity model 212 may include determining which features are to be utilized for determining activity states and weighting of those features.

Alternatively, at step 5.3, the routing component 306 may query the datastores 128 for feature data designated for the future-activity model 214 and may send the feature data to the future-activity model 214. The future-activity model 214 may accept the feature data from the routing component 306 and the future-activity model 214 may be trained utilizing the feature data. Training of the future-activity model 214 may include determining which features are to be utilized for determining activity states and weighting of those features.

At step A, the one or more applications 136 may send request data for utilizing the activity models to determine an activity state associated with a user profile and/or an environment. The request data may be received by the activity platform 308. For example, the one or more applications 136 may be able to utilize activity state determinations to generate more accurate results and/or to determine when to perform certain operations, such as when to generate and/or send a notification and/or recommendation, when to operate a device, when to transition a state of a device, etc. In these examples, one or more of the applications 136 may send request data to the activity models for an indication of an activity of a device and/or environment in the past, now, or in the future. In some examples, the request data may indicate which of the activity models are to be utilized for determining the activity state. In other examples, the request data may provide an indication of which events the application 136 would like to determine the activity state for, and the remote system may determine which of the activity models to utilize to provide results relevant to those events.

At step B, the activity platform 308 may send a command to the routing component 306 requesting utilization of one or more of the activity models to determine the requested activity state. The routing component 306 may query the datastores for feature data relevant to the request and may send a command to a selected activity model to utilize the feature data for determining the requested activity state.

In some examples, at step C, the activity platform 308 may also request the event data and/or the feature data itself for use by the application 136. In these examples, the activity platform 308 may query the feature compute platform 304 to the feature data and/or the event data, which may be sent to the activity platform 308.

At step D, the indication of the activity state as determined by the selected activity model and/or the feature data from the feature compute platform 304 may be sent from the activity platform 308 to the applications 136 for use by those applications. By utilizing the activity models described above, the applications 136 may utilize activity state determinations to determine when and/or how to send recommendations, when to cause certain devices to transition to certain modes, and/or when to perform other actions associated with the devices. For example, a given application 136 may be configured to detect anomalies in user behavior when a device is configured to generate sensor data associated with user movement, such as when a user has requested that such data be generated in an aging-in-place situation. The application 136 may utilize one or more signals to detect such anomalies, such as user movement patterns, acoustic-event detection determinations, etc. The application 136, utilizing the techniques described herein, may also utilize the activity models to more accurately identify historic events associated with the device that may be utilized to compare with current events for anomaly detection. For example, the application 136 may be able to utilize events the correspond only to events that occurred during an awake state for detecting anomalies when the environment is currently associated with an awake state. By so doing, the applications 136 may utilize the determined activity states as described herein to more accurately determine which data to utilize for making application-specific determinations, and/or to increase relevant features to be utilized for making such application-specific determinations.

In additional examples, the activity-based determinations described herein may be utilized to determine what recommendation to provide to a user device 102 and/or when to send such a recommendation. For example, device-usage data may be utilized by a remote system 104 to determine when a recommendation is to be surfaced to a user device 102. By way of example, a given device 102 may be associated with a given device-usage pattern. That device-usage pattern may indicate when a device 102 is operated, how the device 102 is operated, and/or details associated with the device 102, such as a naming indicator associated with the device 102 and/or the device type of the device 102, etc. This information may be utilized to determine when a recommendation or otherwise a "hunch" is to be surfaced to a user device 102. The recommendations may include requests to operate the device in a certain way, to change information associated with the device 102, to add the device 102 to a device group, to add the device 102 to a device routine, etc. In addition to utilizing the device-usage data to determine when and how to surface such recommendations, the activity-based determinations described herein may also be used to determine when and how to surface recommendations.

For example, when the activity model(s) 134 described herein determine that a given device 102 and/or environment is associated with an active state, the recommendations may be provided to a device 102 within the environment for output by the device 102 because a user is currently in that environment and is moving in a manner associated with an active state. In other examples, such as when the environment is associated with an asleep state, the recommendation may not be output by the device 102 because a user is not currently active in the environment, but instead the recommendation may be provided to a user device 102 by way of a message that may be viewed by the user at a later time. In addition to utilizing activity-based determinations to determine when and how to provide a recommendation, the activity-based determinations may also be utilized to determine what recommendation to provide. For example, when a device 102 is associated with an away state and the device-usage data indicates that a smart door lock is typically locked but in this instance the smart door lock is in an unlocked state, the system may utilize both the device-usage data and the indication that the environment is associated with an away state to surface a recommendation to cause the smart door lock to transition to a locked state. In still other examples, the activity-based determinations may be utilized to determine whether to send a recommendation or whether to perform an action without sending a recommendation and instead, in examples, send a notification that the action has been taken. For example, if an environment is associated with an asleep state, indicating that a user is present but is not active, instead of surfacing a recommendation to lock a smart door lock that is typically in a lock state but is currently in an unlocked state, the system 104 may cause the device to transition to the locked state and provide a notification of the action to a user device 102.

Figure 4:
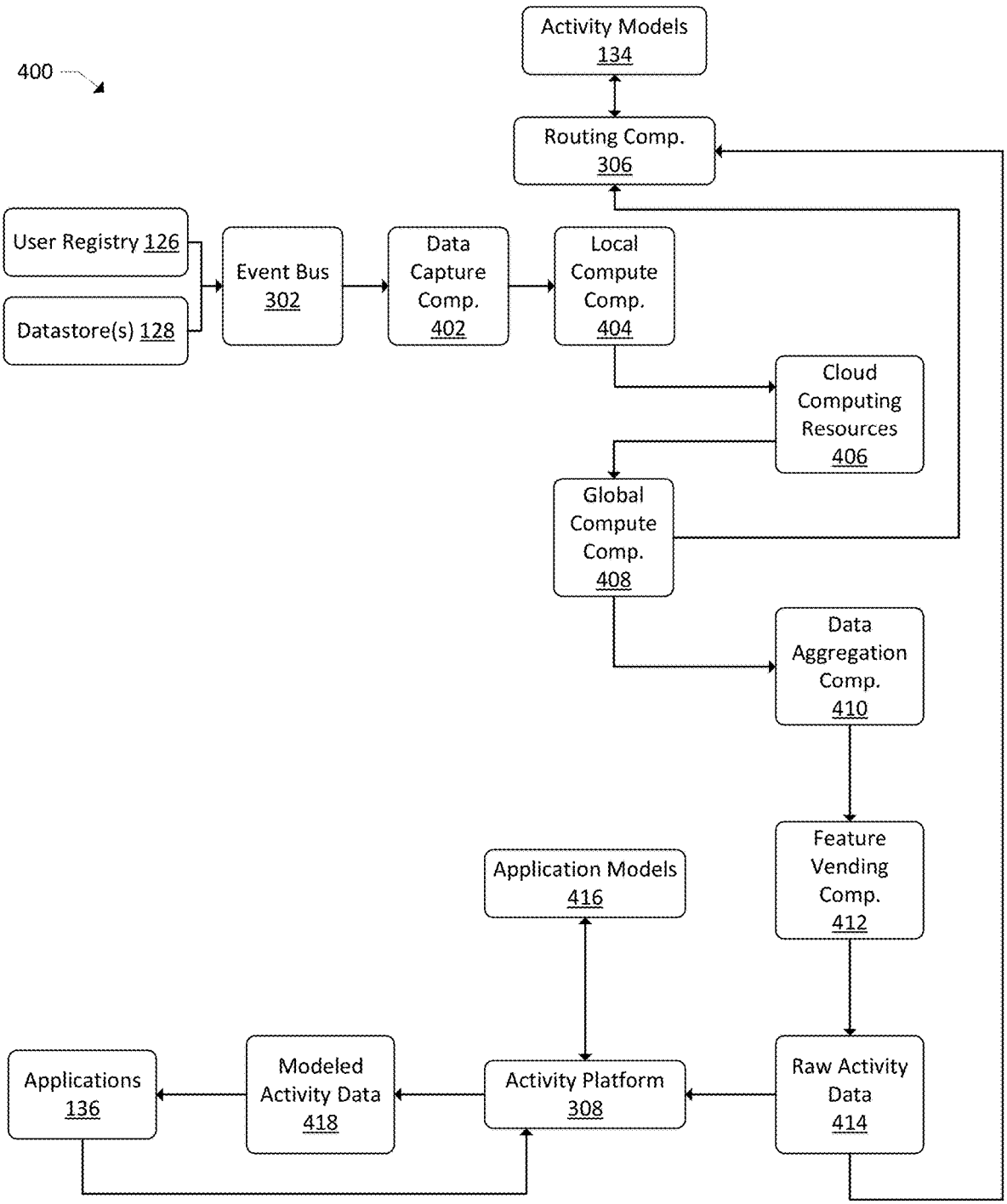
FIG. 4 illustrates a conceptual diagram of components of a system for utilizing cloud computing resources to generate features for activity-based device recommendations.

FIG. 4 illustrates a conceptual diagram of components of a system 400 for utilizing cloud computing resources to generate features for smart home activity modeling. The system 400 may include components similar to those described with respect to FIGS. 1-3, such as a user registry 126, one or more datastores 128, an event bus 302, one or more activity models 134, a routing component 306, an activity platform 308, and/or one or more applications. The system 400 may also include components such as a data capture component 402, a local compute component 404, cloud computing resources 406, a global compute component 408, a data aggregation component 410, a feature vending component 412, raw activity data 414, one or more application models 416, and/or modeled activity data 418. These features will be described below with respect to FIG. 4.

For example, the user registry 126 and/or the datastores 128 may include event data indicating events occurring with respect to electronic devices 102. For example, data indicating the state of the one or more devices, data indicating that a mobile device is in proximity to a given electronic device 102 such that the devices are in wireless communication with each other over a short-range communication network, data indicating the detection of movement in the environment, data indicating that an acoustic-event detection component of the electronic device 102 has identified an acoustic event, and/or other data such as naming indicators of the devices may be received and/or determined. This data may be generated and stored for electronic devices 102 associated with a given environment and/or for multiple electronic devices associated with multiple disparate environments. The electronic devices 102 and/or a remote system may generate and store this data, which may be utilized to generate and/or train models for determining the activity state associated with a given user profile. It should be understood that while examples of such event data are provided herein, those examples are not by way of limitation. Instead, the event data received from the electronic devices 102 may include any data that may indicate a state of the electronic devices 102, other devices, and/or the environment.

This event data may be received by the event bus 302, which may determine to send the event data to one or more other components. For example, data of different types and/or containing different content may be received by the event bus 302. The event bus 302 may be configured to identify certain data as event data that may be relevant to activity state determination and may be configured to send such identified data to the other components for further processing.

The data capture component 402 may receive the event data from the event bus 302. The data capture component 402 may be configured to generate data streams of the event data such that event data from multiple disparate electronic devices may be received and utilized. The data capture component 402 may be configured to handle large amounts of data at one time, generating various data streams for the event data to be processed.

The local compute component 404 may receive the data streams and may be configured to determine how the data streams are to be processed. For example, some of the event data may be sent to the activity models 134 for training, testing, and or use for activity state determination. In other examples, the event data may be directed to one or more of the cloud computing resources 406 to handle storage, computation, and evaluation operations. For example, when large amounts and/or types of event data are received, the cloud computing resources 406 may be provisioned based on the scale of the event data.

The cloud computing resources 406 may be configured to process the event data and utilizing a global compute component 408, which may be configured to determine how the processed data should be utilized. For example, the global compute component 408 may be configured to determine how frequently to publish the processed event data and/or how to structure the event data to be utilized by the activity models, described in more detail elsewhere herein. The global compute component 408 may be further configured to send processed event data to the routing component 306, which may be utilized to route processed event data to one or more other components, such as the activity models 134.

The data aggregation component 410 may be configured to aggregate the processed event data for use by other components of the system 400. For example, the data aggregation component 410 may periodically and/or based on receiving a command perform an aggregation of the processed event data from the global compute component 408 such that processed event data is provided to other components of the system in a systematic basis, as opposed to continuously.

The feature vending component 412 may be configured to receive the processed event data from the data aggregation component 410. The feature vending component 412 may serve to send the processed event data as raw activity data 414 to the activity platform 416. The feature vending component 412 may be configured to send raw activity data 414 in the form of a feature configured for input to the one or more activity models 134.

The activity platform 308 may be configured to request queries from the applications 136 and to send the raw activity data 414 and/or modeled activity data 418 to the applications. For example, the modeled activity data 418 may include indication of the activity state as determined by one or more of the activity models 134 and/or the application models 416 that are configured to make application-specific determinations associated with activity states.

Figure 5:
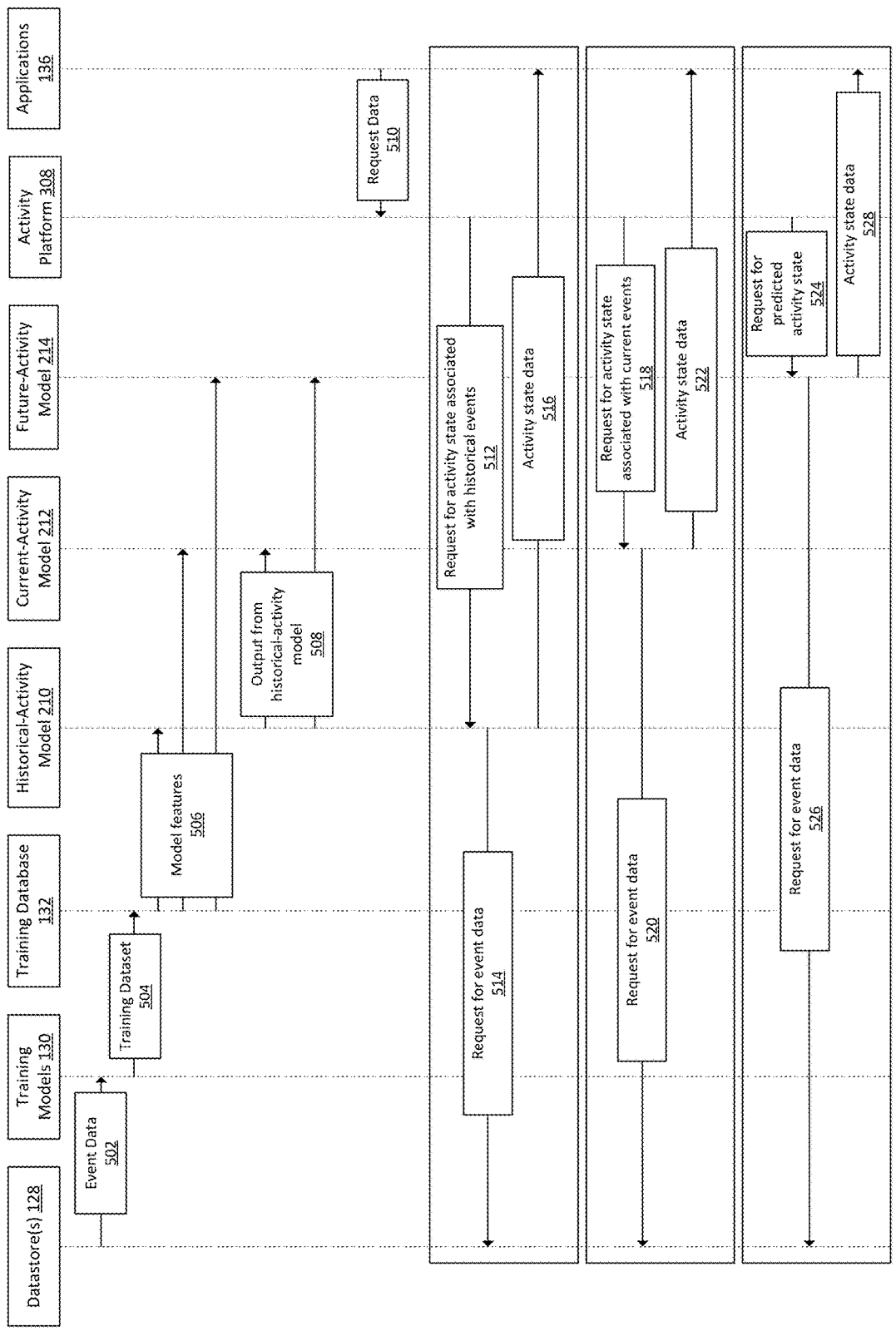
FIG. 5 illustrates a sequence diagram of example processes for activity-based device recommendations.

FIG. 5 illustrates a sequence diagram of example processes for smart home activity modeling. While the sequence diagram depicts the performance of operations and/or the transmission of certain data in a sequential manner, the operations may be performed in a different order than the order depicted in FIG. 5 and/or at least a portion of the operations may be performed in parallel.

At block 502, the training models 130 may receive event data from one or more datastores 128. For example, electronic devices may receive data from one or more other devices associated with the environment. For example, data indicating the state of the one or more devices, data indicating that a mobile device is in proximity to a given electronic device such that the devices are in wireless communication with each other over a short-range communication network, data indicating the detection of movement in the environment, data indicating that an acoustic-event detection component of the electronic device 102 has identified an acoustic event, and/or other data such as naming indicators of the devices may be received and/or determined. This data may be generated and stored for electronic devices 102 associated with a given environment and/or for multiple electronic devices associated with multiple disparate environments. The electronic devices and/or the remote system may generate and store this data, which may be utilized to generate and/or train models for determining the activity state associated with a given user profile. It should be understood that while examples of such event data are provided herein, those examples are not by way of limitation. Instead, the event data received from the electronic devices may include any data that may indicate a state of the electronic devices, other devices, and/or the environment. The event data may be sent to the remote system, which may store the event data in one or more databases, such as the datastores 128. The event data may be made available to one or more components of the remote system for smart home activity modeling as described herein.

At block 504, the training models 130 may generate a training dataset, which may be sent to a training database 132 for use in training one or more models. For example, supervised machine-learning models may be generated and be configured to accept the event data, and/or a formatted version of the event data from the datastores 128 and perform an analysis of the event data that includes labelling the event data with one or more indicators of an activity state. For example, the supervised machine-learning models may be configured to apply one or more rules to given events to label those events with an activity state. For example, event data indicating that a light has been turned on may be labeled by the supervised machine-learning models as being associated with an active state, as opposed to an asleep state or an away state. The supervised machine-learning model may generate the training dataset that includes the event data and the labeling data associated with the event data. The training dataset may be stored in association with a training database. Additionally, in examples, one or more of the electronic devices and/or user profiles associated with the electronic devices may be predetermined to be included in the evaluation dataset, which may also be stored in association with the training database. For example, certain devices may have sensors that are better suited for determining activity states and/or use of devices by given user profiles may be considered more beneficial for accurately determining activity states. In these examples, a portion of the event data corresponding to the predetermined electronic devices and/or user profiles may be input into the separate supervised machine-learning model to generate the evaluation dataset. The evaluation dataset may represent a smaller subset of the event data utilized to generate the training dataset. The evaluation dataset may be utilized by other models, as described more fully below, to test or otherwise determine the accuracy of the labeling associated with the training dataset.

At block 506, model features from the training dataset may be sent to one or more of the historical-activity model 210, the current-activity model 212, and/or the future-activity model 214 for training the models. For example, a neural network model may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic devices and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network model may "learn" how certain events, such as for certain electronic devices and/or environments, impact determining activity states.

The activity models generated and/or trained utilizing the neural network model may include one or more activity models that are configured to accept event data and generate, as output, results indicating that given event data corresponds to a given activity state and, in examples, a confidence associated with the activity state determination. The activity models may include the historical-activity model 210, which may be configured to determine an activity state associated with historical events associated with an electronic device and/or environment. For example, the historical-activity model 210 may be configured to accept, as features to the historical-activity model 210, event data corresponding to historical events. The historical-activity model 210 may generate, as output, data indicating that a given historical event corresponded to a given activity state.

For example, the historical-activity model 210 may be utilized to determine that a given time a week ago a given environment was associated with an asleep state based at least in part on the event data associated with that given time.

The activity models may also include the current-activity model 212, which may be configured to determine an activity state associated with a live or near-live event associated with an electronic device and/or environment. For example, the current-activity model 212 may be configured to accept, as features to the current-activity model 212, event data corresponding to live events and/or near-live events. In examples, use of the current-activity model 212 may be in association with the electronic device and/or the remote system causing one or more sensors or other components of the electronic device to generate live or near-live event data to be utilized by the current-activity model 212. The current-activity model 212 may generate, as output, data indicating that a given live or near-live event corresponds to a given activity state. For example, the current-activity model 212 may be utilized to determine that at a current time a given environment is associated with an active state based at least in part on event data associated with the current time.

The activity models may also include the future-activity model 214, which may be configured to predict an activity state associated with events that may occur in the future associated with an electronic device and/or environment. For example, the future-activity model 214 may be configured to accept, as features to the future-activity model 214, event data corresponding to the historical events and/or live or near-live events. The future-activity model 214 may generate, as output, data indicating that a given event that is likely to occur at a given time in the future is likely to correspond to a given activity state. For example, the future-activity model 214 may be utilized to determine that at a given time a week from now a given environment is likely to be associated with an away state based at least in part on historical event data and/or current event data associated with the given environment.

At block 508, output from the historical-activity model 210 may be sent to and utilized by the current-activity model 212 and/or the future-activity model 214 to train those models.

At block 510, one or more applications 136 may send request data for utilizing one or more of the activity models to determine an activity state associated with a user profile and/or a given environment. The request data may be received by the activity platform 308, which may determine which of the activity models is to be utilized for determining the activity state.

In examples where the historical-activity model is to be utilized, at block 512, the activity platform 308 may send a request for an activity data associated with historical events to the historical-activity model 210.

At block 514, the historical-activity model 210 may request event data and/or feature data corresponding to the event data from the datastores 128. The historical-activity model 210 may utilize the event data and/or the feature data received from the datastores 128 to determine an activity state associated with the event data.

At block 516, the historical-activity model 210 may send activity state data indicating the determined activity state to the activity platform 308 and/or the application 136 that requested the activity state determination.

In examples where the current-activity model 212 is to be utilized, at block 518, the activity platform 308 may send a request for activity data associated with live or near-live events to the current-activity model 212.

At block 520, the current-activity model 212 may request event data and/or feature data corresponding to the event data from the datastores 128. The current-activity model 212 may utilize the event data and/or the feature data received from the datastores 128 to determine an activity state associated with the event data.

At block 522, the current-activity model 212 may send activity state data indicating the determined activity state to the activity platform 308 and/or the application 136 that requested the activity state determination.

In examples where the future-activity model 214 is to be utilized, at block 524, the activity platform 308 may send a request for activity data associated with live or near-live events to the future-activity model 214.

At block 526, the future-activity model 214 may request event data and/or feature data corresponding to the event data from the datastores 128. The future-activity model 214 may utilize the event data and/or the feature data received from the datastores 128 to determine an activity state associated with the event.

At block 528, the future-activity model 214 may send activity state data indicating the determined activity state to the activity platform 308 and/or the application 136 that requested the activity state determination.

Figure 7:
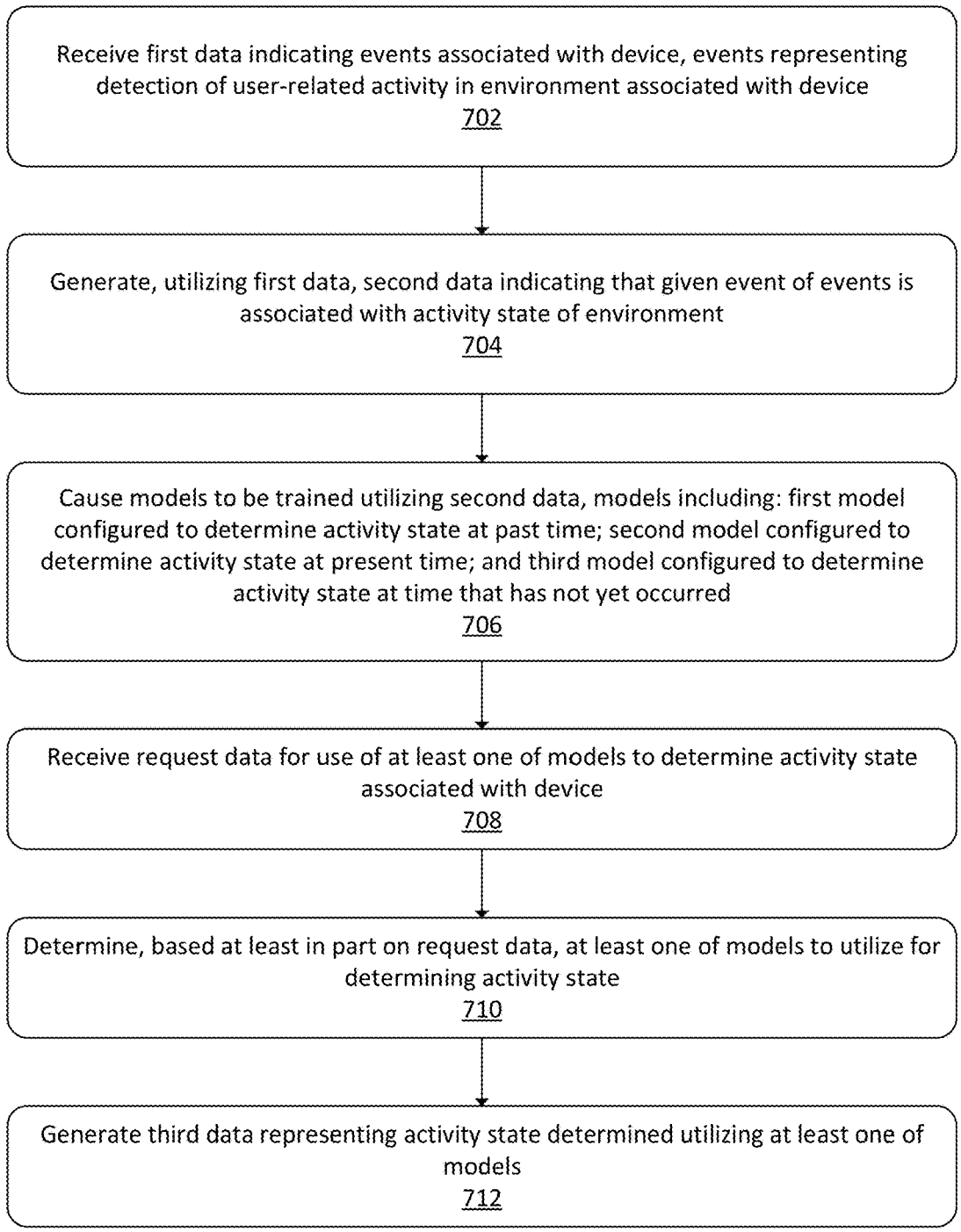
FIG. 7 illustrates a flow diagram of another example process for smart home activity modeling.

FIGS. 6 and 7 illustrate processes for smart home activity modeling. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-5, 8, and 9, although the processes may be implemented in a wide variety of other environments, architectures and systems.

FIG. 6 illustrates a flow diagram of an example process 600 for smart home activity modeling. The order in which the operations or steps are described is not intended to be construed as a limitation, and any number of the described operations may be combined in any order and/or in parallel to implement process 600.

At block 602, the process 600 may include receiving, from voice-enabled devices, first data indicating events associated with the voice-enabled devices, the events associated with detection of user devices or user-related audio. For example, electronic devices may receive data from one or more other devices associated with the environment. For example, data indicating the state of the one or more devices, data indicating that a mobile device is in proximity to a given electronic device such that the devices are in wireless communication with each other over a short-range communication network, data indicating the detection of movement in the environment, data indicating that an acoustic-event detection component of the electronic device has identified an acoustic event, and/or other data such as naming indicators of the devices may be received and/or determined. This data may be generated and stored for electronic devices associated with a given environment and/or for multiple electronic devices associated with multiple disparate environments. The electronic devices and/or the remote system may generate and store this data, which may be utilized to generate and/or train models for determining the activity state associated with a given user profile. It should be understood that while examples of such event data are provided herein, those examples are not by way of limitation. Instead, the event data received from the electronic devices may include any data that may indicate a state of the electronic devices, other devices, and/or the environment. The event data may be sent to the remote system, which may store the event data in one or more databases, such as the datastores. The event data may be made available to one or more components of the remote system for smart home activity modeling as described herein.

At block 604, the process 600 may include generating, utilizing a supervised machine-learning model, second data including activity-labeling data associated with the first data, the activity-labeling data indicating that a given event of the events is associated with an activity state, the activity state corresponding to an away state indicating absence of user presence, an active state indicating user movement, or an asleep state indicating user presence without user movement. For example, supervised machine-learning models may be generated and be configured to accept the event data, and/or a formatted version of the event data from the datastores and perform an analysis of the event data that includes labelling the event data with one or more indicators of an activity state. For example, the supervised machine-learning models may be configured to apply one or more rules to given events to label those events with an activity state. For example, event data indicating that a light has been turned on may be labeled by the supervised machine-learning models as being associated with an active state, as opposed to an asleep state or an away state. The supervised machine-learning model may generate the training dataset that includes the event data and the labeling data associated with the event data. The training dataset may be stored in association with a training database. Additionally, in examples, one or more of the electronic device and/or user profiles associated with the electronic devices may be predetermined to be included in the evaluation dataset, which may also be stored in association with the training database. For example, certain devices may have sensors that are better suited for determining activity states and/or use of devices by given user profiles may be considered more beneficial for accurately determining activity states. In these examples, a portion of the event data corresponding to the predetermined electronic devices and/or user profiles may be input into the separate supervised machine-learning model to generate the evaluation dataset. The evaluation dataset may represent a smaller subset of the event data utilized to generate the training dataset. The evaluation dataset may be utilized by other models, as described more fully below, to test or otherwise determine the accuracy of the labeling associated with the training dataset.

At block 606, the process 600 may include causing activity models to be trained utilizing a neural network model and the second data, the activity models including: a historical-activity model configured to determine the activity state associated with a given user profile at a past time;

a current-activity model configured to determine the activity state associated with the given user profile at a present time; and a future-activity model configured to determine the activity state associated with the given user profile at a time that has not yet occurred. For example, a neural network model may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic devices and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network model may "learn" how certain events, such as for certain electronic devices and/or environments, impact determining activity states.

The activity models generated and/or trained utilizing the neural network model may include one or more activity models that are configured to accept event data and generate, as output, results indicating that given event data corresponds to a given activity state and, in examples, a confidence associated with the activity state determination. The activity models may include the historical-activity model, which may be configured to determine an activity state associated with historical events associated with an electronic device and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week ago a given environment was associated with an asleep state based at least in part on the event data associated with that given time.

The activity models may also include the current-activity model, which may be configured to determine an activity state associated with a live or near-live event associated with an electronic device and/or environment. For example, the current-activity model may be configured to accept, as features to the current-activity model, event data corresponding to live events and/or near-live events. In examples, use of the current-activity model may be in association with the electronic device and/or the remote system causing one or more sensors or other components of the electronic device to generate live or near-live event data to be utilized by the current-activity model. The current-activity model may generate, as output, data indicating that a given live or near-live event corresponds to a given activity state. For example, the current-activity model may be utilized to determine that at a current time a given environment is associated with an active state based at least in part on event data associated with the current time.

The activity models may also include the future-activity model, which may be configured to predict an activity state associated with events that may occur in the future associated with an electronic device and/or environment. For example, the future-activity model may be configured to accept, as features to the future-activity model, event data corresponding to the historical events and/or live or near-live events. The future-activity model may generate, as output, data indicating that a given event that is likely to occur at a given time in the future is likely to correspond to a given activity state. For example, the future-activity model may be utilized to determine that at a given time a week from now a given environment is likely to be associated with an away state based at least in part on historical event data and/or current event data associated with the given environment.

At block 608, the process 600 may include receiving, from an application, request data for the activity state of the given voice-enabled device. For example, the request data may be received by an activity platform, which may determine which of the activity models is to be utilized for determining the activity state.

At block 610, the process 600 may include generating, utilizing at least one of the activity models, third data representing the activity state. For example, the selected activity model may query the datastores for event data relevant to the request and may utilize the event data, as features to the selected model, to generate output indicating the determined state associated with the event data.

At block 612, the process 600 may include sending the third data to the application for generating a recommendation associated with the activity state. For example, the output from the selected activity model may be considered modeled activity data and that modeled activity data may be sent to the application that requested the activity state determination. Additionally, in examples, raw event data utilized to make the activity state determination may also be sent to the application.

Additionally, or alternatively, the process 600 may include generating, utilizing a first portion of the first data corresponding to events where the activity state is known, fourth data representing output of the historical-activity model. The process 600 may also include causing the current-activity model to be trained utilizing the fourth data such that first features associated with the first portion of the first data are associated with determining the activity state at the present time. The process 600 may also include causing the future-activity model to be trained utilizing the fourth data such that second features associated with the first portion of the first data are associated with determining the activity state at the time that has not yet occurred.

Additionally, or alternatively, the process 600 may include determining that a period of time that the activity state is to be determined for corresponds to the present time. The process 600 may also include selecting, in response to determining that the period of time corresponds to the present time, the current-activity model. The process 600 may also include querying a database associated with the first data for a portion of the first data corresponding to features configured for input into the current-activity model. In these examples, generating the third data includes utilizing the current-activity model and the portion of the first data.

Additionally, or alternatively, the process 600 may include causing the voice-enabled device to present an indication associated with the activity state as determined by the application utilizing the at least one of the activity models. The process 600 may also include receiving, in response to the indication, user input data from the voice-enabled device indicating that the activity state was incorrectly determined by the application. The process 600 may include generating fourth data identifying features utilized by the at least one of the activity models for determining the activity state. The process 600 may also include causing the at least one of the activity models to be trained utilizing the fourth data such that the features indicate that a given event associated with the features is unassociated with the activity state.

FIG. 7 illustrates a flow diagram of another example process 700 for smart home activity modeling. The order in which the operations or steps are described is not intended to be construed as a limitation, and any number of the described operations may be combined in any order and/or in parallel to implement process 700.

At block 702, the process 700 may include receiving first data indicating events associated with a device, the events representing detection of user-related activity in an environment associated with the device. For example, electronic devices may receive data from one or more other devices associated with the environment. For example, data indicating the state of the one or more devices, data indicating that a mobile device is in proximity to a given electronic device such that the devices are in wireless communication with each other over a short-range communication network, data indicating the detection of movement in the environment, data indicating that an acoustic-event detection component of the electronic device has identified an acoustic event, and/or other data such as naming indicators of the devices may be received and/or determined. This data may be generated and stored for electronic devices associated with a given environment and/or for multiple electronic devices associated with multiple disparate environments. The electronic devices and/or the remote system may generate and store this data, which may be utilized to generate and/or train models for determining the activity state associated with a given user profile. It should be understood that while examples of such event data are provided herein, those examples are not by way of limitation. Instead, the event data received from the electronic devices may include any data that may indicate a state of the electronic devices, other devices, and/or the environment. The event data may be sent to the remote system, which may store the event data in one or more databases, such as the datastores. The event data may be made available to one or more components of the remote system for smart home activity modeling as described herein.

At block 704, the process 700 may include generating, utilizing the first data, second data indicating that a given event of the events is associated with an activity state of the environment. For example, supervised machine-learning models may be generated and be configured to accept the event data, and/or a formatted version of the event data from the datastores and perform an analysis of the event data that includes labelling the event data with one or more indicators of an activity state. For example, the supervised machine-learning models may be configured to apply one or more rules to given events to label those events with an activity state. For example, event data indicating that a light has been turned on may be labeled by the supervised machine-learning models as being associated with an active state, as opposed to an asleep state or an away state. The supervised machine-learning model may generate the training dataset that includes the event data and the labeling data associated with the event data. The training dataset may be stored in association with a training database. Additionally, in examples, one or more of the electronic device and/or user profiles associated with the electronic devices may be predetermined to be included in the evaluation dataset, which may also be stored in association with the training database.

For example, certain devices may have sensors that are better suited for determining activity states and/or use of devices by given user profiles may be considered more beneficial for accurately determining activity states. In these examples, a portion of the event data corresponding to the predetermined electronic devices and/or user profiles may be input into the separate supervised machine-learning model to generate the evaluation dataset. The evaluation dataset may represent a smaller subset of the event data utilized to generate the training dataset. The evaluation dataset may be utilized by other models, as described more fully below, to test or otherwise determine the accuracy of the labeling associated with the training dataset.

At block 706, the process 700 may include causing models to be trained utilizing the second data, the models including: a first model configured to determine the activity state at a past time; a second model configured to determine the activity state at a present time; and a third model configured to determine the activity state at a time that has not yet occurred. For example, a neural network model may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic devices and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network model may "learn" how certain events, such as for certain electronic devices and/or environments, impact determining activity states.

The activity models generated and/or trained utilizing the neural network model may include one or more activity models that are configured to accept event data and generate, as output, results indicating that given event data corresponds to a given activity state and, in examples, a confidence associated with the activity state determination. The activity models may include the historical-activity model, which may be configured to determine an activity state associated with historical events associated with an electronic device and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week ago a given environment was associated with an asleep state based at least in part on the event data associated with that given time.

The activity models may also include the current-activity model, which may be configured to determine an activity state associated with a live or near-live event associated with an electronic device and/or environment. For example, the current-activity model may be configured to accept, as features to the current-activity model, event data corresponding to live events and/or near-live events. In examples, use of the current-activity model may be in association with the electronic device and/or the remote system causing one or more sensors or other components of the electronic device to generate live or near-live event data to be utilized by the current-activity model. The current-activity model may generate, as output, data indicating that a given live or near-live event corresponds to a given activity state. For example, the current-activity model may be utilized to determine that at a current time a given environment is associated with an active state based at least in part on event data associated with the current time.

The activity models may also include the future-activity model, which may be configured to predict an activity state associated with events that may occur in the future associated with an electronic device and/or environment. For example, the future-activity model may be configured to accept, as features to the future-activity model, event data corresponding to the historical events and/or live or near-live events. The future-activity model may generate, as output, data indicating that a given event that is likely to occur at a given time in the future is likely to correspond to a given activity state. For example, the future-activity model may be utilized to determine that at a given time a week from now a given environment is likely to be associated with an away state based at least in part on historical event data and/or current event data associated with the given environment.

At block 708, the process 700 may include receiving request data for use of at least one of the models to determine the activity state associated with the user profile. For example, the request data may be received by an activity platform, which may determine which of the activity models is to be utilized for determining the activity state.

At block 710, the process 700 may include determining, based at least in part on the request data, at least one of the models to utilize for determining the activity state. In some examples, the request data may indicate which of the activity models are to be utilized for determining the activity state. In other examples, the request data may provide an indication of which events the application would like to determine the activity state for, and the remote system may determine which of the activity models to utilize to provide results relevant to those events.

At block 712, the process 700 may include generating third data representing the activity state determined utilizing the at least one of the models. For example, the selected activity model may query the datastores for event data relevant to the request and may utilize the event data, as features to the selected model, to generate output indicating the determined state associated with the event data.

Additionally, or alternatively, the process 700 may include generating fourth data representing output of the first model from a first portion of the first data, the first portion of the first data associated with a first portion of the events where the activity state is known. The process 700 may also include causing the second model to be trained utilizing the fourth data.

Additionally, or alternatively, the process 700 may include determining that a period of time that the activity state is to be determined corresponds to the present time. The process 700 may also include selecting, based at least in part on determining that the period of time corresponds to the present time, the second model. The process 700 may also include querying a database associated with the first data for a portion of the first data corresponding to features configured for input into the second model. In these examples, generating the third data may be based at least in part on the second model and the portion of the first data.

Additionally, or alternatively, the process 700 may include causing the device to present an indication associated with the activity state. The process 700 may also include receiving user input data from the device indicating that the activity state associated with the indication was incorrectly determined. The process 700 may also include generating fourth data identifying a feature utilized by the at least one of the models for determining the activity state. The process 700 may also include causing the at least one of the models to be trained utilizing the fourth data such that the feature indicates that a given event associated with the feature is unassociated with the activity state.

Additionally, or alternatively, the process 700 may include generating fourth data representing output of the first model utilizing a first portion of the first data, the first portion of the first data associated with a first portion of the events where the activity state is known. The process 700 may also include causing the third model to be trained utilizing the fourth data.

Additionally, or alternatively, the process 700 may include determining that a period of time that the activity state is to be determined for corresponds to the time that has not yet occurred. The process 700 may also include selecting, based at least in part on determining that the period of time corresponds to the time that has not yet occurred, the third model. The process 700 may also include querying a database associated with the first data for a portion of the first data corresponding to features configured for input into the third model. In these examples, generating the third data may be based at least in part on the third model and the portion of the first data.

Additionally, or alternatively, the process 700 may include generating a supervised machine learning model configured to accept the first data and generate labelling data indicating a portion of the events predetermined to be associated with the activity state, wherein generating the second data is based at least in part on utilizing the supervised machine learning model. The process 700 may also include generating a neural network machine learning model configured to accept the second data and generate training data indicating features of the second data that the neural network machine learning model has determined to be associated with the activity state.

Additionally, or alternatively, the process 700 may include utilizing data that indicates an operational state of an accessory device in communication with the device to train the activity models. The process 700 may also include utilizing data that indicates a user device is communicating with the device over a short-range wireless network to train the activity models. The process 700 may also include utilizing data that indicates a moving object has been detected in the environment. The process 700 may also include utilizing data that indicates an acoustic event detection component of the device has detected an acoustic event corresponding to user presence.

Figure 8:
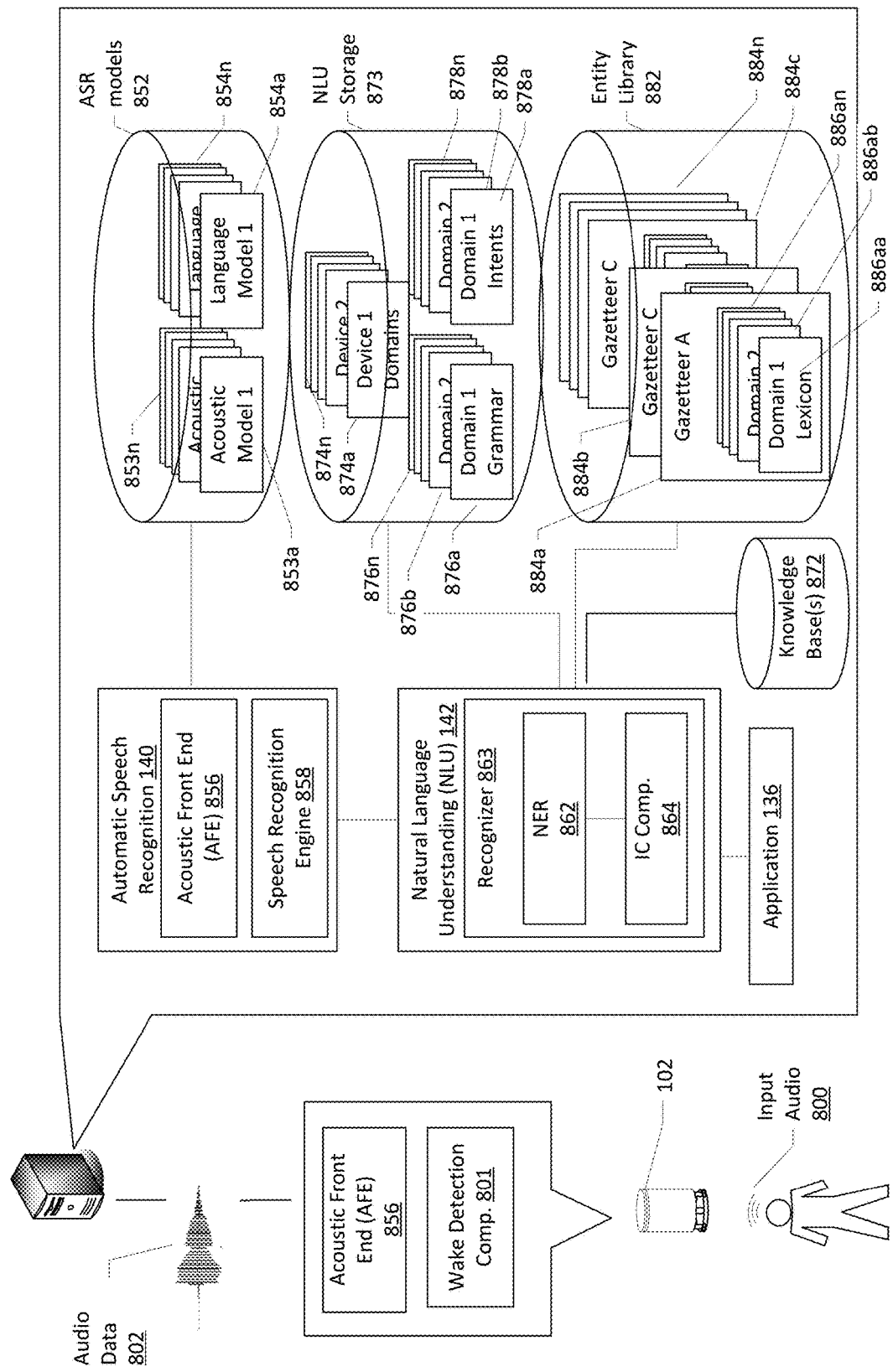
FIG. 8 illustrates a conceptual diagram of components of a speech-processing system for processing audio data provided by one or more devices.

FIG. 8 illustrates a conceptual diagram of how a spoken utterance can be processed, allowing a system to capture and execute commands spoken by a user, such as spoken commands that may follow a wakeword, or trigger expression, (i.e., a predefined word or phrase for "waking" a device, causing the device to begin sending audio data to a remote system, such as system 104). The various components illustrated may be located on a same device or different physical devices. Message between various components illustrated in FIG. 8 may occur directly or across a network 106. An audio capture component, such as a microphone 114 of the device 102, or another device, captures audio 800 corresponding to a spoken utterance. The device 102, using a wake word engine 801, then processes audio data corresponding to the audio 800 to determine if a keyword (such as a wakeword) is detected in the audio data. Following detection of a wakeword, the device 102 sends audio data 802 corresponding to the utterance to the remote system 104 that includes an ASR component 140. The audio data 802 may be output from an optional acoustic front end (AFE) 856 located on the device prior to transmission. In other instances, the audio data 802 may be in a different form for processing by a remote AFE 856, such as the AFE 856 located with the ASR component 140 of the remote system 104.

The wake word engine 801 works in conjunction with other components of the user device, for example a microphone to detect keywords in audio 800. For example, the device may convert audio 800 into audio data, and process the audio data with the wake word engine 801 to determine whether human sound is detected, and if so, if the audio data comprising human sound matches an audio fingerprint and/ or model corresponding to a particular keyword.

The user device may use various techniques to determine whether audio data includes human sound. Some embodiments may apply voice activity detection (VAD) techniques. Such techniques may determine whether human sound is present in an audio input based on various quantitative aspects of the audio input, such as the spectral slope between one or more frames of the audio input; the energy levels of the audio input in one or more spectral bands; the signal-to-noise ratios of the audio input in one or more spectral bands; or other quantitative aspects. In other embodiments, the user device may implement a limited classifier configured to distinguish human sound from background noise. The classifier may be implemented by techniques such as linear classifiers, support vector machines, and decision trees. In still other embodiments, Hidden Markov Model (HMM) or Gaussian Mixture Model (GMM) techniques may be applied to compare the audio input to one or more acoustic models in human sound storage, which acoustic models may include models corresponding to human sound, noise (such as environmental noise or background noise), or silence. Still other techniques may be used to determine whether human sound is present in the audio input.

Once human sound is detected in the audio received by user device (or separately from human sound detection), the user device may use the wake-word component 801 to perform wakeword detection to determine when a user intends to speak a command to the user device. This process may also be referred to as keyword detection, with the wakeword being a specific example of a keyword. Specifically, keyword detection may be performed without performing linguistic analysis, textual analysis or semantic analysis. Instead, incoming audio (or audio data) is analyzed to determine if specific characteristics of the audio match preconfigured acoustic waveforms, audio fingerprints, or other data to determine if the incoming audio "matches" stored audio data corresponding to a keyword.

Thus, the wake word engine 801 may compare audio data to stored models or data to detect a wakeword. One approach for wakeword detection applies general large vocabulary continuous speech recognition (LVCSR) systems to decode the audio signals, with wakeword searching conducted in the resulting lattices or confusion networks. LVCSR decoding may require relatively high computational resources. Another approach for wakeword spotting builds hidden Markov models (HMM) for each key wakeword word and non-wakeword speech signals respectively. The non-wakeword speech includes other spoken words, background noise, etc. There can be one or more HMMs built to model the non-wakeword speech characteristics, which are named filler models. Viterbi decoding is used to search the best path in the decoding graph, and the decoding output is further processed to make the decision on keyword presence. This approach can be extended to include discriminative information by incorporating hybrid DNN-HMM decoding framework. In another embodiment, the wakeword spotting system may be built on deep neural network (DNN)/recursive neural network (RNN) structures directly, without HMM involved. Such a system may estimate the posteriors of wakewords with context information, either by stacking frames within a context window for DNN, or using RNN. Following-on posterior threshold tuning or smoothing is applied for decision making. Other techniques for wakeword detection, such as those known in the art, may also be used.

Once the wakeword is detected, the local device 102 may "wake" and begin transmitting audio data 802 corresponding to input audio 800 to the remote system 104 for speech processing. Audio data corresponding to that audio may be sent to remote system 104 for routing to a recipient device or may be sent to the remote system 104 for speech processing for interpretation of the included speech (either for purposes of enabling voice-messages and/or for purposes of executing a command in the speech). The audio data 802 may include data corresponding to the wakeword, or the portion of the audio data corresponding to the wakeword may be removed by the local device 102 prior to sending. Further, a local device may "wake" upon detection of speech/spoken audio above a threshold, as described herein. Upon receipt by the remote system 104, an ASR component 140 may convert the audio data 802 into text. The ASR transcribes audio data into text data representing the words of the speech contained in the audio data 802. The text data may then be used by other components for various purposes, such as executing system commands, inputting data, etc. A spoken utterance in the audio data is input to a processor configured to perform ASR which then interprets the utterance based on the similarity between the utterance and pre-established language models 854 stored in an ASR model knowledge base (ASR Models Storage 852). For example, the ASR process may compare the input audio data with models for sounds (e.g., subword units or phonemes) and sequences of sounds to identify words that match the sequence of sounds spoken in the utterance of the audio data.

The different ways a spoken utterance may be interpreted (i.e., the different hypotheses) may each be assigned a probability or a confidence score representing the likelihood that a particular set of words matches those spoken in the utterance. The confidence score may be based on a number of factors including, for example, the similarity of the sound in the utterance to models for language sounds (e.g., an acoustic model 853 stored in an ASR Models Storage 852), and the likelihood that a particular word that matches the sounds would be included in the sentence at the specific location (e.g., using a language or grammar model). Thus, each potential textual interpretation of the spoken utterance (hypothesis) is associated with a confidence score. Based on the considered factors and the assigned confidence score, the ASR process 140 outputs the most likely text recognized in the audio data. The ASR process may also output multiple hypotheses in the form of a lattice or an N-best list with each hypothesis corresponding to a confidence score or other score (such as probability scores, etc.).

The device or devices performing the ASR processing may include an acoustic front end (AFE) 856 and a speech recognition engine 858. The acoustic front end (AFE) 856 transforms the audio data from the microphone into data for processing by the speech recognition engine 858. The speech recognition engine 858 compares the speech recognition data with acoustic models 853, language models 854, and other data models and information for recognizing the speech conveyed in the audio data. The AFE 856 may reduce noise in the audio data and divide the digitized audio data into frames representing time intervals for which the AFE 856 determines a number of values, called features, representing the qualities of the audio data, along with a set of those values, called a feature vector, representing the features/qualities of the audio data within the frame. Many different features may be determined, as known in the art, and each feature represents some quality of the audio that may be useful for ASR processing. A number of approaches may be used by the AFE to process the audio data, such as mel-frequency cepstral coefficients (MFCCs), perceptual linear predictive (PLP) techniques, neural network feature vector techniques, linear discriminant analysis, semi-tied covariance matrices, or other approaches known to those of skill in the art.

The speech recognition engine 858 may process the output from the AFE 856 with reference to information stored in speech/model storage (852). Alternatively, post front-end processed data (such as feature vectors) may be received by the device executing ASR processing from another source besides the internal AFE. For example, the user device may process audio data into feature vectors (for example using an on-device AFE 856) and transmit that information to a server across a network for ASR processing. Feature vectors may arrive at the remote system 106 encoded, in which case they may be decoded prior to processing by the processor executing the speech recognition engine 858.

The speech recognition engine 858 attempts to match received feature vectors to language phonemes and words as known in the stored acoustic models 853 and language models 854. The speech recognition engine 858 computes recognition scores for the feature vectors based on acoustic information and language information. The acoustic information is used to calculate an acoustic score representing a likelihood that the intended sound represented by a group of feature vectors matches a language phoneme. The language information is used to adjust the acoustic score by considering what sounds and/or words are used in context with each other, thereby improving the likelihood that the ASR process will output speech results that make sense grammatically. The specific models used may be general models or may be models corresponding to a particular domain, such as music, banking, etc. By way of example, a user utterance may be "Alexa, turn on Light A?" The wake detection component may identify the wake word, otherwise described as a trigger expression, "Alexa," in the user utterance and may "wake" based on identifying the wake word. Audio data corresponding to the user utterance may be sent to the remote system 106, where the speech recognition engine 858 may identify, determine, and/or generate text data corresponding to the user utterance, here "turn on Light A."

The speech recognition engine 858 may use a number of techniques to match feature vectors to phonemes, for example using Hidden Markov Models (HMMs) to determine probabilities that feature vectors may match phonemes. Sounds received may be represented as paths between states of the HMM and multiple paths may represent multiple possible text matches for the same sound.

Following ASR processing, the ASR results may be sent by the speech recognition engine 858 to other processing components, which may be local to the device performing ASR and/or distributed across the network(s). For example, ASR results in the form of a single textual representation of the speech, an N-best list including multiple hypotheses and respective scores, lattice, etc. may be sent to the remote system 106, for natural language understanding (NLU) processing, such as conversion of the text into commands for execution, either by the user device, by the remote system 104, or by another device (such as a server running a specific application like a search engine, etc.).

The device performing NLU processing 142 (e.g., server 104) may include various components, including potentially dedicated processor(s), memory, storage, etc. As shown in FIG. 8, an NLU component 142 may include a recognizer 863 that includes a named entity recognition (NER) component 862 which is used to identify portions of query text that correspond to a named entity that may be recognizable by the system. A downstream process called named entity resolution links a text portion to a specific entity known to the system. To perform named entity resolution, the system may utilize gazetteer information (884*a*-884*n*) stored in entity library storage 882. The gazetteer information may be used for entity resolution, for example matching ASR results with different entities (such as voice-enabled devices, accessory devices, etc.) Gazetteers may be linked to users (for example a particular gazetteer may be associated with a specific user's device associations), may be linked to certain domains (such as music, shopping, etc.), or may be organized in a variety of other ways.

Generally, the NLU process takes textual input (such as processed from ASR 140 based on the utterance input audio 800) and attempts to make a semantic interpretation of the text. That is, the NLU process determines the meaning behind the text based on the individual words and then implements that meaning. NLU processing 142 interprets a text string to derive an intent or a desired action from the user as well as the pertinent pieces of information in the text that allow a device (e.g., device 102) to complete that action. For example, if a spoken utterance is processed using ASR 140 and outputs the text "turn on Light A" the NLU process may determine that the user intended to activate "Light A."

The NLU 142 may process several textual inputs related to the same utterance. For example, if the ASR 140 outputs N text segments (as part of an N-best list), the NLU may process all N outputs to obtain NLU results.

As will be discussed further below, the NLU process may be configured to parse and tag to annotate text as part of NLU processing. For example, for the text "turn on Light A," "turn on" may be tagged as a command (to operate an accessory device) and "Light A" may be tagged as the naming identifier of the accessory device to be operated.

To correctly perform NLU processing of speech input, an NLU process 142 may be configured to determine a "domain" of the utterance so as to determine and narrow down which services offered by the endpoint device (e.g., remote system 104 or the user device) may be relevant. For example, an endpoint device may offer services relating to interactions with a telephone service, a contact list service, a calendar/scheduling service, a music player service, etc. Words in a single text query may implicate more than one service, and some services may be functionally linked (e.g., both a telephone service and a calendar service may utilize data from the contact list).

The named entity recognition (NER) component 862 receives a query in the form of ASR results and attempts to identify relevant grammars and lexical information that may be used to construe meaning. To do so, the NLU component 142 may begin by identifying potential domains that may relate to the received query. The NLU storage 873 includes a database of devices (874*a*-874*n*) identifying domains associated with specific devices. For example, the user device may be associated with domains for music, telephony, calendaring, contact lists, and device-specific messages, but not video. In addition, the entity library may include database entries about specific services on a specific device, either indexed by Device ID, User ID, or Household ID, or some other indicator.

In NLU processing, a domain may represent a discrete set of activities having a common theme, such as "banking," health care," "smart home," "communications," "shopping," "music," "calendaring," etc. As such, each domain may be associated with a particular recognizer 863, language model and/or grammar database (876*a*-876*n*), a particular set of intents/actions (878*a*-878*n*), and a particular personalized lexicon (886). Each gazetteer (884*a*-884*n*) may include domain-indexed lexical information associated with a particular user and/or device. For example, the Gazetteer A (884*a*) includes domain-index lexical information 886*aa* to 886*an*. A user's contact-list lexical information might include the names of contacts. Since every user's contact list is presumably different, this personalized information improves entity resolution.

As noted above, in traditional NLU processing, a query may be processed applying the rules, models, and information applicable to each identified domain. For example, if a query potentially implicates both messages and, for example, music, the query may, substantially in parallel, be NLU processed using the grammar models and lexical information for messages, and will be processed using the grammar models and lexical information for music. The responses based on the query produced by each set of models is scored, with the overall highest ranked result from all applied domains ordinarily selected to be the correct result.

An intent classification (IC) component 864 parses the query to determine an intent or intents for each identified domain, where the intent corresponds to the action to be performed that is responsive to the query. Each domain is associated with a database (878*a*-878*n*) of words linked to intents. For example, a communications intent database may link words and phrases such as "identify song," "song title," "determine song," to a "song title" intent. By way of further example, a timer intent database may link words and phrases such as "set," "start," "initiate," and "enable" to a "set timer" intent. A voice-message intent database, meanwhile, may link words and phrases such as "send a message," "send a voice message," "send the following," or the like. The IC component 864 identifies potential intents for each identified domain by comparing words in the query to the words and phrases in the intents database 878. In some instances, the determination of an intent by the IC component 864 is performed using a set of rules or templates that are processed against the incoming text to identify a matching intent.

In order to generate a particular interpreted response, the NER 862 applies the grammar models and lexical information associated with the respective domain to actually recognize a mention of one or more entities in the text of the query. In this manner, the NER 862 identifies "slots" or values (i.e., particular words in query text) that may be needed for later command processing. Depending on the complexity of the NER 862, it may also label each slot with a type of varying levels of specificity (such as noun, place, device name, device location, city, artist name, song name, amount of time, timer number, or the like). Each grammar model 876 includes the names of entities (i.e., nouns) commonly found in speech about the particular domain (i.e., generic terms), whereas the lexical information 886 from the gazetteer 884 is personalized to the user(s) and/or the device. For instance, a grammar model associated with the shopping domain may include a database of words commonly used when people discuss shopping.

The intents identified by the IC component 864 are linked to domain-specific grammar frameworks (included in 876) with "slots" or "fields" to be filled with values. Each slot/field corresponds to a portion of the query text that the system believes corresponds to an entity. To make resolution more flexible, these frameworks would ordinarily not be structured as sentences, but rather based on associating slots with grammatical tags. For example, if "purchase" is an identified intent, a grammar (876) framework or frameworks may correspond to sentence structures such as "purchase item called 'Item A' from Marketplace A."

For example, the NER component 862 may parse the query to identify words as subject, object, verb, preposition, etc., based on grammar rules and/or models, prior to recognizing named entities. The identified verb may be used by the IC component 864 to identify intent, which is then used by the NER component 862 to identify frameworks. A framework for the intent of "play a song," meanwhile, may specify a list of slots/fields applicable to play the identified "song" and any object modifier (e.g., specifying a music collection from which the song should be accessed) or the like. The NER component 862 then searches the corresponding fields in the domain-specific and personalized lexicon(s), attempting to match words and phrases in the query tagged as a grammatical object or object modifier with those identified in the database(s).

This process includes semantic tagging, which is the labeling of a word or combination of words according to their type/semantic meaning. Parsing may be performed using heuristic grammar rules, or an NER model may be constructed using techniques such as hidden Markov models, maximum entropy models, log linear models, conditional random fields (CRF), and the like.

The frameworks linked to the intent are then used to determine what database fields should be searched to determine the meaning of these phrases, such as searching a user's gazette for similarity with the framework slots. If the search of the gazetteer does not resolve the slot/field using gazetteer information, the NER component 862 may search the database of generic words associated with the domain (in the knowledge base 872). So, for instance, if the query was "identify this song," after failing to determine which song is currently being output, the NER component 862 may search the domain vocabulary for songs that have been requested lately. In the alternative, generic words may be checked before the gazetteer information, or both may be tried, potentially producing two different results.

The output data from the NLU processing (which may include tagged text, commands, etc.) may then be sent to an application 136. The destination application 136 may be determined based on the NLU output. For example, if the NLU output includes a command to send a message, the destinated application 136 may be a message sending application, such as one located on the user device or in a message sending appliance, configured to execute a message sending command. If the NLU output includes a search request, the destination application 136 may include a search engine processor, such as one located on a search server, configured to execute a search command. After the appropriate command is generated based on the intent of the user, the application 136 may provide some or all of this information to a text-to-speech (TTS) engine. The TTS engine may then generate an actual audio file for outputting the audio data determined by the application 136 (e.g., "okay," or "Light A on"). After generating the file (or "audio data"), the TTS engine may provide this data back to the remote system 104.

The NLU operations of existing systems may take the form of a multi-domain architecture. Each domain (which may include a set of intents and entity slots that define a larger concept such as music, books etc. as well as components such as trained models, etc. used to perform various NLU operations such as NER, IC, or the like) may be constructed separately and made available to an NLU component 144 during runtime operations where NLU operations are performed on text (such as text output from an ASR component 140). Each domain may have specially configured components to perform various steps of the NLU operations.

For example, in a NLU system, the system may include a multi-domain architecture consisting of multiple domains for intents/commands executable by the system (or by other devices connected to the system), such as music, video, books, and information. The system may include a plurality of domain recognizers, where each domain may include its own recognizer 863. Each recognizer may include various NLU components such as an NER component 862, IC component 864 and other components such as an entity resolver, or other components.

For example, a messaging domain recognizer 863-A (Domain A) may have an NER component 862-A that identifies what slots (i.e., portions of input text) may correspond to particular words relevant to that domain. The words may correspond to entities such as (for the messaging domain) a recipient. An NER component 862 may use a machine learning model, such as a domain specific conditional random field (CRF) to both identify the portions corresponding to an entity as well as identify what type of entity corresponds to the text portion. The messaging domain recognizer 863-A may also have its own intent classification (IC) component 864-A that determines the intent of the text assuming that the text is within the proscribed domain. An IC component may use a model, such as a domain specific maximum entropy classifier to identify the intent of the text, where the intent is the action the user desires the system to perform. For this purpose, the remote system computing device 104 may include a model training component. The model training component may be used to train the classifier(s)/machine learning models discussed above.

As noted above, multiple devices may be employed in a single speech-processing system. In such a multi-device system, each of the devices may include different components for performing different aspects of the speech processing. The multiple devices may include overlapping components. The components of the user device and the remote system 104, as illustrated herein are exemplary, and may be located in a stand-alone device or may be included, in whole or in part, as a component of a larger device or system, may be distributed across a network or multiple devices connected by a network, etc.

Figure 9:
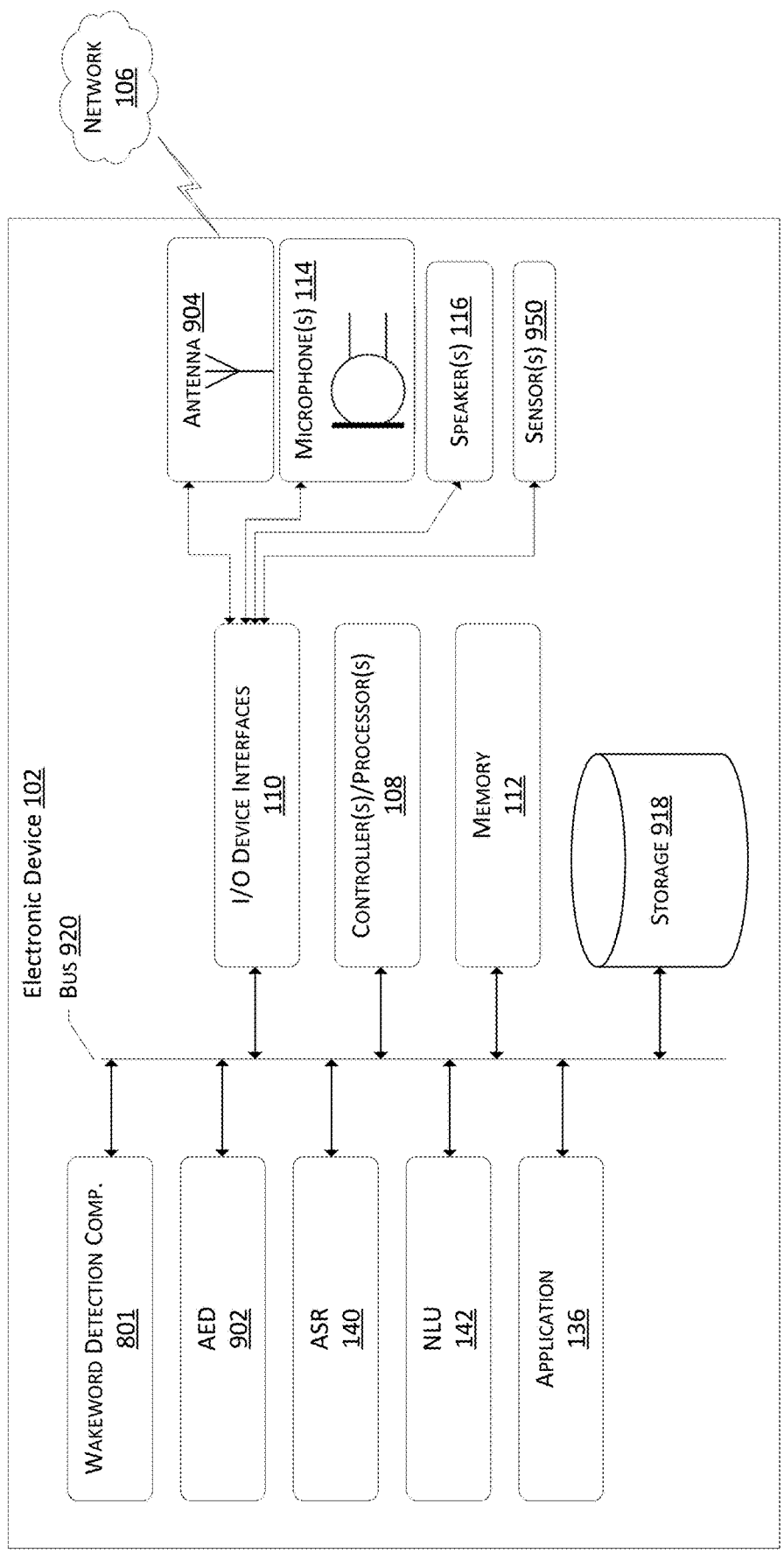
FIG. 9 illustrates a conceptual diagram of example components of an electronic device that may be utilized in association with activity-based device recommendations.

FIG. 9 illustrates a conceptual diagram of example components of an electronic device 102 that may be utilized in association with configurations for smart home activity modeling. The device 102 may be implemented as a stand-alone device 102 that is relatively simple in terms of functional capabilities with limited input/output components, memory, and processing capabilities. For instance, the device 102 may not have a keyboard, keypad, or other form of mechanical input. The device 102 may also lack a display (other than simple lights, for instance) and a touch screen to facilitate visual presentation and user touch input. Instead, the device 102 may be implemented with the ability to receive and output audio, a network interface (wireless or wire-based), power, and processing/memory capabilities. In certain implementations, a limited set of one or more input components may be employed (e.g., a dedicated button to initiate a configuration, power on/off, etc.) by the device 102. Nonetheless, the primary, and potentially only mode, of user interaction with the device 102 is through voice input and audible output. In some instances, the device 102 may simply comprise a microphone 114, a power source, and functionality for sending generated audio data via one or more antennas 904 to another device.

The device 102 may also be implemented as a more sophisticated computing device, such as a computing device similar to, or the same as, a smart phone or personal digital assistant. The device 102 may include a display with a touch interface and various buttons for providing input as well as additional functionality such as the ability to send and receive communications. Alternative implementations of the device 102 may also include configurations as a personal computer. The personal computer may include a keyboard, a mouse, a display, and other hardware or functionality that is found on a desktop, notebook, netbook, or other personal computing devices. In examples, the device 102 may include an automobile, such as a car. In other examples, the device 102 may include a pin on a user's clothes or a phone on a user's person. In examples, the device 102 and may not include speaker(s) and may utilize speaker(s) of an external or peripheral device to output audio via the speaker(s) of the external/peripheral device. In this example, the device 102 might represent a set-top box (STB), and the device 102 may utilize speaker(s) of another device such as a television that is connected to the STB for output of audio via the external speakers. In other examples, the device 102 may not include the microphone(s) 114, and instead, the device 102 can utilize microphone(s) of an external or peripheral device to capture audio and/or generate audio data. In this example, the device 102 may utilize microphone(s) of a headset that is coupled (wired or wirelessly) to the device 102. These types of devices are provided by way of example and are not intended to be limiting, as the techniques described in this disclosure may be used in essentially any device that has an ability to recognize speech input or other types of natural language input.

The device 102 of FIG. 9 may include one or more controllers/processors 108, that may include a central processing unit (CPU) for processing data and computer-readable instructions, and memory 112 for storing data and instructions of the device 102. The device 102 may also be connected to removable or external non-volatile memory and/or storage, such as a removable memory card, memory key drive, networked storage, etc., through input/output device interfaces 110.

Computer instructions for operating the device 102 and its various components may be executed by the device's controller(s)/processor(s) 108, using the memory 112 as temporary "working" storage at runtime. A device's computer instructions may be stored in a non-transitory manner in non-volatile memory 112, storage 918, or an external device (s). Alternatively, some or all of the executable instructions may be embedded in hardware or firmware on the device 102 in addition to or instead of software.

The device 102 may include input/output device interfaces 110. A variety of components may be connected through the input/output device interfaces 110. Additionally, the device 102 may include an address/data bus 920 for conveying data among components of the respective device. Each component within a device 102 may also be directly connected to other components in addition to, or instead of, being connected to other components across the bus 920.

The device 102 may include a display, which may comprise a touch interface. Any suitable display technology, such as liquid crystal display (LCD), organic light emitting diode (OLED), electrophoretic, and so on, may be utilized for the displays. Furthermore, the processor(s) 108 may comprise graphics processors for driving animation and video output on the associated display, or the device 102 may be "headless" and may primarily rely on spoken commands for input. As a way of indicating to a user that a connection between another device has been opened, the device 102 may be configured with one or more visual indicators, such as the light elements(s), which may be in the form of LED(s) or similar components (not illustrated), that may change color, flash, or otherwise provide visible light output, such as for a notification indicator on the device 102. The input/output device interfaces 110 that connect to a variety of components. This wired or a wireless audio and/or video port may allow for input/output of audio/video to/from the device 102. The device 102 may also include an audio capture component. The audio capture component may be, for example, a microphone 114 or array of microphones, a wired headset or a wireless headset, etc. The microphone 114 may be configured to capture audio. If an array of microphones is included, approximate distance to a sound's point of origin may be determined using acoustic localization based on time and amplitude differences between sounds captured by different microphones of the array. The device 102 (using microphone 114, wakeword detection component 801, ASR component 140, etc.) may be configured to generate audio data corresponding to captured audio. The device 102 (using input/output device interfaces 110, antenna 904, etc.) may also be configured to transmit the audio data to the remote system 104 for further processing or to process the data using internal components such as a wakeword detection component 801.

Via the antenna(s) 904, the input/output device interface 110 may connect to one or more networks 106 via a wireless local area network (WLAN) (such as WiFi) radio, Bluetooth, and/or wireless network radio, such as a radio capable of communication with a wireless communication network such as a Long Term Evolution (LTE) network, WiMAX network, 3G network, 4G network, 5G network, etc. A wired connection such as Ethernet may also be supported. Universal Serial Bus (USB) connections may also be supported. Power may be provided to the device 102 via wired connection to an external alternating current (AC) outlet, and/or via onboard power sources, such as batteries, solar panels, etc.

Through the network(s) 106, the speech-processing system may be distributed across a networked environment. Accordingly, the device 102 and/or the remote system 104 may include an ASR component 140. The ASR component 140 of device 102 may be of limited or extended capabilities. The ASR component 140 may include language models stored in ASR model storage component, and an ASR component 140 that performs automatic speech recognition. If limited speech recognition is included, the ASR component 140 may be configured to identify a limited number of words, such as keywords detected by the device, whereas extended speech recognition may be configured to recognize a much larger range of words.

The device 102 and/or the remote system 104 may include a limited or extended NLU component 142. The NLU component 142 of device 102 may be of limited or extended capabilities. The NLU component 142 may comprise a name entity recognition module, an intent classification module and/or other components. The NLU component 142 may also include a stored knowledge base and/or entity library, or those storages may be separately located.

In examples, AED 902 may also be performed by the device 102. In these examples, the operations may include causing the AED component 902 to be enabled or otherwise turned on, or the operations may include causing the AED component 902 to transition from a first mode to a second mode representing a higher sensitivity to audio data generated by the microphone 114. The AED component 902 may utilize the audio data generated by the microphone 114 to determine if an audio fingerprint of the audio data, or portion thereof, corresponds to a reference audio fingerprint associated with the predefined event. For example, the one or more predefined events may be associated with one or more reference audio fingerprint characteristics of sound made when the event occurs. For example, the sound of a given person speaking may have a given audio fingerprint, the sound of a different person speaking may have another audio fingerprint, etc. The AED component 902 may receive an indication that audio has been captured and may utilize reference audio fingerprints for analysis in association with the audio fingerprint in question. It should be understood that while the term "audio fingerprint" is utilized herein, that term may include other terms such as "audio fingerprint" and/or "audio characteristics" and may correspond to characteristics of the audio data. For example, audio fingerprints may be generated utilizing a spectrogram that may split the audio data up over time and graphs frequency to amplitude over time. Peaks in frequency and/or amplitude may be identified in the spectrogram and may be utilized as characteristic points for comparison to reference audio fingerprints. The AED component 902 may determine that the audio fingerprint corresponds to at least one of the reference audio fingerprints, such as to a given confidence level, and may generate confirmatory data indicating that the audio fingerprint corresponds to the at least one reference audio fingerprint.

The device 102 and/or the remote system 104 may also include an application 136 that is configured to execute commands/functions associated with a spoken command as described herein. The device 102 may include a wake word engine, which may be a separate component or may be included in an ASR component 140. The wakeword detection component 801 receives audio signals and detects occurrences of a particular expression (such as a configured keyword) in the audio. This may include detecting a change in frequencies over a specific period of time where the change in frequencies results in a specific audio fingerprint that the system recognizes as corresponding to the keyword. Keyword detection may include analyzing individual directional audio signals, such as those processed post-beamforming if applicable. Other techniques known in the art of keyword detection (also known as keyword spotting) may also be used. In some embodiments, the device 102 may be configured collectively to identify a set of the directional audio signals in which the wake expression is detected or in which the wake expression is likely to have occurred. In examples, the device 102 and may not include speaker(s) 116 and may utilize speaker(s) of an external or peripheral device to output audio via the speaker(s) of the external/peripheral device.

To assist with presence detection and/or user profile authentication, for example, the device 102 may include one or more sensors 950 that may be configured to detect environmental changes indicative of user presence and/or user profile authentication. The sensors 950 may include, for example, radar, audio sensors such as the microphones 114, ultrasonic sensors, cameras, temperature sensors, motion sensors, light sensors, etc. For example, a given device 102 may include sensors 950 such as an ultra-wide band antenna configured to receive electromagnetic waves with a bandwidth at or around 6 GHz. The device 102 may also include a millimeter-wave band antenna configured to receive electromagnetic waves with a bandwidth at or around 60 GHz. This dual-band radar functionality may be utilized to detect movement that is likely to correspond to a predefined event, such as a person falling. By utilizing dual-band radar functionality as described herein, the radar may be able to detect event occurrences in rooms or other types of spaces in both the room in which the sensing device is located and other, such as adjacent, rooms. For example, the electromagnetic waves may be received at the antennas and corresponding sensor data may be generated. The sensor data may be utilized by the device to determine if one or more predefined events have occurred. Event data indicating that the device has determined that a predefined event has occurred may be sent from the device to a remote system for event-detection confirmation processing. In other examples, the sensor data may be sent from the device to another device and/or system, such as a remote system configured to process the sensor data, to determine whether the one or more predefined events has occurred. The ultrasonic radar components described above may include functionality that allows for sound waves in the ultrasonic frequency to be emitted and received for the detection of predefined events and/or the detection of subjects in an environment. The sensors 950 may also include any sensor associated with a smart-home device or otherwise devices associated with smart-home devices. For example, the sensors 950 may include temperature sensors, motion sensors, buttons that may be pressed by a user, and/or ambient light sensors. It should be understood that the sensors described herein may be sensors configured to detect human activity in an environment, such as microphones, motion sensors, door sensors, home security cameras and/or contacts, appliance usage sensors, light switches, and/or any other sensor that monitors a room or other environment for activity. This is in contrast to devices designed to specifically monitor physical characteristics of a person, such as watches, phones, or other devices that measure steps, heartrate, and/or whether a person is standing and/or laying down, for example.

Figure 10:
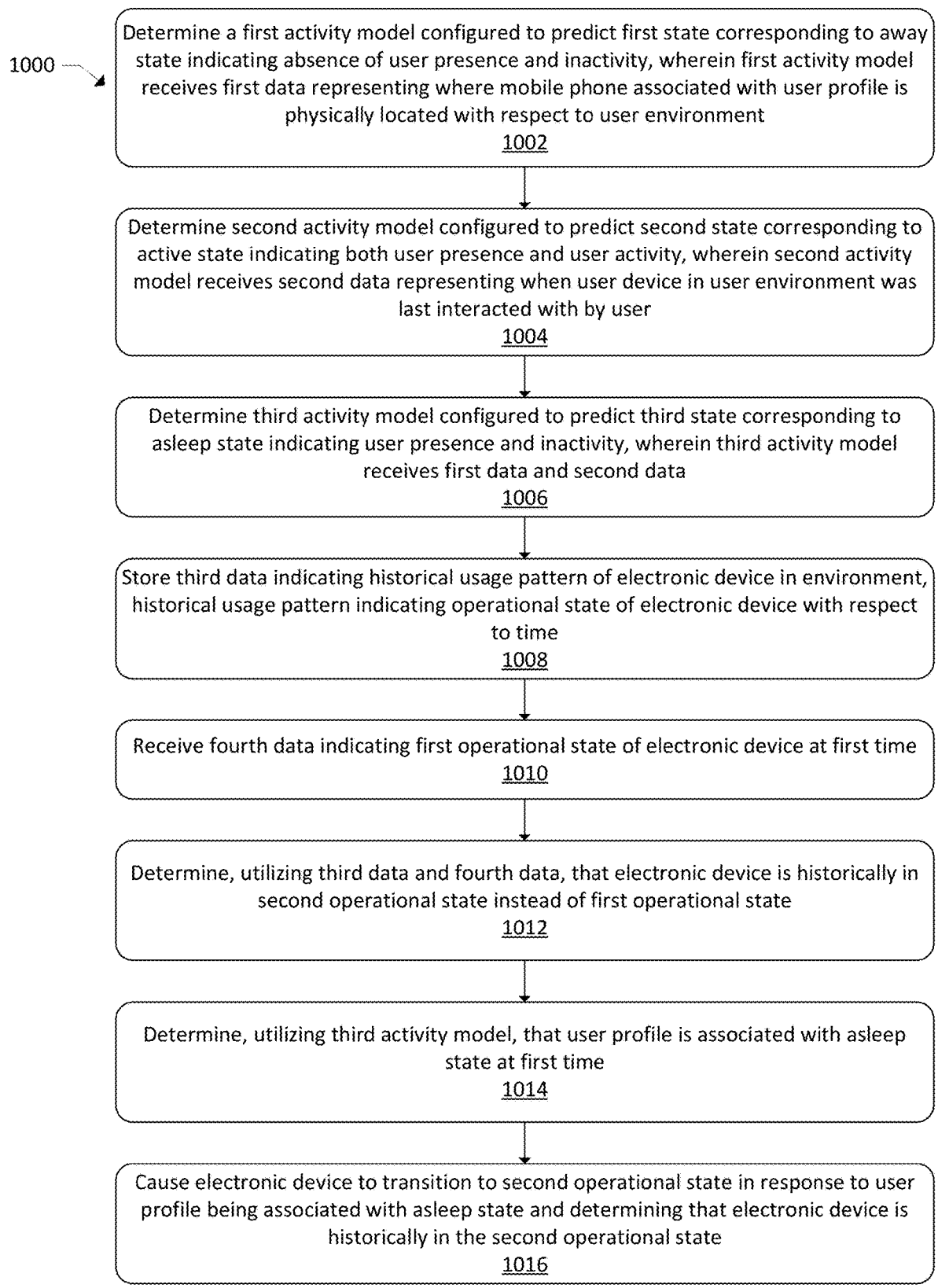
FIG. 10 illustrates a flow diagram of an example process for activity-based device recommendations.
Figure 11:
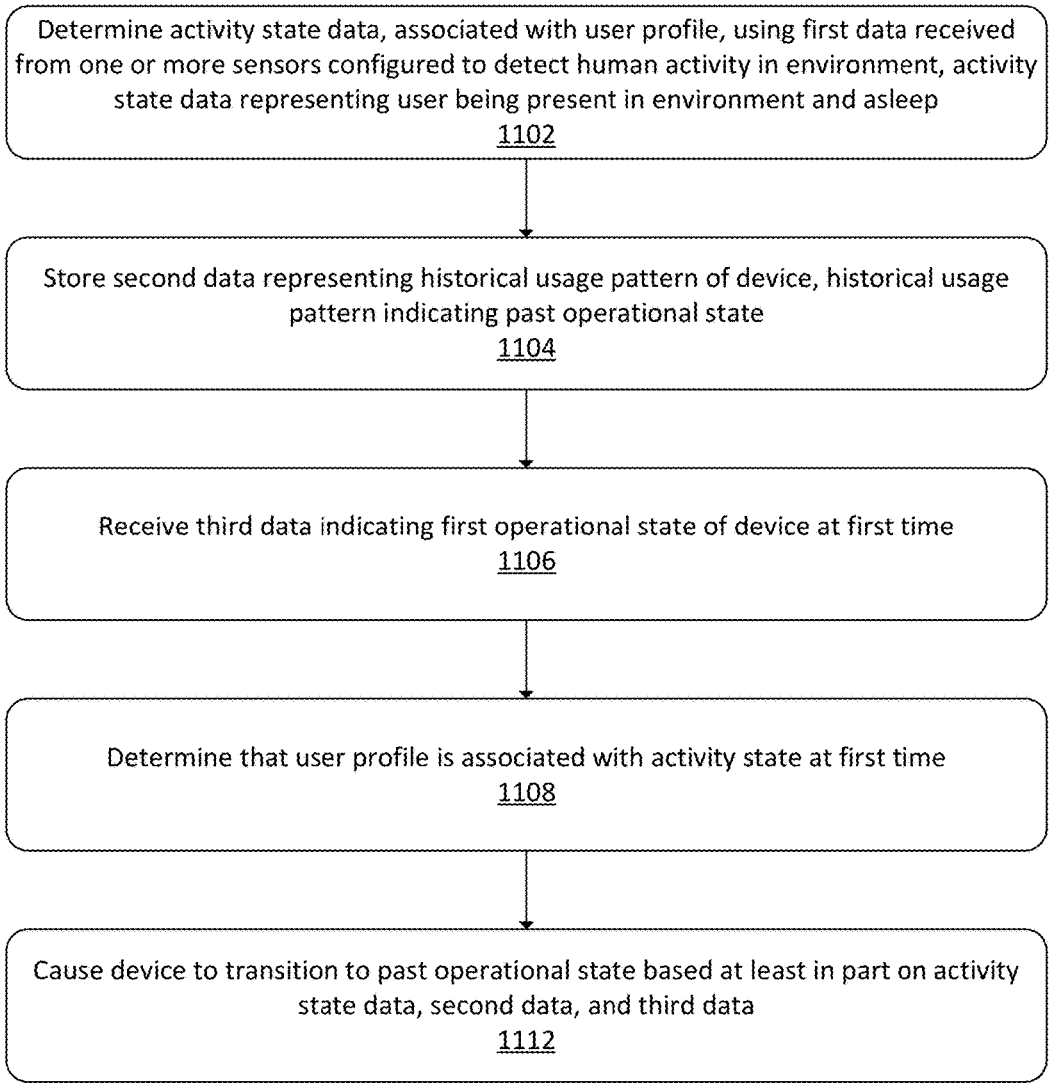
FIG. 11 illustrates a flow diagram of another example process for activity-based device recommendations.

FIGS. 10 and 11 illustrate processes for activity-based device recommendations. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-9 and 12-16, although the processes may be implemented in a wide variety of other environments, architectures and systems.

FIG. 10 illustrates a flow diagram of an example process 1000 for activity-based device recommendations. The order in which the operations or steps are described is not intended to be construed as a limitation, and any number of the described operations may be combined in any order and/or in parallel to implement process 1000.

At block 1002, the process 1000 may include determining a first activity model configured to predict a first state corresponding to an away state indicating absence of user presence and inactivity, wherein the first activity model receives first data representing where a mobile phone associated with a user profile is physically located with respect to a user environment. For example, a neural network model may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic devices and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network model may "learn" how certain events, such as for certain electronic devices and/or environments, impact determining activity states.

The activity models generated and/or trained utilizing the neural network model may include one or more activity models that are configured to accept event data and generate, as output, results indicating that given event data corresponds to a given activity state and, in examples, a confidence associated with the activity state determination. The activity models may include the historical-activity model, which may be configured to determine an activity state associated with historical events associated with an electronic device and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week ago a given environment was associated with an asleep state based at least in part on the event data associated with that given time.

The activity models may also include the current-activity model, which may be configured to determine an activity state associated with a live or near-live event associated with an electronic device and/or environment. For example, the current-activity model may be configured to accept, as features to the current-activity model, event data corresponding to live events and/or near-live events. In examples, use of the current-activity model may be in association with the electronic device and/or the remote system causing one or more sensors or other components of the electronic device to generate live or near-live event data to be utilized by the current-activity model. The current-activity model may generate, as output, data indicating that a given live or near-live event corresponds to a given activity state. For example, the current-activity model may be utilized to determine that at a current time a given environment is associated with an active state based at least in part on event data associated with the current time.

The activity models may also include the future-activity model, which may be configured to predict an activity state associated with events that may occur in the future associated with an electronic device and/or environment. For example, the future-activity model may be configured to accept, as features to the future-activity model, event data corresponding to the historical events and/or live or near-live events. The future-activity model may generate, as output, data indicating that a given event that is likely to occur at a given time in the future is likely to correspond to a given activity state. For example, the future-activity model may be utilized to determine that at a given time a week from now a given environment is likely to be associated with an away state based at least in part on historical event data and/or current event data associated with the given environment.

At block 1004, the process 1000 may include determining a second activity model configured to predict a second state corresponding to an active state indicating both user presence and user activity, wherein the second activity model receives second data representing when a user device in the user environment was last interacted with by a user.

At block 1006, the process 1000 may include determining a third activity model configured to predict a third state corresponding to an asleep state indicating user presence and inactivity, wherein the third activity model receives the first data and the second data.

At block 1008, the process 1000 may include storing third data indicating a historical usage pattern of an electronic device in the environment, the historical usage pattern indicating operational state of the electronic device with respect to time. For example, a datastore may store data indicating when and/or how electronic devices transition states. For example, when a smart light is turned from on to off at a given time, data indicating that state change and/or the time at which the state change occurred may be stored in the datastore. Information associated with the device may also be stored, such as the naming indicator of the device, the device type of the device, user account data associated with the device, a location of the device relative to an environment, a geographical location of the device, etc. The historical usage pattern may indicate that the device in question typically undergoes a state transition at a given time or within a given period of time, such as on given days of the week.

At block 1010, the process 1000 may include receiving fourth data indicating a first operational state of the electronic device at a first time. For example, the electronic device, a voice-enabled device associated with the electronic device, the datastores, and/or a remote system associated with the electronic device may send data indicating the current operational state of the electronic device. Example operational states may include an "on" state, an "off" state, a "locked" state, an "unlocked" state, a temperature setting, etc.

At block 1012, the process 100 may include determining, utilizing the third data and the fourth data, that the electronic device is historically in a second operational state instead of the first operational state. For example, one or more models may be utilized to determine, from the data indicating the historical operational state of the device, that at a given time the device is typically in a second operational state instead of the current operational state. For example, a smart lock may be historically in a locked state at a given time of the day but in a particular instance, at that time of the day, the smart lock may be in an unlocked state.

At block 1014, the process 1000 may include determining, utilizing the third activity model, that the user profile is associated with the asleep state at the first time. For example, an activity model may query the datastores for event data relevant to a request to determine a current activity state associated with the user profile and may utilize the event data, as features to the activity model, to generate output indicating the determined activity state associated with the event data.

At block 1016, the process 1000 may include causing the electronic device to transition to the second operational state in response to the user profile being associated with the asleep state and determining that the electronic device is historically in the second operational state. For example, generally, when a device is in a different state than expected, a recommendation to change the state may be sent to a user device. However, in instances where the activity state indicates that a recommendation will likely not be received, such as when the environment is associated with an asleep state where the user is present but is not moving, the system may instead cause the device to transition states and instead generate a notification that the transition occurred. In these examples, the user may see the notification, such as when the environment transitions to an active state, and provide feedback as to whether the transition should occur in the future.

Additionally, or alternatively, the process 1000 may include determining that the electronic device is historically in the second operational state at a first time of day. The process 1000 may also include receiving fifth data indicating that the electronic device is in the first operational state at the first time of day. The process 1000 may also include determining, at the first time of day, that the user profile is in the active state. The process 1000 may also include, in response to the user profile being in the active state, generating sixth data representing a recommendation to transition the electronic device to the second operational state. The process 1000 may also include sending the sixth data to a user device for output of the recommendation and causing the electronic device to transition to the second operation state in response to receiving seventh data indicating acceptance of the recommendation.

Additionally, or alternatively, the process 1000 may include determining that the electronic device is historically in the second operational state at a first time of day. The process 1000 may also include receiving fifth data indicating that the electronic device is in the first operational state at the first time of day. The process 1000 may also include determining, at the first time of day, that the user profile is in the away state. The process 1000 may also include, in response to the user profile being in the away state, sending sixth data representing a recommendation to transition the electronic device to the second operational state to the user device. The process 1000 may also include causing the electronic device to transition to the second operation state in response to receiving seventh data from the user device indicating acceptance of the recommendation.

Additionally, or alternatively, the process 1000 may include generating fifth data representing a recommendation to transition the electronic device from the first operational state to the second operational state. The process 1000 may also include storing the fifth data in response to the user profile being associated with inactive state. The process 1000 may also include determining that the user profile has transitioned to an active state from the inactive state and sending the fifth data in response to the user profile transitioning to the active state. In these examples, causing the electronic device to transition to the second operational state may be in response to receiving sixth data indicating acceptance of the recommendation.

FIG. 11 illustrates a flow diagram of another example process 1100 for activity-based device recommendations. The order in which the operations or steps are described is not intended to be construed as a limitation, and any number of the described operations may be combined in any order and/or in parallel to implement process 1100.

At block 1102, the process 1100 may include determining activity state data, associated with a user profile, using first data received from one or more sensors configured to detect human activity in an environment, the activity state data representing a user being present in an environment and asleep. For example, a neural network model may be configured to accept the evaluation dataset and/or the training dataset from the supervised machine-learning models to generate and/or train one or more activity models. For example, the neural network model may represent a more robust machine-learning model than the supervised machine-learning models described herein. The neural network model may utilize the event data and the labeling data to identify events indicative of electronic devices and/or environments being in an active state, being in an asleep state, and/or being in an away state. The neural network model may also determine, over time, one or more trends in the event data indicating that certain events are more likely or less likely, depending on the circumstance, to indicate a given activity state. The trends may also include identifying events that were previously unlabeled by the supervised machine-learning models that impact identification of activity state. By so doing, the neural network model may "learn" how certain events, such as for certain electronic devices and/or environments, impact determining activity states.

The activity models generated and/or trained utilizing the neural network model may include one or more activity models that are configured to accept event data and generate, as output, results indicating that given event data corresponds to a given activity state and, in examples, a confidence associated with the activity state determination. The activity models may include the historical-activity model, which may be configured to determine an activity state associated with historical events associated with an electronic device and/or environment. For example, the historical-activity model may be configured to accept, as features to the historical-activity model, event data corresponding to historical events. The historical-activity model may generate, as output, data indicating that a given historical event corresponded to a given activity state. For example, the historical-activity model may be utilized to determine that a given time a week ago a given environment was associated with an asleep state based at least in part on the event data associated with that given time.

The activity models may also include the current-activity model, which may be configured to determine an activity state associated with a live or near-live event associated with an electronic device and/or environment. For example, the current-activity model may be configured to accept, as features to the current-activity model, event data corresponding to live events and/or near-live events. In examples, use of the current-activity model may be in association with the electronic device and/or the remote system causing one or more sensors or other components of the electronic device to generate live or near-live event data to be utilized by the current-activity model. The current-activity model may generate, as output, data indicating that a given live or near-live event corresponds to a given activity state. For example, the current-activity model may be utilized to determine that at a current time a given environment is associated with an active state based at least in part on event data associated with the current time.

The activity models may also include the future-activity model, which may be configured to predict an activity state associated with events that may occur in the future associated with an electronic device and/or environment. For example, the future-activity model may be configured to accept, as features to the future-activity model, event data corresponding to the historical events and/or live or near-live events. The future-activity model may generate, as output, data indicating that a given event that is likely to occur at a given time in the future is likely to correspond to a given activity state. For example, the future-activity model may be utilized to determine that at a given time a week from now a given environment is likely to be associated with an away state based at least in part on historical event data and/or current event data associated with the given environment.

At block 1104, the process 1100 may include stoning second data representing a historical usage pattern of a device, the historical usage pattern indicating a past operational state. For example, a datastore may store data indicating when and/or how electronic devices transition states. For example, when a smart light is turned from on to off at a given time, data indicating that state change and/or the time at which the state change occurred may be stored in the datastore. Information associated with the device may also be stored, such as the naming indicator of the device, the device type of the device, user account data associated with the device, a location of the device relative to an environment, a geographical location of the device, etc. The historical usage pattern may indicate that the device in question typically undergoes a state transition at a given time or within a given period of time, such as on given days of the week.

At block 1106, the process 1100 may include receiving third data indicating a first operational state of the device at a first time. For example, the electronic device, a voice-enabled device associated with the electronic device, the datastores, and/or a remote system associated with the electronic device may send data indicating the current operational state of the electronic device. Example operational states may include an "on" state, an "off" state, a "locked" state, an "unlocked" state, a temperature setting, etc.

At block 1108, the process 1100 may include determining that the user profile is associated with the activity state at the first time. For example, an activity model may query the datastores for event data relevant to a request to determine a current activity state associated with the user profile and may utilize the event data, as features to the activity model, to generate output indicating the determined activity state associated with the event data.

At block 1110, the process 1100 may include causing the device to transition to the past operational state based at least in part on the activity state data, the second data, and the third data. For example, generally, when a device is in a different state than expected, a recommendation to change the state may be sent to a user device. However, in instances where the activity state indicates that a recommendation will likely not be received, such as when the environment is associated with an asleep state where the user is present but is not moving, the system may instead cause the device to transition states and instead generate a notification that the transition occurred. In these examples, the user may see the notification, such as when the environment transitions to an active state and provide feedback as to whether the transition should occur in the future.

Additionally, or alternatively, the process 1100 may include determining that the device is historically in the past operational state at a first time of day. The process 1100 may also include receiving fourth data indicating that the device is in the first operational state at the first time of day. The process 1100 may also include determining, at the first time of day, that the user profile is associated with an active state indicating the user is present and moving. The process 1100 may also include, generating, based at least in part on the user profile being associated with the active state, fifth data representing a recommendation to transition the device to the past operational state. The process 1100 may also include causing the device to transition to the past operational state based at least in part on receiving sixth data indicating acceptance of the recommendation.

Additionally, or alternatively, the process 1100 may include determining that the device is historically in the past operational state at a first time of day. The process 1100 may also include receiving fourth data indicating that the device is in the first operational state at the first time of day. The process 1100 may also include determining, at the first time of day, that the user profile is associated with an away state indicating absence of user presence. The process 1100 may also include sending, based at least in part on the user profile being associated with the away state, fifth data representing a recommendation to transition the device to the past operational state to a user device indicated to be a mobile device associated with the device. The process 1100 may also include causing the device to transition to the past operational state based at least in part on receiving sixth data from the user device indicating acceptance of the recommendation.

Additionally, or alternatively, the process 1100 may include generating fourth data representing a recommendation to transition the device from the first operational state to the past operational state. The process 1100 may also include determining that the user profile has transitioned to an active state from the asleep state. The process 1100 may also include sending the fourth data based at least in part on the user profile transitioning to the active state. In these examples, causing the device to transition to the past operational state may be based at least in part on receiving fifth data indicating acceptance of the recommendation.

Additionally, or alternatively, the process 1100 may include determining that the user profile has transitioned from an active state to an away state. The process 1100 may also include generating fourth data representing a recommendation to transition the electronic device from the first operational state to the past operational state based at least in part on the user profile transitioning from the active state to the away state. The process 1100 may also include sending the fourth data to a mobile user device associated with the device. The process 1100 may also include causing the device to transition to the past operational state based at least in part on receive fifth data from the mobile user device indicating acceptance of the recommendation.

Additionally, or alternatively, the process 1100 may include determining that the device is historically in the past operational state at a first time of day. The process 1100 may also include receiving fourth data indicating that the device is in the first operational state at the first time of day. The process 1100 may also include determining, at the first time of day, that the user profile is associated with an active state and generating, based at least in part on the user profile being associated with the active state, audio data representing a recommendation to transition the device to the past operational state. The process 1100 may also include causing a voice-enabled device associated with the device to output audio corresponding to the audio data based at least in part on the user profile being associated with the active state.

Additionally, or alternatively, the process 1100 may include generating, based at least in part on the user profile being associated with the asleep state, fourth data representing a notification that the device was caused to transition to the past operational state. The process 1100 may also include sending the fourth data to a user device associated with the device, the fourth data causing display of the notification on the user device, the notification including a request to confirm that the transition to the past operational state was acceptable. The process 1100 may also include storing fifth data indicating transition of operational states of the device while the user profile is associated with the asleep state without sending a recommendation are acceptable based at least in part on receiving a response from the user device confirming that the transition was acceptable.

Additionally, or alternatively, the process 1100 may include determining an activity state associated with the user profile at a past time associated with historical usage patterns of the device. The process 1100 may also include determining that the user profile is currently associated with the activity state. In these examples, determining that the device is historically in the past operational state instead of the first operational state may include the device being in the activity state at the past time and currently.

Figure 12:
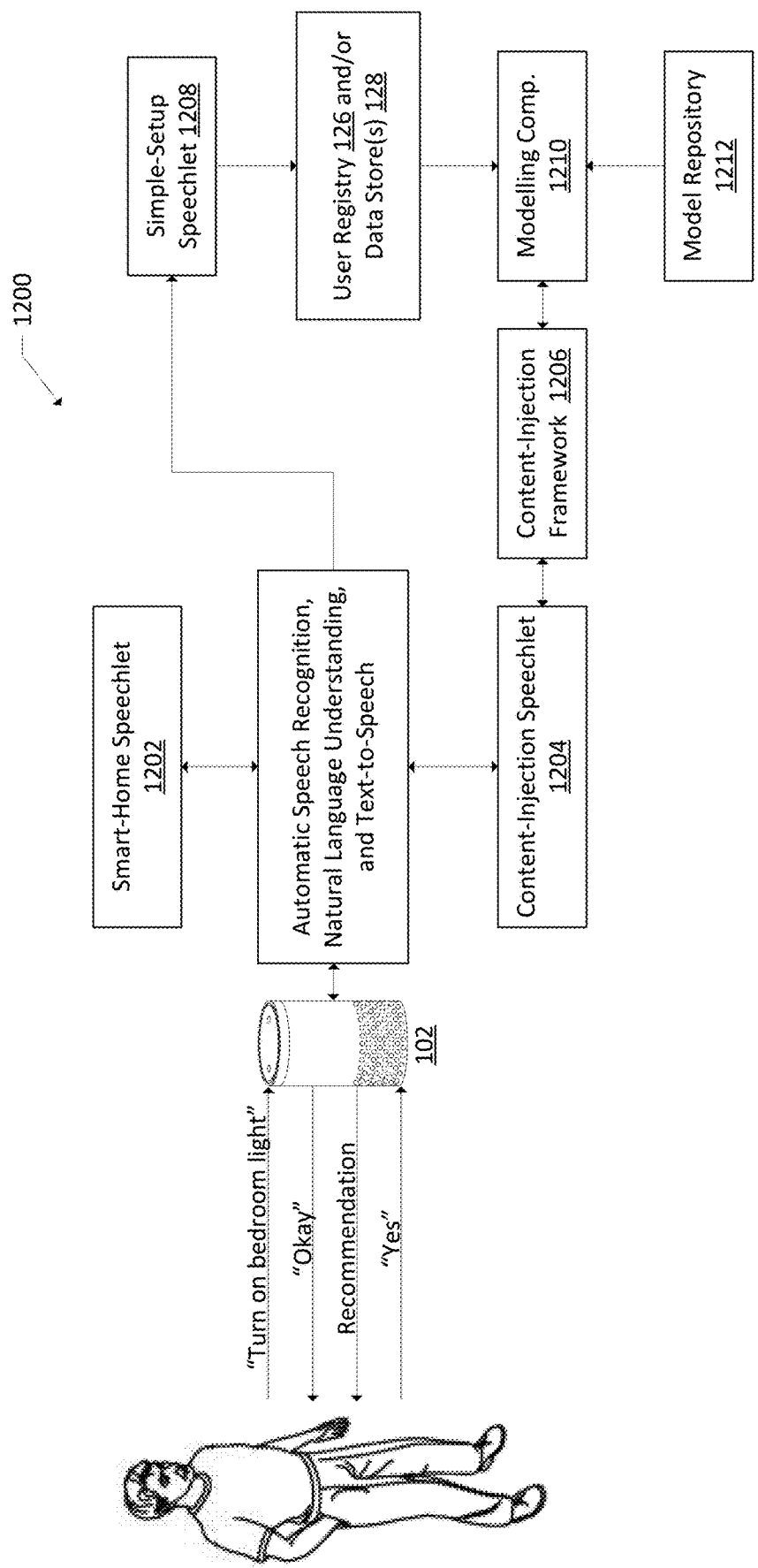
FIG. 12 illustrates a conceptual diagram of components utilized for determining device-related recommendations.

FIG. 12 illustrates a conceptual diagram of example components of devices and systems for intelligent device recommendations. The system 1200 illustrated with respect to FIG. 12 shows conceptual components of the remote system 104 along with a voice-enabled device 102 and a user interacting therewith. FIG. 12 describes the functionality of the remote system 104 in the context of an example user utterance provided by the user.

For example, the user may provide a user utterance such as "turn on bedroom light." The microphones of the voice-enabled device 102 may capture audio corresponding to the user utterance and may generate audio data. The audio data may be sent from the voice-enabled device 102 to the remote system 104. For example, an ASR component 140 may generate text data corresponding to the audio data. An NLU component 142 may generate, based at least in part on the audio data, intent data representing an intent to perform an action. A text-to-speech (TTS) component may generate audio data from text data for output via speakers of the voice-enabled device 102. The ASR component 140, NLU component 142, and TTS component are described in more detail with respect to FIG. 8. In the example provided with respect to FIG. 12, the intent may be, for example, to "turn on" or otherwise activate an accessory device with a naming indicator of "bedroom light." Based at least in part on the intent data, a speechlet configured to handle the intent may be utilized. For example, a smart-home speechlet 1202 may receive the intent data and may utilize that intent data to generate directive data representing a directive for the voice-enabled device 102 to operate the accessory device with the naming indicator of "bedroom light." The directive data may be sent to the voice-enabled device 102, which may further communicate with the "bedroom light" accessory device to cause that accessory device to turn on.

Additionally, in examples, a text-to-speech (TTS) component of the remote system may be utilized to generate audio data corresponding to a response to the user utterance. In the example of FIG. 12, the remote system 104 may successfully identify the intent of the user utterance and may successfully cause the "bedroom light" to "turn on." In these examples, the TTS component may be utilized to generate and/or identify confirmatory audio data. The audio data may be sent to the voice-enabled device 102 for output by speakers of the voice-enabled device 102. Here, the audio data may correspond to audio of "okay," indicating that the user utterance was processed successfully.

Additionally, the remote system 104 may provide a recommendation to the user as described herein. For example, a recommendation may be provided based at least in part on the user providing the user utterance and/or the audio data corresponding to the user utterance being received by the remote system 104. As described more fully above, a modelling component 1210 may be configured to utilize data stored in the user registry 126 and/or the data stores 128 to determine and/or predict useful information to be utilized by the remote system 104. For example, the modelling component 1210 may include one or more models, such as one or more linguistics models, one or more device-activation models, and/or one or more device-affinity models. The models may be stored in a model repository 1212.

As to the linguistics models, machine learning techniques may be utilized to generate models that extract and/or utilize extracted naming indicators associated with the accessory devices and determine semantic similarity between naming indictors for devices associated with a given user profile and/or user account. For example, the linguistics models may be configured and/or trained to recognize similar naming indicators associated with accessory devices, which may indicate that such accessory devices are typically used together. A probability score indicating a probability that the two devices associated with the naming indicators are utilized together may be determined and a matrix representing pair-wised similarity between naming indicators may be generated. In examples, agglomerative clustering, also described as hierarchical clustering, may be utilized to identify, determine, and/or generate device clusters. The linguistics models may also be configured and/or trained to recognize semantic differences in device naming indicators to identify similarities.

A threshold probability score may be identified, determined, and/or generated, and results from the linguistics models may be analyzed with respect to the threshold probability to determine whether, for a given device pair, a recommendation should be presented to the user and/or a device group should be created. Data indicating naming indicators may be stored in the user registry 126 and/or the data stores 128. The modelling component, particularly the linguistics models, may receive the data from the user registry 126 and/or the data stores 128.

As to the device-activation models, rules-based and/or machine learning techniques may be utilized to generate models that extract and/or utilize timing information associated with when an accessory device is turned on and/or turned off. For example, devices that are operated at or near the same time such that they have a similar usage pattern may be candidates for inclusion in a device group. The device-activation models may be configured to receive timing data from the user registry 126 and/or the data stores 128. The timing data may be utilized to determine when accessory devices are turned on and/or turned off. As with the linguistics models, a device pair may be generated for some or each pair of accessory devices associated with a voice-enabled device 102 and/or a user profile and/or user account. A distance matrix may be generated, such as through dynamic time warping distances and/or Euclidean distances. Closer distances may indicate more similar usage patterns between accessory devices. A threshold degree of usage similarity may be identified and/or determined and may be utilized to analyze whether a given device pair has a usage similarity that meets or exceeds the threshold degree of usage similarity. In examples where Euclidean distances are utilized, a threshold distance may be set and distances associated with the device pairs may be analyzed with respect to the threshold distance. Distances that are, for example, less than or equal to the threshold distance may indicate that the devices associated with the device pair are candidates for inclusion in a device group.

As to the device-affinity models, rules-based and/or machine learning techniques may be utilized to generate models that extract and/or utilize device affinity information associated with a frequency at which an accessory device is caused to operate by given voice-enabled devices. For example, the environment may include two or more voice-enabled devices, say one in an office and one in a kitchen. The office voice-enabled device may be frequently utilized to operate certain accessory devices, such as, for example, a first accessory device and a second accessory device. The bedroom voice-enabled device may be frequently utilized to operate other accessory devices, such as, for example, a third accessory device and another accessory device such as a door lock, a security system, etc. The device-affinity models may determine a frequency at which such voice-enabled devices are utilized to operate the accessory devices. In examples where at least two of the accessory devices are operated from a given voice-enabled device, those accessory devices may be candidates for addition to a preexisting device group and/or for generation of a new device group. By way of example, device-affinity data may be stored in the user registry 126 and/or the data stores 128 and may be received by the device-affinity models for identifying which accessory devices are operated by which voice-enabled devices and frequencies associated with such operations.

By way of example, a control rate may be identified for each pair of voice-enabled device and accessory device. The device-affinity models may determine that the first accessory device and the second accessory device are frequently controlled by the first voice-enabled device, making those accessory devices candidates for sending a recommendation to perform an operation associated with the accessory devices. In examples, a threshold control rate may be established and may be utilized to determine if an accessory device is controlled by a particular voice-enabled device with enough frequency to make the accessory device a candidate for performing a given action.

The content-injection speechlet 1204 may be configured to interface between the modelling component 1210 and other components of the remote system 104, such as the ASR component 140 and/or the NLU component 142. For example, when recommendation data is generated as described herein, the content-injection speechlet 1204 may be utilized to generate directive data to be sent to the voice-enabled device 102 for output of the recommendation to the user. Additionally, the user's response may be captured by the voice-enabled device 102 and the content-injection component 1206 may be configured to utilize the response to perform actions, such as transitioning a state of a device, creating the device group, and/or associating a device group with a naming indicator, for example. As shown in FIG. 12, the content-injection speechlet 1204 may be utilized to inject the recommendation data into the flow of interactions with the user. For example, in addition to outputting audio indicating that the user utterance was successfully processed, here illustrated as "okay," the content-injection speechlet 1204 may cause audio data corresponding to the recommendation to be sent to the voice-enabled device 102 for output.

For example, the recommendation of "would you like to turn off Light 1?" may be output by the speakers of the voice-enabled device 102. The user may then provide a user utterance of "yes," which may be captured by the microphones of the voice-enabled device 102 and corresponding audio data may be generated and sent to the remote system 110. The audio data may be analyzed and intent data indicating an intent to transition the state of Light 1. Thereafter, a simple-setup speechlet 1208 may be called to generate the association between the device and the command. Data indicating the state transition, or in other examples device group and/or the association of accessory devices with the device group, may be stored, for example, the user registry 126.

The content injection framework 1206 may be a framework that may allow developers to enhance user interaction by injecting content and/or directive data into available opportunity slots associated with intent data. The slots may be time periods when the customer is open to new interactions. As illustrated in FIG. 12, the time period is after a user provides a user utterance to the voice-enabled device 102 and while that user utterance is being processed. Other example time periods may be different times of the day, days of the week, after and/or before a user may take a particular action such as interacting with a companion application on a personal device associated with the user, etc.

Figure 13:
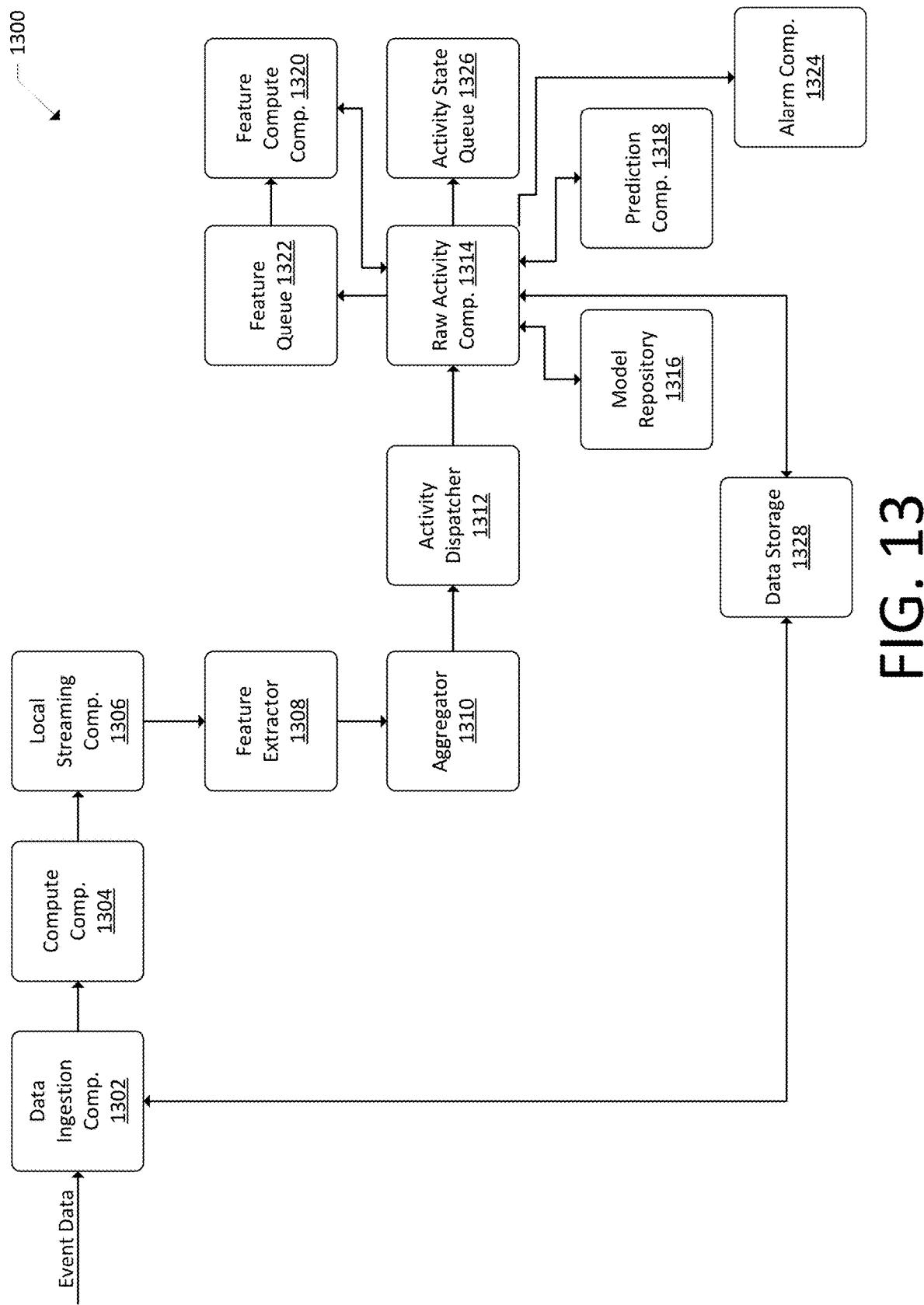
FIG. 13 illustrates a conceptual diagram of components of a system for utilizing activity models to determine activity states.

FIG. 13 illustrates a conceptual diagram of components of a system 1300 for utilizing activity models to determine activity states. The system 1300 may be utilized to intake large amounts of event data, such as data indicating operational state transitions associated with devices, and utilize that data to determine an activity state associated with given user profiles.

For example, a data ingestion component 1302 may be configured to receive event data from one or more sources. The event data may include geofencing data, presence data, acoustic event detection data, audio data representing user utterances, state-change data, and/or feedback data, for example. The event data may be received from one or more devices and/or systems associated with a given user account and/or from multiple user accounts.

The compute component 1304 may be configured receive the event data from the data ingestion component 1302 and may perform one or more preliminary computations using the event data. For example, the preliminary computations may include formatting the data, sorting or otherwise categorizing the data, determining which portions of the data may be utilized for activity state determination, etc.

The local streaming component 1306 may be configured to receive the formatted data from the compute component 1304 and may be configured to stream the formatted data to one or more other components of the system 1300, such as the feature extractor 103. The streaming component 1306 may stream the data pursuant to a streaming schedule and/or based at least in part on a computational load associated with the system 1300.

The feature extractor 1308 may be configured to extract features from the formatted data to be utilized for determining activity states. For example, the feature extractor 1308 may extract data indicating that an operational state change occurred, an indication of the type of state change, and/or a time at which the state change occurred. The aggregator 1310 may be utilized to aggregate the extracted features for use by the activity models described herein. For example, the aggregator 1310 may utilize time-based aggregation to aggregate the extracted features. For example, the extracted features associated with event data from a certain period of time, such as 15 minutes, may be aggregated and utilized to determine an activity state for that period of time. In addition to the above, one or more components, such as the streaming component 1306 and/or the feature extractor 1308 may send data to one or more other dispatchers for reporting the event data. For example, services such as a device target inference component may be able to utilize the event data and/or the extracted features for inferring a device to act upon in response to a user command. The streaming component 1306, for example, may be utilized to provide the event data to a service that may utilize the event data for target inference.

The activity dispatcher 1312 may receive the extracted features from the aggregator 1310 and may send the extracted features and/or other data associated with the event data, in batches for example, to the raw activity component 1314. The raw activity component 1314 may be configured to filter the batches of extracted features, deduplicate activity data, implement guardrails to prevent outlier data from negatively affecting activity state determinations, and requesting activity state determinations from one or more other components of the system 1300.

For example, the raw activity component 1314 may request the use of one or more of the activity models described herein. In examples where the activity state determination is based at least in part on predicted future activity states, the raw activity component 1314 may query the future activity model to predict an activity state at a given time and/or period of time in the future. The raw activity component 1314 may also query a feature compute component 1320 for previous activity state determinations, which may be utilized to determine a current and/or future activity state and/or determine when an activity-state transition occurred. To do so, the raw activity component 1314 may send data indicating activity state determinations to the feature queue 1322, which may be utilized by the feature compute component 1320 to provide information on past activity state determinations to the raw activity component 1314. The raw activity component 1314 may utilize the one or more activity models, the predictions on activity states, and/or the prior activity state determinations to determine, for a given application, an activity state associated with a given user profile and/or environment. The activity state determinations and/or data associated with those determinations may be stored in a data storage component 1328, which may be utilized to send such data, when queried, to the data ingestion component 1302. The data ingestion component 1302 may take in this data along with the event data discussed previously to provide additional data for determining activity states.

Figure 14:
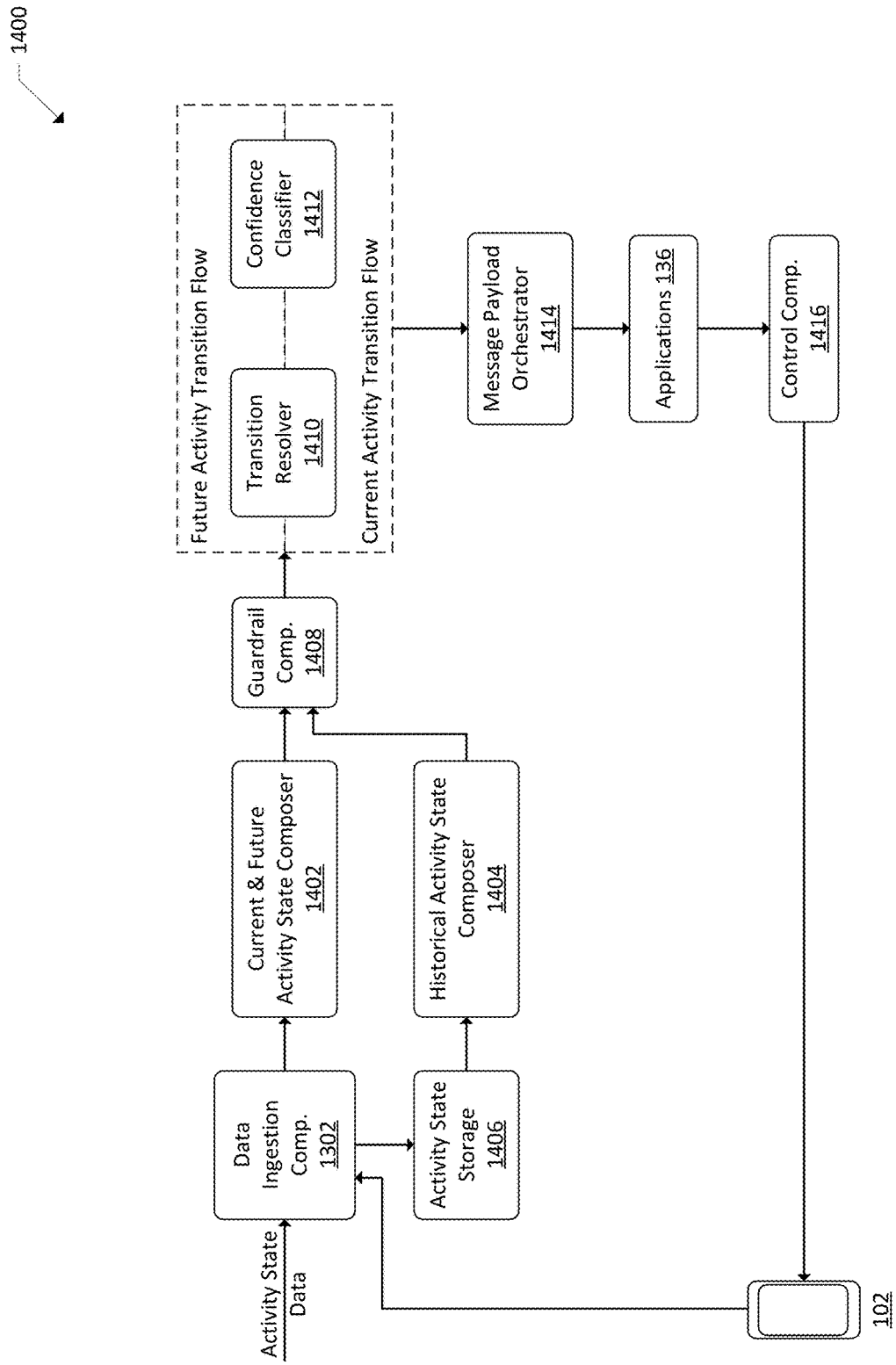
FIG. 14 illustrates a conceptual diagram of components of a system for utilizing determined activity states for performing actions, such as activity-based device recommendations.

The activity state determinations may be provided to the activity state queue 1326, which may be called by one or more systems, such as system 1400 described with respect to FIG. 14, to fetch activity state determinations. Additionally, the activity state determinations may be provided to an alarm component 1324, which may be configured to determine when one or more activity state determinations differ, such as by at least a threshold amount, from typical and/or historical activity state determinations, which may indicate a fault in the system 1300. In these examples, a log of fault may be generated and may be utilized by one or more users to identify the fault and implement corrective action.

FIG. 14 illustrates a conceptual diagram of components of a system 1400 for utilizing determined activity states for performing actions, such as activity-based device recommendations. The system 1400 may be utilized to intake activity state data and provide activity state determinations and related data to one or more applications 136 that are requesting the activity state determinations.

For example, the data ingestion component 1302 may be configured to intake the activity state data representing the activity state determinations, such as the activity state determinations made with respect to FIG. 13. The current and future activity state component 1402 may be configured to receive the activity state data and determine whether a given activity state determination is associated with a current and/or future activity state or a historical activity state. For example, when an activity state determination is received, historical activity state determinations may be stored in association with the activity state storage 1406, which may be called for retrieving the historical activity state determinations. In these examples, the historical activity state component 1404 may retrieve the historical activity state determinations for use by the system 1400. In examples where the activity state determinations are current and/or future activity state determinations, that data may be sent to the current and future activity state component 1402 for use by the system 1400. The activity state data may then be provided to a guardrail component 1408, which may be utilized to identify outlier activity state determinations that may, if processed, alter the activity state determinations made by the system 1400. Those outlier activity state determinations may be ignored or otherwise not utilized by the system 1400.

The remaining activity state determinations may be provided to the transition resolver 1410. The transition resolver 1410 may be configured to determine when a given activity state starts and end. For example, if a given device is currently associated with an active state as determined utilizing the systems described herein, the transition resolver 1410 may be configured to determine when the activity state transitions from the active state to one of the inactive state or the away state. Additionally, the confidence classifier 1412 may be configured to determine a confidence value associated with the determined transitions. For example, a given state start time may be associated with a given confidence value indicating how confident the determination is that the start time was at the time indicated. The confidence classifier 1412 may also determine, for a given transition whether that transition is certain, such as when the confidence value satisfies a threshold confidence value, or unknown, such as when the confidence value does not satisfy the threshold confidence value.

The activity state determinations, transitions, and/or confidence values may be provided to a message payload orchestrator 1414, which may be configured to send a responsive message to the one or more applications 136 in response to a request for activity state determinations. The one or more applications 136 may utilize the activity state determination for one or more purposes, such as how and/or when to send activity-based device recommendations. In additional examples, the activity-based determinations described herein may be utilized to determine what recommendation to provide to a user device and/or when to send such a recommendation. For example, device-usage data may be utilized by a remote system to determine when a recommendation is to be surfaced to a user device. By way of example, a given device may be associated with a given device-usage pattern. That device-usage pattern may indicate when a device is operated, how the device is operated, and/or details associated with the device, such as a naming indicator associated with the device and/or the device type of the device, etc. This information may be utilized to determine when a recommendation or otherwise a "hunch" is to be surfaced to a user device. The recommendations may include requests to operate the device in a certain way, to change information associated with the device, to add the device to a device group, to add the device to a device routine, etc. In addition to utilizing the device-usage data to determine when and how to surface such recommendations, the activity-based determinations described herein may also be used to determine when and how to surface recommendations.

For example, when the activity model(s) described herein determine that a given device and/or environment is associated with an active state, the recommendations may be provided to a device within the environment for output by the device because a user is currently in that environment and is moving in a manner associated with an active state. In other examples, such as when the environment is associated with an asleep state, the recommendation may not be output by the device because a user is not currently active in the environment, but instead the recommendation may be provided to a user device by way of a message that may be viewed by the user at a later time. In addition to utilizing activity-based determinations to determine when and how to provide a recommendation, the activity-based determinations may also be utilized to determine what recommendation to provide. For example, when a device is associated with an away state and the device-usage data indicates that a smart door lock is typically locked but in this instance the smart door lock is in an unlocked state, the system may utilize both the device-usage data and the indication that the environment is associated with an away state to surface a recommendation to cause the smart door lock to transition to a locked state. In still other examples, the activity-based determinations may be utilized to determine whether to send a recommendation or whether to perform an action without sending a recommendation and instead, in examples, send a notification that the action has been taken. For example, if an environment is associated with an asleep state, indicating that a user is present but is not active, instead of surfacing a recommendation to lock a smart door lock that is typically in a lock state but is currently in an unlocked state, the system may cause the device to transition to the locked state and provide a notification of the action to a user device.

Additionally, a control component 146 may be utilized to control the sending of request data for user input associated with the activity state determinations and/or device recommendations described herein. Those recommendations may be sent to user devices, which may receive responsive user input. User input data corresponding to the user input may be provided to the data ingestion component 1302 and/or to one or more other components to improve the accuracy of the activity state determinations described herein.

Figure 15:
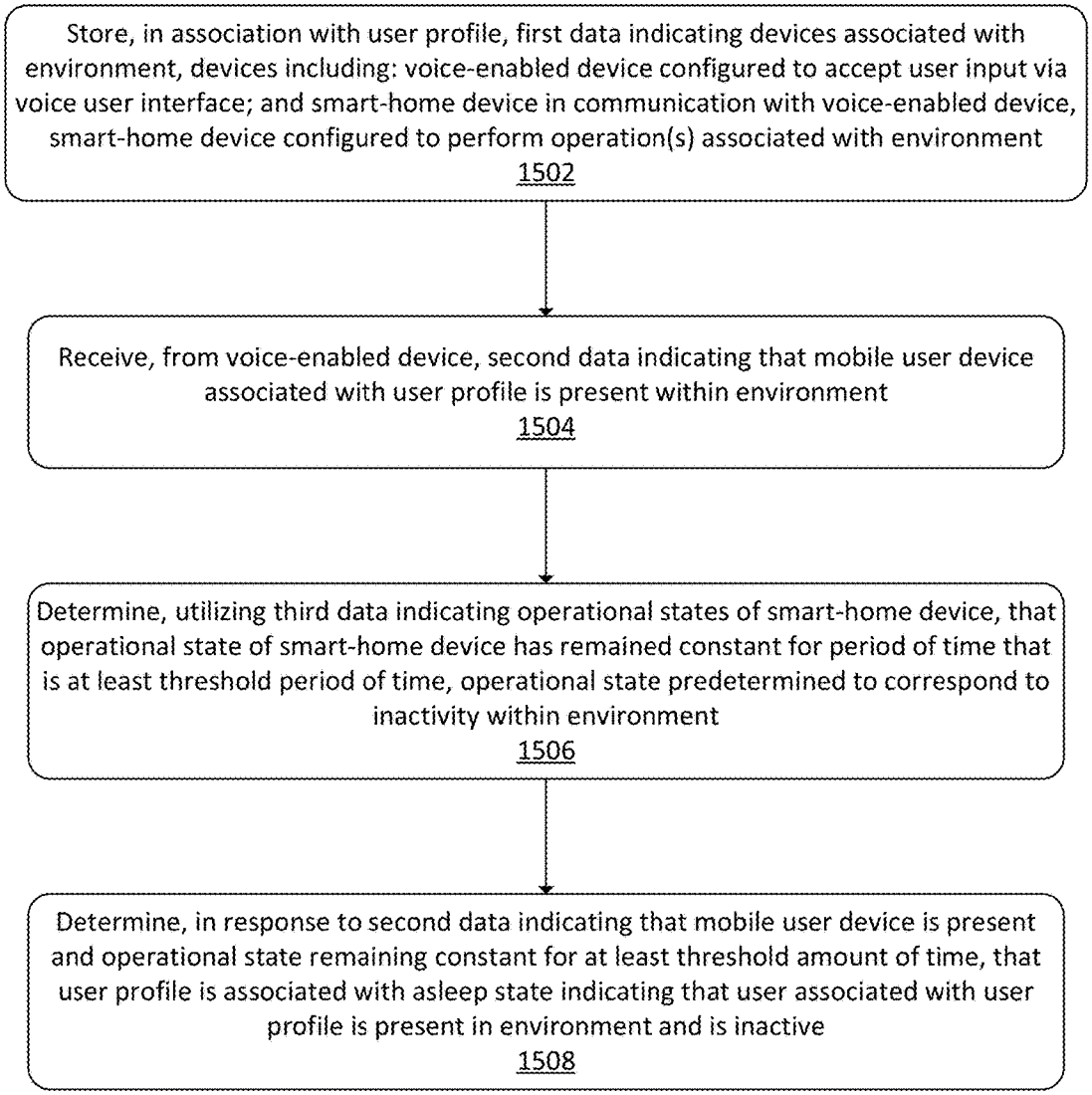
FIG. 15 illustrates a flow diagram of an example process for determining an asleep state utilizing device signals.
Figure 16:
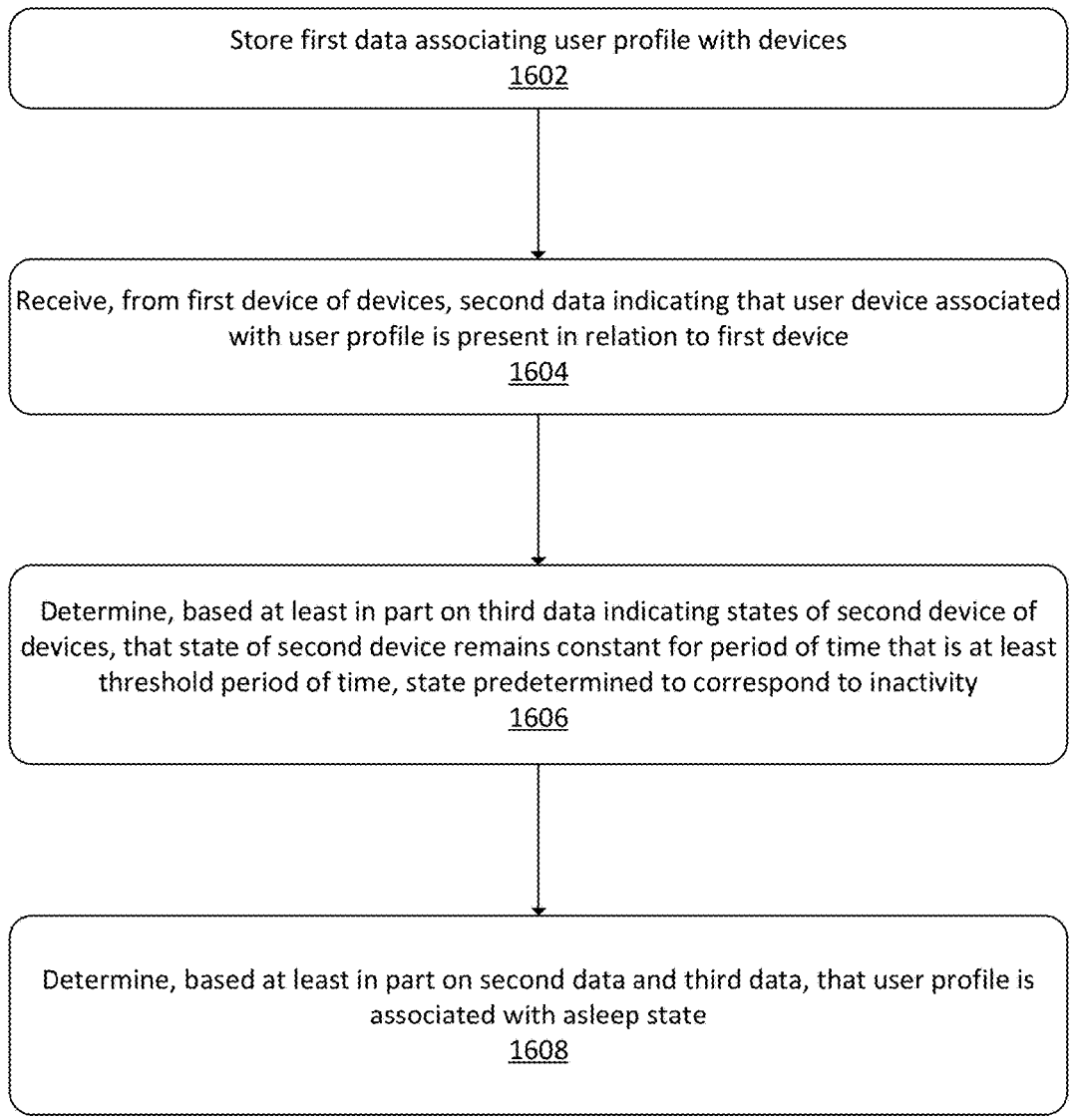
FIG. 16 illustrates a flow diagram of another example process for determining an asleep state utilizing device signals.

FIGS. 15 and 16 illustrate processes for determining an asleep state utilizing device signals. The processes described herein are illustrated as collections of blocks in logical flow diagrams, which represent a sequence of operations, some or all of which may be implemented in hardware, software or a combination thereof. In the context of software, the blocks may represent computer-executable instructions stored on one or more computer-readable media that, when executed by one or more processors, program the processors to perform the recited operations. Generally, computer-executable instructions include routines, programs, objects, components, data structures and the like that perform particular functions or implement particular data types. The order in which the blocks are described should not be construed as a limitation, unless specifically noted. Any number of the described blocks may be combined in any order and/or in parallel to implement the process, or alternative processes, and not all of the blocks need be executed. For discussion purposes, the processes are described with reference to the environments, architectures and systems described in the examples herein, such as, for example those described with respect to FIGS. 1-14, although the processes may be implemented in a wide variety of other environments, architectures and systems.

FIG. 15 illustrates a flow diagram of an example process 1500 for determining an asleep state utilizing device signals. The order in which the operations or steps are described is not intended to be construed as a limitation, and any number of the described operations may be combined in any order and/or in parallel to implement process 1500.

At block 1502, the process 1500 may include storing, in association with a user profile, first data indicating devices associated with an environment, the devices including: a voice-enabled device configured to accept user input via a voice user interface; and a smart-home device in communication with the voice-enabled device, the smart-home device configured to perform one or more operations associated with the environment. For example, a user registry may store device identifiers for devices associated with a given user profile. A given user profile may be associated with multiple devices, including multiple voice-enabled devices, such as personal assistant devices configured to receive user utterances and perform actions based on those utterances, and including multiple other devices, such as smart-home devices that may be utilized in many different ways, such as for operating lights, plugs, appliances, thermostats, locks, etc.

At block 1504, the process 1500 may include receiving, from the voice-enabled device, second data indicating that a mobile user device associated with the user profile is present within the environment. For example, when a mobile user device is close enough to a voice-enabled device to wirelessly communicate with the voice-enabled device, the mobile user device may send signals to the voice-enabled device, and the voice-enabled device may send signals to the mobile user device, for at least establishing a data transmission channel between the devices. In examples, this device beaconing may be utilized to determine not only that a mobile user device is in the environment of the voice-enabled device, but also may provide an approximate location of the mobile user device and/or a distance of the mobile user device from the voice-enabled device. In examples, global positioning data may be sent to the voice-enabled device to determine that the mobile user device is in proximity to the voice-enabled device.

At block 1506, the process 1500 may include determining, utilizing third data indicating operational states of the smart-home device, that an operational state of the smart-home device has remained constant for a period of time that is at least a threshold period of time, the operational state predetermined to correspond to inactivity within the environment. For example, when a user is asleep, that user is not causing smart-home devices to transition states. For example, the user is not operating lights, plugs, appliances, etc. For some devices, such as lights, appliances, locks, etc., when those devices are maintained in a given state, such as an "off" state for a certain amount of time, that may indicate that the user is asleep. In these examples, contextual information such as the time of day, day of the week, and/or historical event data may be utilized to determine if maintaining a device state for a given amount of time is indicative of an asleep state. For example, a device maintaining an "off" state for 30 minutes at 11:00 pm on a Tuesday, such as when the device is typically in that state at that time, may indicate that the user profile associated with the user is in an asleep state.

At block 1508, the process 1500 may include determining, in response to the second data indicating that the mobile user device is present and the operational state remaining constant for at least the threshold amount of time, that the user profile is associated with an asleep state indicating that a user associated with the user profile is present in the environment and is inactive. For example, the signals from the smart-home devices indicating that those devices have not changed state may indicate that the environment is associated with an inactive state, which may be an away state or an asleep state. However, when other data, such as the data from the mobile user device, indicates that a user is present, the system may determine that the user profile is to be associated with the asleep state instead of the away state.

Additionally, or alternatively, the process 1500 may include determining that receipt of audio data including user speech from the voice-enabled device during the period of time is absent. In these examples, determining that the user profile is associated with the asleep state may be in response to determining that receipt of the audio data during the period of time is absent.

Additionally, or alternatively, the process 1500 may include sending, to the voice-enabled device, request data for an indication of acoustic events detected by the voice-enabled device during the period of time. The process 1500 may also include receiving, from the voice-enabled device, third data indicating that predefined acoustic events indicating activity in the environment were undetected. In these examples, determining that the user profile is associated with the asleep state may be in response to the third data indicating that the predefined acoustic events were undetected.

Additionally, or alternatively, the process 1500 may include receiving, while the user profile is associated with the asleep state, an indication that the smart-home device has transitioned from a first operational state to a second operational state. The process 1500 may also include determining, in response to receiving the indication, that a command to transition the smart-home device was sent in response to user input received at the smart-home device. In these examples, in response to determining that the command was sent in response to the user input, the process 1500 may include associating the user profile with an active state instead of the asleep state.

FIG. 16 illustrates a flow diagram of an example process 1600 for determining an asleep state utilizing device signals. The order in which the operations or steps are described is not intended to be construed as a limitation, and any number of the described operations may be combined in any order and/or in parallel to implement process 1600.

At block 1602, the process 1600 may include storing first data associating a user profile with devices. For example, a user registry may store device identifiers for devices associated with a given user profile. A given user profile may be associated with multiple devices, including multiple voice-enabled devices, such as personal assistant devices configured to receive user utterances and perform actions based on those utterances, and including multiple other devices, such as smart-home devices that may be utilized in many different ways, such as for operating lights, plugs, appliances, thermostats, locks, etc.

At block 1604, the process 1600 may include receiving, from a first device of the devices, second data indicating that a user device associated with the user profile is present in relation to the first device. For example, when a mobile user device is close enough to a voice-enabled device to wirelessly communicate with the voice-enabled device, the mobile user device may send signals to the voice-enabled device, and the voice-enabled device may send signals to the mobile user device, for at least establishing a data transmission channel between the devices. In examples, this device beaconing may be utilized to determine not only that a mobile user device is in the environment of the voice-enabled device, but also may provide an approximate location of the mobile user device and/or a distance of the mobile user device from the voice-enabled device. In examples, global positioning data may be sent to the voice-enabled device to determine that the mobile user device is in proximity to the voice-enabled device.

At block 1606, the process 1600 may include determining, based at least in part on third data indicating states of a second device of the devices, that a state of the second device remains constant for period of time that is at least a threshold period of time, the state predetermined to correspond to inactivity. For example, when a user is asleep, that user is not causing smart-home devices to transition states. For example, the user is not operating lights, plugs, appliances, etc. For some devices, such as lights, appliances, locks, etc., when those devices are maintained in a given state, such as an "off" state for a certain amount of time, that may indicate that the user is asleep. In these examples, contextual information such as the time of day, day of the week, and/or historical event data may be utilized to determine if maintaining a device state for a given amount of time is indicative of an asleep state. For example, a device maintaining an "off" state for 30 minutes at 11:00 pm on a Tuesday, such as when the device is typically in that state at that time, may indicate that the user profile associated with the user is in an asleep state.

At block 1608, the process 1600 may include determining, based at least in part on the second data and the third data, that the user profile is associated with an asleep state. For example, the signals from the smart-home devices indicating that those devices have not changed state may indicate that the environment is associated with an inactive state, which may be an away state or an asleep state. However, when other data, such as the data from the mobile user device, indicates that a user is present, the system may determine that the user profile is to be associated with the asleep state instead of the away state.

Additionally, or alternatively, the process 1600 may include determining that receipt of audio data including user speech from the first device during the period of time is absent. In these examples, determining that the user profile is associated with the asleep state may be based at least in part on determining that receipt of the audio data during the period of time is absent.

Additionally, or alternatively, the process 1600 may include sending, to the first device, request data for an indication of acoustic events detected during the period of time. The process 1600 may also include receiving, from the first device, fourth data indicating that predefined acoustic events indicating activity in the environment were undetected. In these examples, determining that the user profile is associated with the asleep state may be based at least in part on the fourth data.

Additionally, or alternatively, the process 1600 may include receiving, while the user profile is associated with the asleep state, an indication that the second device has transitioned from a first state to a second state. The process 1600 may also include determining, based at least in part on the indication, that a command to transition the second device was sent based at least in part on user input. The process 1600 may also include associating, based at least in part on determining that the command was sent in response to the user input, the user profile with an active state.

Additionally, or alternatively, the process 1600 may include receiving, from the first device, fourth data indicating that an ambient light value determined by an ambient light sensor in the environment satisfies a threshold ambient light value. In these examples, determining that the user profile is associated with the asleep state may be based at least in part on the fourth data.

Additionally, or alternatively, the process 1600 may include receiving fourth data indicating that a security system associated with the user profile is in a home state, the home state indicating that the security system is configured to alarm without regard to motion detected by a motion sensor of the security system. The process 1600 may also include determining that the user profile is associated with the asleep state may be based at least in part on the fourth data.

Additionally, or alternatively, the process 1600 may include receiving fourth data indicating that a force sensor of a third device, associated with a bed disposed in the environment, has detected a force value that satisfies a threshold force value, the threshold force value indicating that a user is laying on the bed. In these examples, determining that the user profile is associated with the asleep state may be based at least in part on the fourth data.

Additionally, or alternatively, the process 1600 may include receiving, from the first device, audio data representing a user utterance. The process 1600 may also include determining, utilizing the audio data, that the user utterance corresponds to a request to enable a routine associated with inactivity in the environment. In these examples, determining that the user profile is associated with the asleep state may be based at least in part on determining that the user utterance corresponds to the request to enable the routine.

While the foregoing invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims.

What is claimed is:

1. A method, comprising:
storing first data associating a user profile with a plurality of devices;
receiving, from a first device of the plurality of devices, second data indicating that a user device associated with the user profile is present in relation to the first device;
determining that the first device is disposed within a room having a room identifier and the user device is disposed within the room, wherein the room identifier for the room differs from other room identifiers for other rooms associated with the user profile;
determining, based at least in part on third data indicating states of a second device of the plurality of devices, that a state of the second device disposed within the room remains constant for a period of time that is at least a threshold period of time, the state predetermined to correspond to device inactivity;
determining, utilizing machine learning, fourth data indicating:
  a first device state transition from a first operational state to a second operational state indicating historical cessation of an asleep state for the room identifier, the asleep state associated with a person sleeping; and
  a second device state transition from the second operational state to the first operational state indicating historical initiation of the asleep state for the room identifier, wherein the first device state transition and the second device state transition differ for at least one of the other room identifiers for the other rooms;
determining, during the period of time, an absence of a first acoustic event predefined as being associated with an awake state within the room;
determining, during the period of time, that a second acoustic event predefined as being associated with the asleep state is detected within the room;
associating the room identifier of the room with the asleep state based at least in part on:
  the user device being present in relation to the first device;
  the state of the second device remaining constant for the period of time;
  the second device performing the second device state transition;
  determining the absence of the first acoustic event; and
  determining the second acoustic event has been detected; and
causing, based at least in part on associating the room identifier with the asleep state, one or more smart home applications associated with the user profile to perform at least one of first notification actions or first recommendation actions associated with the room that air predefined to be performed while the user profile is associated with the asleep state, the at least one of the first notification actions or the first recommendation actions differing from other notification actions and other recommendation actions performed by the one or more smart home applications when associated with the awake state.

2. The method of claim 1, further comprising:
determining that receipt of audio data including user speech from the first device during the period of time is absent; and
wherein associating the room identifier with the asleep state comprises associating the room identifier with the asleep state based at least in part on determining that receipt of the audio data during the period of time is absent.

3. The method of claim 1, further comprising:
sending, to the first device, request data for an indication of acoustic events detected during the period of time;
receiving, from the first device, fifth data indicating that the first acoustic event was undetected; and
wherein determining the absence of the first acoustic event is based at least in part on the fifth data.

4. The method of claim 1, further comprising:
receiving fifth data indicating that a security system associated with the user profile is in a home state, the home state disregarding motion detected by a motion sensor of the security system; and
wherein associating the room identifier with the asleep state comprises associating the room identifier with the asleep state based at least in part on the fifth data.

5. The method of claim 1, further comprising:
receiving fifth data indicating that a force sensor of a third device, associated with a bed disposed in an environment, has detected a force value that satisfies a threshold force value, the threshold force value indicating that a user is laying on the bed; and
wherein associating the room identifier with the asleep state comprises associating the room identifier with the asleep state based at least in part on the fifth data.

6. The method of claim 1, further comprising:
determining to enable a routine associated with inactivity in an environment; and
wherein associating the room identifier with the asleep state comprises associating the room identifier with the asleep state based at least in part on determining to enable the routine.

7. A system, comprising:
one or more processors; and
non-transitory computer-readable media storing computer-executable instructions that, when executed by the one or more processors, cause the one or more processors to perform operations comprising:
  storing first data associating a user profile with a plurality of devices;
  receiving, from a first device of the plurality of devices, second data indicating that a user device associated with the user profile is present in relation to the first device;
  determining that the first device is disposed within a room having a room identifier and the user device is disposed within the room, wherein the room identifier for the room differs from other room identifiers for other rooms associated with the user profile;
  determining, based at least in part on third data indicating states of a second device of the plurality of devices, that a state of the second device disposed within the room remains constant for a period of time that is at least a threshold period of time, the state predetermined to correspond to device inactivity;

determining, utilizing machine learning, fourth data indicating:
- a first device state transition from a first operational state to a second operational state indicating historical cessation of an asleep state for the room identifier, the asleep state associated with a person sleeping; and
- a second device state transition from the second operational state to the first operational state indicating historical initiation of the asleep state for the room identifier, wherein the first device state transition and the second device state transition differ for at least one of the other room identifiers for the other rooms;

determining, during the period of time, an absence of a first acoustic event predefined as being associated with an awake state within the room;

determining, during the period of time, that a second acoustic event predefined as being associated with the asleep state is detected within the room;

associating the room identifier of the room with an asleep state based at least in part on:
- the user device being present in relation to the first device;
- the state of the second device remaining constant for the period of time;
- the second device performing the second device state transition;
- determining the absence of the first acoustic event; and
- determining the second acoustic event has been detected; and causing, based at least in part on associating the room identifier with the asleep state, one or more smart home applications associated with the user profile to perform at least one of first notification actions or first recommendation actions within the room predefined to be performed while the user profile is associated with the asleep state, the at least one of first notification actions or the first recommendation actions differing from other notification actions and other recommendation actions performed by the one or more smart home applications when associated with the awake state.

8. The system of claim 7, the operations further comprising:
determining that receipt of audio data including user speech from the first device during the period of time is absent; and
wherein associating the room identifier with the asleep state comprises associating the room identifier with the asleep state based at least in part on determining that receipt of the audio data during the period of time is absent.

9. The system of claim 7, the operations further comprising:
sending, to the first device, request data for an indication of acoustic events detected during the period of time;
receiving, from the first device, fifth data indicating that the first acoustic event was undetected; and
wherein determining the absence of the first acoustic event is based at least in part on the fifth data.

10. The system of claim 7, the operations further comprising:
receiving, while the user profile is associated with the asleep state, an indication that the second device has transitioned from the first operational state to the second operational state;
determining, based at least in part on the indication, that a command to transition the second device was sent based at least in part on user input; and
associating, based at least in part on determining that the command was sent in response to the user input, the room identifier with an active state.

11. The system of claim 7, the operations further comprising:
receiving, from the first device, fifth data indicating that an ambient light value determined by an ambient light sensor in an environment satisfies a threshold ambient light value; and
wherein associating the room identifier with the asleep state comprises associating the room identifier with the asleep state based at least in part on the fifth data.

12. The system of claim 7, the operations further comprising:
receiving fifth data indicating that a security system associated with the user profile is in a home state, the home state disregarding motion detected by a motion sensor of the security system; and
wherein associating the room identifier with the asleep state comprises associating the room identifier with the asleep state based at least in part on the fifth data.

13. The system of claim 7, the operations further comprising:
receiving fifth data indicating that a force sensor of a third device, associated with a bed disposed in an environment, has detected a force value that satisfies a threshold force value, the threshold force value indicating that a user is laying on the bed; and
wherein associating the room identifier with the asleep state comprises associating the room identifier with the asleep state based at least in part on the fifth data.

14. The method of claim 1, further comprising:
receiving audio data from the first device during the period of time;
determining that a portion of the audio data corresponds at least in part to user sound;
determining that the portion of the audio data lacks speech input; and
wherein associating the room identifier with the asleep state comprises associating the room identifier with the asleep state based at least in part on the portion of the audio data lacking the speech input.

15. The method of claim 1, further comprising:
querying, based at least in part on the state of the second device remaining constant for the period of time, the plurality of devices for presence data indicating user presence;
receiving response data indicating user presence was unidentified by the plurality of devices; and
wherein associating the room identifier with the asleep state comprises associating the room identifier with the asleep state based at least in part on the response data.

16. The system of claim 7, the operations further comprising:
receiving audio data from the first device during the period of time;
determining that a portion of the audio data corresponds at least in part to user sound;
determining that the portion of the audio data lacks speech input; and wherein associating the room identifier with the asleep state comprises associating the room identifier with the asleep state based at least in part on the portion of the audio data lacking the speech input.

17. The system of claim 7, the operations further comprising:
    querying, based at least in part on the state of the second device remaining constant for the period of time, the plurality of devices for presence data indicating user presence;
    receiving response data indicating user presence was unidentified by the plurality of devices; and
    wherein associating the room identifier with the asleep state comprises associating the room identifier with the asleep state based at least in part on the response data.

18. The method of claim 1, further comprising:
    querying a model to predict future activity states associated with the second device; and
    receiving predicted future activity states from the model in response to the querying, and wherein associating the room identifier with the asleep state is based at least in part on the predicted future activity states.

19. The method of claim 1, further comprising:
    identifying a content injection framework associated with the asleep state; and
    determining when to cause the one or more smart home applications to perform the at least one of first notification actions or the first recommendation actions based at least in part on the content injection framework.

20. The method of claim 1, wherein determining the fourth data is performed utilizing a machine learning model trained to determine the first device state transition and the second device state transition.

\* \* \* \* \*